US008563742B2

(12) United States Patent
Mjalli et al.

(10) Patent No.: US 8,563,742 B2
(45) Date of Patent: Oct. 22, 2013

(54) SUBSTITUTED AMINOTHIAZOLE DERIVATIVES, PHARMACEUTICAL COMPOSITIONS, AND METHODS OF USE

(75) Inventors: Adnan M. M. Mjalli, Oak Ridge, NC (US); Bapu Gaddam, High Point, NC (US); Robert C. Andrews, Jamestown, NC (US); Samuel Victory, Oak Ridge, NC (US); Suparna Gupta, Greensboro, NC (US)

(73) Assignee: High Point Pharmaceuticals, LLC, High Point, NC (US)

( * ) Notice: Subject to any disclaimer, the term of this patent is extended or adjusted under 35 U.S.C. 154(b) by 636 days.

(21) Appl. No.: 12/547,018

(22) Filed: Aug. 25, 2009

(65) Prior Publication Data

US 2010/0056587 A1 Mar. 4, 2010

Related U.S. Application Data

(60) Provisional application No. 61/092,844, filed on Aug. 29, 2008.

(51) Int. Cl.
*A61K 31/427* (2006.01)
*C07D 417/12* (2006.01)

(52) U.S. Cl.
USPC ........................................... 548/194; 514/370

(58) Field of Classification Search
USPC ....................................................... 548/194
See application file for complete search history.

(56) References Cited

U.S. PATENT DOCUMENTS

| | | | |
|---|---|---|---|
| 5,463,071 | A | 10/1995 | Himmelsbach et al. |
| 5,470,855 | A | 11/1995 | Bernat et al. |
| 5,502,025 | A | 3/1996 | Bussler |
| 5,627,131 | A | 5/1997 | Shribbs et al. |
| 5,643,932 | A | 7/1997 | Chihiro et al. |
| 6,011,048 | A | 1/2000 | Mathvink et al. |
| 6,303,749 | B1 | 10/2001 | Jarosinski |
| 6,344,470 | B1 | 2/2002 | Fontaine et al. |
| 6,596,746 | B1 | 7/2003 | Das et al. |
| 6,689,873 | B1 | 2/2004 | Van der Ploeg et al. |
| 6,699,896 | B1 | 3/2004 | Malamas |
| 6,734,175 | B2 | 5/2004 | Hadcock et al. |
| 6,787,542 | B2 | 9/2004 | Wang et al. |
| 7,253,197 | B2 | 8/2007 | Guba et al. |
| 7,361,672 | B2 | 4/2008 | Boehringer et al. |
| 7,820,704 | B2 | 10/2010 | Mjalli et al. |
| 2002/0132807 | A1 | 9/2002 | Wang et al. |
| 2002/0151463 | A1 | 10/2002 | Woychik et al. |
| 2003/0082737 | A1 | 5/2003 | Stark et al. |
| 2003/0158199 | A1 | 8/2003 | Stieber et al. |
| 2004/0132788 | A1 | 7/2004 | Chabrier De Lassauniere et al. |
| 2005/0009891 | A1 | 1/2005 | Lee |
| 2005/0014746 | A1 | 1/2005 | Wang et al. |
| 2005/0014805 | A1 | 1/2005 | Zhang et al. |
| 2005/0038087 | A1 | 2/2005 | Chabrier De Lassauniere et al. |
| 2005/0065196 | A1 | 3/2005 | Inaba et al. |
| 2005/0261305 | A1 | 11/2005 | Das et al. |
| 2007/0213301 | A1 | 9/2007 | Zhang et al. |

FOREIGN PATENT DOCUMENTS

| | | |
|---|---|---|
| EP | 0 354 201 | 2/1990 |
| EP | 0 480 902 | 4/1992 |
| EP | 0 556 396 | 8/1993 |
| EP | 0 627 423 | 9/1995 |
| EP | 1 285 658 | 2/2003 |
| EP | 1 452 530 | 9/2004 |
| EP | 1 553 091 | 9/2004 |
| JP | 63203672 | 8/1988 |
| JP | 07149745 | 6/1995 |
| WO | WO 93-17681 | 9/1993 |
| WO | WO 97-47299 | 12/1997 |
| WO | WO 99-50295 | 10/1999 |
| WO | WO 99-58511 | 11/1999 |
| WO | WO 99-58514 | 11/1999 |
| WO | WO 00-11954 | 3/2000 |
| WO | WO 01-58871 | 8/2001 |
| WO | WO 02-02539 | 1/2002 |
| WO | WO 03-040117 | 5/2003 |
| WO | WO 03-068738 | 8/2003 |
| WO | WO 2004-004447 | 1/2004 |
| WO | WO 2005/103022 A1 | 11/2005 |
| WO | WO 2006-038594 | 4/2006 |

OTHER PUBLICATIONS

Adan et al., "Inverse agonism gains weight," Trends in Pharmacological Sciences, vol. 24, pp. 315-321, (2003).
Ahluwalia et al., "Synthesis & Antimicrobial & Antifungal Activities of Some New 2-[N-2'-Mercapto-1', 3' 4'- thiadiazol-5'-yl)amino]-4-arylthiazole Derivatives," Indian Journal of Chemistry, Section B, Organic Chemistry Including Medicinal Chemistry, vol. 26, pp. 88-90, (1987).
Argyropoulos et al., "A polymorphism in the human agouti-related protein is associated with late-onset obesity," The Journal of Clinical Endocrinology & Metabolism, vol. 87, pp. 4198-4202, (2002).
Bednarek et al., "Selective, high affinity peptide antagonists of a-melanotropin action at human melanocortin receptor 4: their synthesis and biological evaluation in vitro," Journal of Medicinal Chemistry, vol. 44, pp. 3665-3672, (2001).
Bolin et al., "NMR structure of a minimized human agouti related protein prepared by total chemical synthesis," FEBS Letters, vol. 451, pp. 125-131, (1999).
Brash G., "From the agouti protein to POMC-100 years of fat blonde mice," Nat. Med., 5:984-985, (1999).
Brown et al., "The gene structure and minimal promoter of the human agouti related protein," Gene, vol. 277, pp. 231-238, (2001).

(Continued)

*Primary Examiner* — Laura L. Stockton
(74) *Attorney, Agent, or Firm* — Samuel B. Rollins

(57) ABSTRACT

Substituted aminothiazole derivatives, methods of their preparation, pharmaceutical compositions comprising a substituted aminothiazole, and methods of use in treating human or animal disorders. The compounds may be useful as inhibitors of action of AgRP on a melanocortin receptor and thus may be useful for the management, treatment, control, or the adjunct treatment of diseases which may be responsive to the modulation of melanocortin receptors including obesity-related disorders.

17 Claims, No Drawings

(56) References Cited

OTHER PUBLICATIONS

Bures et al., "Determination of disulfide structure in agouti-related protein (AgRP) by stepwise reduction and alkylation," Biochemistry, vol. 37, pp. 12172-12177, (1998).
Chai et al., "Inverse agonist activity of agouti and agouti-related protein," Peptides, vol. 24, pp. 603-609, (2003).
Claycombe et al., "Regulation of leptin by agouti," Physiological Genomics, vol. 2, pp. 101-105, (2000).
Cupples, "Peptides that regulate food intake," American Journal of Physiology, Regulatory, Integrative and Comparative Physiology, vol. 284, pp. R1370-R1374, (2003).
Dinulescu et al., "Agouti and agouti-related protein: analogies and contrast," The Journal of Biological Chemistry, vol. 275, pp. 6695-6698, (2000).
Edwards et al., "Cocaine- and amphetamine-regulated transcript, glucagon-like peptide-1 and corticotrophin releasing factor inhibit feeding via agouti-related protein independent pathways in the rat," Brain Research, vol. 866, pp. 128-134, (2000).
Fong et al., "ART (Protein product of agouti-related transcript) as an antagonist of MC-3 and MC-4 receptors," Biochemical and Biophysical Research Communications, vol. 237, pp. 629-631, (1997).
Hanada et al., "Differential Regulation of Melanin-concentrating hormone and orexin genes in the agouti-related protein/melanocortin-4 receptor system," Biochemical and Biophysical Research Communications, vol. 268, pp. 88-91, (2000).
Harrold et al., "Changes in hypothalamic agouti-related protein (AgRP), but not a-MSH or pro-opiomelanocortin concentrations in dietary-obese and food restricted rats," Biochemical and Biophysical Research Communications, vol. 258, pp. 574-577, (1999).
Haskell-Luevano et al., "Agouti-related protein functions as an inverse agonist at a constitutively active brain melanocortin-4 receptor," Regulatory Peptides, vol. 99, pp. 1-7, (2001).
Haskell-Luevano et al., "Structure activity studies of the melanocortin-4 receptor by in vitro Mutagenesis: identification of agouti-related protein (AgRP), Melanocortin agonist and synthetic peptide antagonist interaction determinants," Biochemistry, vol. 40, pp. 6164-6179, (2001).
Haskell-Luevano et al., "The agouti-related protein decapeptide (Yc[CRFFNAFC]Y) possesses agonist activity at the murine melanocortin-1 receptor," Peptides, vol. 21, pp. 683-689, (2000).
Hoggard et al., "Plasma concentrations of a-MSH, AgRP and leptin in lean and obese men and their relationship to differing states of energy balance perturbation," Clinical Endocrinology, vol. 61, pp. 31-39, (2004).
Hruby et al., "Design in topographical space of peptide and peptidomimetic chemist's glimpse at the mind—body problem," Accounts of Chemical Research, vol. 34, pp. 389-397, (2001).
Jackson et al., "Design, Pharmacology, and NMR structure of a minimized cystine knot with agouti-related protein activity," Biochemistry, vol. 24, pp. 7565-7572, (2002).
Joseph et al., "Chimeric NDP-MSH and MTII melanocortin peptides with agouti-related protein (AgRP) ArgPhe-Phe amino acids possess agonist melanocortin receptor activity," Peptides, vol. 24, pp. 1899-1908, (2003).
Kiefer et al., "Melanocortin receptor binding determinants in the agouti protein," Biochemistry, vol. 37, pp. 991-997, (1998).
Kiefer et al., "Mutations in the carboxyl terminus of the agouti protein decrease agouti inhibition of ligand binding to the melanocortin receptors," Biochemistry, vol. 36, pp. 2084-2090, (1997).
Kim et al., "Sustained orexigenic effect of agouti-related protein may be not mediated by the melanocortin 4 receptor," Peptides, vol. 23, 1069-1076, (2002).
Marsh et al., "Effects of Neuropeptide Y deficiency on hypothalamic agoUti-related protein expression and responsiveness to melanocortin analogues," Brain Research, vol. 848, pp. 66-77, (1999).

Mayfield et al., "A role for the agouti-related protein promoter in obesity and type 2 diabetes," Biochemical and Biophysical Research Communications, vol. 287, pp. 568-573, (2001).
McNulty et al., "High-resolution NMR structure of the chemically-synthesized melanocortin receptor binding domain AgRP(87-132) of the agouti-related protein," Biochemistry, vol. 40, pp. 15520-15527, (2001).
Navarro et al., "MTII-induced reduction of voluntary ethanol drinking is blocked by pretreatment with AgRP-(83-132)," Neuropeptides, vol. 37, pp. 338-344, (2003).
Qu et al., "Agouti-related protein is a mediator of diabetic hyperphagia," Regulatory Peptides, vol. 98, pp. 69-75, (2001).
Quillan et al., "A synthetic human agouti-related protein-(83-132)-NH2 fragment is a potent inhibitor of melanocortin receptor function," FEBS Letters, vol. 428, pp. 59-62, (1998).
Reizes et la., "Transgenic expression of Syndecan-1 uncovers a physiological control of feeding behavior by syndecan-3," Cell, vol. 106, pp. 105-116, (2001).
Rosenfeld et al., "Biochemical, biophysical, and pharmacological characterization of bacterially expressed human agouti-related protein," Biochemistry, vol. 37, pp. 16041-16052, (1998).
Takeuchi et al., "Widespread expression of agouti-related protein (AgRP) in the chicken: a possible involvement of AgRP in regulating peripheral melanocortin systems in the chicken," Biochimica et Biophysica Acta, vol. 1496, pp. 261-269, (2000).
Thirumoorthy et al., "Novel agouti-related-protein based melanocortin-1 receptor antagonist," Journal of Medicinal Chemistry, vol. 44, pp. 4114-4124, (2001).
Thompson et al., "Peptoid Mimics of agouti related protein," Bioorganic & Medicinal Chemistry Letters, vol. 13, pp. 1409-1413, (2003).
Tota et al., "Molecular interaction of agouti protein and agouti-related protein with human melanocortin receptors," Biochemistry, vol. 38, pp. 897-904, (1999).
Wilczynski et al., "Identification of putative agouti-related protein(87-132)-melanocortin-4 receptor interactions by homology molecular modeling and validation using chimeric peptide ligands," Journal of Medicinal Chemistry, vol. 47, pp. 2194-2207, (2004).
Wilczynski et al., "Structural characterization and pharmacology of a potent (Cys101-Cys119, Cys110-Cys117) bicyclic agouti-related protein (AgRP) melanocortin receptor," Journal of Medicinal Chemistry, vol. 47, pp. 5662-5673, (2004).
Wirth et al., "Agouti-related protein in the hypothalamic paraventricular nucleus: effect on feeding," Peptides, vol. 21, pp. 1369-1375, (2000).
Wirth et al., "Effect of agouti-related protein delivered to the dorsomedial nucleus of the hypothalamus on intake of a preferred versus a non-preferred diet," Brain Research, vol. 897, pp. 169-174, (2001).
Yang et al., "Effects of recombinant agouti-signaling protein on melanocortin action," Molecular Endocrinology, vol. 11, pp. 274-280, (1997).
Yang et al., "Molecular determinants of ligand binding to the human melanocortin-4 receptor," Biochemistry, vol. 39, pp. 14900-14911, (2000).
Yang et al., "Molecular determination of agouti-related protein binding to human melanocortin-4 receptor," Molecular Pharmacology, vol. 64, pp. 94-103, (2003).
Database Chemcats, Chemical Abstracts Service, Columbus, Ohio, retrieved from STN Order Numbers: Q-084349, Q-84359 abstract, "Ambinter Stock Screening Collection", Quai Louis Briot, (2004).
Database Beilstein, Beilstein Institute for Organic Chemistry, Frankfurt-Maine, Database accession No. BRN: 14989 abstract, Ukr. Khim.Zh et al., vol. 25, pp. 767-771, (1959).
Database Beilstein, Beilstein Institute for Organic Chemistry, Frankfurt-Maine, Database accession No. BRN: 7541410 abstract & Farmaco, vol. 51, No. 2, pp. 137-140, (1996).
Database Beilstein, Beilstein Institute for Organic Chemistry, Frankfurt-Maine, Database accession No. BRN: 678128 abstract & Eur. J. Med. Chem. Chim. Ther, vol. 9, p. 11, (1974).
Database Beilstein, Beilstein Institute for Organic Chemistry, Frankfurt-Maine, Database accession No. BRN: 309225 abstract & J. Am. Chem. Soc., vol. 63, p. 3028, (1941).

(56) References Cited

OTHER PUBLICATIONS

Database Beilstein, Beilstein Institute for Organic Chemistry, Frankfurt-Maine, Database accession No. BRN: 644518 abstract & Chem. Pharm. Bull., vol. 35, No. 12, pp. 4705-4710, (1987).
Database Beilstein, Beilstein Institute for Organic Chemistry, Frankfurt-Maine, Database accession No. BRN: 687549 abstract & Chem. Hetercycl. Compd., vol. 2, p. 1181, (1976).
Database Beilstein, Beilstein Institute for Organic Chemistry, Frankfurt-Maine, Database accession No. BRN: 294410 abstract & Justus Liebigs Ann. Chem., vol. 467, p. 254, (1928).
Database Beilstein, Beilstein Institute for Organic Chemistry, Frankfurt-Maine, Database accession No. BRN: 326592 abstract & J. Indian Chem. Soc., vol. 32, pp. 663-665, (1955).
Database Beilstein, Beilstein Institute for Organic Chemistry, Frankfurt-Maine, Database accession No. BRN: 2991 abstract & J. Am. Chem. Soc., vol. 72, p. 3138, (1950).
Database Beilstein, Beilstein Institute for Organic Chemistry, Frankfurt-Maine, Database accession No. BRN: 4957 abstract & Yakugaku Zasshi, vol. 71, p. 1439, (1951).
Database Beilstein, Beilstein Institute for Organic Chemistry, Frankfurt-Maine, Database accession No. BRN: 13161 abstract & Helv. Chim. Acta., vol. 31, p. 1142, (1946).
International Search Report for PCT application PCT/US2005/013386 mailed Aug. 26, 2005.
Written Opinion of the International Searching Authority, Patent Cooperation Treaty, International Application No. PCT/US2005/013386; International Filing Date Apr. 20, 2005.
Woods S.C., et al., "Signals that regulate food intake and energy homeostasis", *Science*, 280:1378-1383 (1998).
Flier J.S., et al., "Obesity and the hypothalamus: novel peptides for new pathways", *Cell*, 92:437-440 (1998).
Bultman SJ, et al., "Molecular characterization of the mouse agouti locus", *Cell*, 71:1195-1204 (1992).
Lu, D., et al., "Agouti protein is an antagonist of the melanocyte-stimulating-hormone receptor", *Nature*, 371:799-802 (1994).
Barsh G., "From the agouti protein to POMC-100 years of fat blonde mice", *Nat. Med.*, 5:984-985 (1999).
Ollmann, M.M., et al., "Antagonism of central melanocortin receptors in vitro and in vivo by agouti-related protein", *Science*, 278:135-138 (1997).
Adan Rah, et al., "Differential effects of melanocortin peptides on neural melanocortin receptors", *Mol Pharmacol.*, 46:1182-1190 (1994).
Schioth HB, et al., "The melanocortin 1,3,4 or 5 receptors do not have a binding epitope for ACTH beyond the sequence of α-MSH", *Endocrinology*, 155:73-78 (1997).
Mountjoy K.G., et al., "Localization of the melanocortin-4 receptor (MC-4R) in neuroendocrine and autonomic control circuits in the brain", *Mol Endocrinol.*, 8:1298-1308 (1994).
Huszar, D., et al., "Targeted disruption of the melanocortin-4 receptor results in obesity in mice", *Cell*, 88:131-141 (1997).
Krude, H., et al., "Severe early-onset obesity, adrenal insufficiency and red hair pigmentation caused by POMC mutations in humans", *Nat Genet.*, 19:155-157 (1998).
Yaswen L, et al., "Obesity in the mouse model of pro-opiomelanocortin deficiency responds to peripheral melanocortin", *Nat. Med.*, 5:1066-1070 (1999).
Benoit S.C., et al., "A novel selective melanocortin-4 receptor agonist reduces food intake in rats and mice without producing aversive consequences", *J Neurosci.*, 20:3442-3448 (2000).
Hinny, A., et al., "Several mutations in the melanocortin-4 receptor gene including a nonsense and a frameshift mutation associated with dominantly inherited obesity in humans", *J. Clin. Endocrinol. Metab.*, 84:1483-1486 (1999).
Gu, W., et al., "Identification and functional analysis of novel human melanocortin-4 receptor variants", *Diabetes*, 48:635-639 (1999).
International Preliminary Examination Report for PCT/US2009/054920, mailed Mar. 10, 2011.
International Search Report and Written Opinion for PCT/US2009/54920, mailed Oct. 28, 2009.
Dutia et al., "Effects of AgRP Inhibition on Energy Balance and Metabolism in Rodent Models," PLOS One 8(6)(e65317):1-17 (2013).

SUBSTITUTED AMINOTHIAZOLE DERIVATIVES, PHARMACEUTICAL COMPOSITIONS, AND METHODS OF USE

CROSS REFERENCE TO RELATED APPLICATIONS

The present application claims the benefit of priority under 35 U.S.C.§119 of U.S. Provisional Patent Application No. 61/092,844, filed Aug. 29, 2008, entitled "Substituted Aminothiazole Derivatives, Pharmaceutical Compositions, and Methods of Use", the entirety of which is herein incorporated by reference.

BACKGROUND OF THE INVENTION

1. Field of the Invention

This invention relates to substituted aminothiazole derivatives, pharmaceutical compositions, and methods of treatment using the compounds and pharmaceutical compositions which may be useful for the management, treatment, control, or adjunct treatment of diseases which may be responsive to the modulation of a melanocortin receptor.

2. Description of Related Art

The neuroendocrine regulation of homeostasis of body weight and energy expenditure is achieved by integrating peripheral hormonal signals such as leptin and insulin, and central signals generated from hypothalamic regions including the arcuate nucleus, mediobasal nucleus and paraventricular nucleus (Woods S. C., et al., 1998, "Signals that regulate food intake and energy homeostasis", *Science*, 280: 1378-1383; Flier J. S., et al., 1998, "Obesity and the hypothalamus: novel peptides for new pathways", *Cell*, 92:437-440).

Within the neuroendocrine regulatory pathway, the melanocortin system of the arcuate nucleus is of major importance. Melanocortin receptors (MC-R) have been identified in these hypothalamic regions. Pro-opiomelanocortin (POMC) containing neurons project to the arcuate nucleus to provide multiple neuropeptide neurotransmitters to stimulate these receptors. MC-Rs belong to the G-protein coupled receptor (GPCR) superfamily that contains a seven transmembrane structure. One unique characteristic that differentiates MC-Rs from other GPCRs is that endogenous antagonists/inverse agonists for these receptors have been discovered.

Striking evidence of endogenous antagonists/inverse agonists for MC-Rs has emerged from studies of the agouti protein, which exerts its effects through interacting with MC-R with competitive antagonism of the natural ligand alpha-MSH (Bultman S J, et al. 1992 "Molecular characterization of the mouse agouti locus", *Cell*, 71:1195-1204; Lu, D., et al., 1994, "Agouti protein is an antagonist of the melanocyte-stimulating-hormone receptor", *Nature*, 371:799-802; Brash G., 1999 "From the agouti protein to POMC-100 years of fat blonde mice", *Nat. Med.*, 5:984-985). The discovery of Agouti-related peptide (AgRP), an agouti protein homologue, that interacts specifically with subtypes of MC-Rs (MC-3R and MC-4R) and antagonizes MC-4R but not MC-1R further suggests that the central MC-R are involved in body weight regulation. (Ollmann, M. M., et al., 1997, "Antagonism of central melanocortin receptors in vitro and in vivo by agouti-related protein", *Science*, 278:135-138).

Five subtypes of MC-R (MC-1R-MC-5R) have been identified. Multiple POMC peptides are agonists on these receptors with overlapping activity (Adan Rah, et al., 1994, "Differential effects of melanocortin peptides on neural melanocortin receptors", *Mol Pharmacol.*, 46:1182-1190). MC-1R is primarily located in the peripheral nervous system. ACTH is the endogenous agonist for MC-2R, but is without much activity on other MC-R subtypes (Schioth H B, et al., 1997, "The melanocortin 1, 3, 4 or 5 receptors do not have a binding epitope for ACTH beyond the sequence of α-MSH", *Endocrinology*, 155:73-78). MC-3R and MC-4 and -5 are mainly located in the CNS, with high concentrations in the hypothalamic regions such as the arcuate nucleus and paraventricular nucleus (Mountjoy K. G., et al., 1994, "Localization of the melanocortin-4 receptor (MC-4R) in neuroendocrine and autonomic control circuits in the brain", *Mol Endocrinol.*, 8:1298-1308). Multiple lines of evidence indicate that hypothalamic MC-4R and MC-3R play a key role in regulating food intake and energy balance. Ectopically expressing Agouti peptide $A^{vy}$ mouse causes a lethal syndrome characterized by pronounced obesity and the development of diabetes and neoplasms (Lu, D., et al., 1994, "Agouti protein is an antagonist of the melanocyte stimulating-hormone receptor", *Nature*, 371:799-802). Transgenic mice over-expressing AgRP are obese, suggesting that blocking MC-3R or MC-4R is the cause of obesity. Further determination that MC-4R knock out mice (Brash, G., 1999 "From the agouti protein to POMC-100 years of fat blonde mice", *Nat Med.*, 5:984-985; Huszar, D., et al., 1997 "Targeted disruption of the melanocortin-4 receptor results in obesity in mice", *Cell*, 88:131-141) have a similar phenotype as that of AgRP over-expressing mice further confirms that MC-4R is a key component in the body weight regulation pathway whereas MC-3R seems to be more involved in energy regulation. Deficient synthesis of melanocortins causes obesity in human and mutant mice (Krude, H., et al., 1998, "Severe early-onset obesity, adrenal insufficiency and red hair pigmentation caused by POMC mutations in humans", *Nat Genet.*, 19:155-157; Yaswen L, et al., 1999, "Obesity in the mouse model of pro-opiomelanocortin deficiency responds to peripheral melanocortin", *Nat. Med.*, 5:1066-1070). Moreover, in animal models of obesity treatment with αMSH like agonist induced weight loss (Benoit S. C., et al., 2000, "A novel selective melanocortin-4 receptor agonist reduces food intake in rats and mice without producing aversive consequences", *J Neurosci.*, 20:3442-3448).

In humans, mutations of the MC-4R have been identified in obese patients and linked to impaired ligand binding and signaling (Hinney, A., et al., 1999, "Several mutations in the melanocortin-4 receptor gene including a nonsense and a frameshift mutation associated with dominantly inherited obesity in humans", *J. Clin. Endocrinol. Metab.*, 84:1483-1486; Gu, W., et al., 1999, "Identification and functional analysis of novel human melanocortin-4 receptor variants", *Diabetes*, 48:635-639; Krude, H., et al., 1998, "Severe early-onset obesity, adrenal insufficiency and red hair pigmentation caused by POMC mutations in humans", *Nat Genet.*, 19:155-157).

Aberrant regulation of body weight, such as that in obese patients, is associated with physiological and psychological disorders. Therefore, it is desirable to find drugs that can regulate central melanocortin system and therefore treat related medical disorders.

BRIEF SUMMARY OF THE INVENTION

This invention provides substituted aminothiazole derivatives and pharmaceutical compositions which modulate the functional interaction of AgRP (Agouti related protein) with a melanocortin receptor. In an embodiment, the present invention provides compounds of Formula (I) and pharmaceutically acceptable salts thereof as depicted below. In another embodiment, the present invention provides methods of preparation of compounds of Formula (I) and pharmaceutically acceptable salts thereof. In another embodiment, the present invention provides pharmaceutical compositions comprising a compound of Formula (I) or a pharmaceutically acceptable salt thereof. In another embodiment, the present invention provides methods of treatment comprising: administering to a subject a compound of Formula (I) or a pharmaceutically acceptable salt thereof.

The compounds of Formula (I) and pharmaceutically acceptable salts thereof are useful as modulators of AgRP interaction with a melanocortin receptor and thus may be useful for the management, treatment, control and adjunct treatment of diseases or conditions that may be responsive to the modulation of one or more melanocortin receptors. Such diseases or conditions may comprise bulimia and obesity including associated dyslipidemia and other obesity- and overweight-related complications such as, for example, cholesterol gallstones, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, Syndrome X, type II diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease. The compounds of Formula (I) and pharmaceutically acceptable salts thereof may also be useful for treating physiological disorders related to, for example, regulation of insulin sensitivity, inflammatory response, plasma triglycerides, HDL, LDL, and cholesterol levels and the like. The compounds of Formula (I) and pharmaceutically acceptable salts thereof may also be useful for treating female sexual dysfunction, male sexual dysfunction, and erectile dysfunction.

DETAILED DESCRIPTION OF THE INVENTION

Definitions

As used herein, the phrase "substituted aminothiazole derivatives" refers to the substituted aminothiazole derivatives of Formula (I) and pharmaceutically acceptable salts thereof.

In the compounds of Formula (I) or pharmaceutically acceptable salts thereof, the various functional groups represented should be understood to have a point of attachment at the functional group having the hyphen or asterisk. In other words, in the case of —$C_{1-6}$ alkylaryl, it should be understood that the point of attachment is the alkyl group; an example would be benzyl. In the case of a group such as —C(O)—NH—$C_{1-6}$ alkylaryl, the point of attachment is the carbonyl carbon.

As used herein the term "alkyl" refers to a straight or branched chain hydrocarbon having one to twelve carbon atoms, which may be substituted as herein further described, with multiple degrees of substitution being allowed. Examples of "alkyl" as used herein include, but are not limited to, methyl, ethyl, propyl, isopropyl, isobutyl, n-butyl, tert-butyl, isopentyl, and n-pentyl.

As used throughout this specification, the number of atoms, such as carbon atoms in an alkyl group, for example, will be represented by the phrase "$C_x$-$C_y$ alkyl," or "$C_{x-y}$ alkyl," which refer to an alkyl group, as herein defined, containing from x to y, inclusive, carbon atoms. Similar terminology will apply for other terms and ranges as well. One embodiment of the present invention includes so-called 'lower' alkyl chains of one to six carbon atoms. Thus, $C_1$-$C_6$ alkyl represents a lower alkyl chain as hereabove described.

As used herein, the term "cycloalkyl" refers to an optionally substituted non-aromatic, three- to twelve-membered, cyclic hydrocarbon ring, optionally containing one or more degrees of unsaturation, which may be substituted as herein further described, with multiple degrees of substitution being allowed. Exemplary "cycloalkyl" groups as used herein include, but are not limited to, cyclopropyl, cyclobutyl, cyclopentyl, cyclohexyl, and cycloheptyl, as well as rings containing one or more degrees of unsaturation but short of aromatic, such as cyclopropenyl, cyclobutenyl, cyclopentenyl, cyclohexenyl, and cycloheptenyl.

As used herein the term "halogen" refers to fluorine, chlorine, bromine, or iodine.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —$CF_3$.

When any variable occurs more than one time in any one constituent (e.g., $R^{50}$), or multiple constituents, its definition on each occurrence is independent at every other occurrence.

As used herein, the term "optionally" means that the subsequently described event(s) may or may not occur.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic administration to a patient.

As used herein, the phrase "one or more substituents" refers to a number of substituents that equals from one to the maximum number of substituents possible based on the number of available bonding sites, provided that the above conditions of stability and chemical feasibility are met.

As used herein, the term "prodrug" includes biohydrolyzable amides and biohydrolyzable esters and also encompasses a) compounds in which the biohydrolyzable functionality in such a prodrug is encompassed in the compound of Formula (I) or a pharmaceutically acceptable salt thereof: for example, an ester formed by a carboxylic group, and b) compounds which may be oxidized or reduced biologically at a given functional group to yield drug substances of Formula (I). Examples of these functional groups include, but are not limited to, 1,4-dihydropyridine, N-alkylcarbonyl-1,4-dihydropyridine, 1,4-cyclohexadiene, tert-butyl, and the like.

As used herein, the term "biohydrolyzable ester" is an ester of a drug substance (in this invention, a compound of Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester may be orally absorbed from the gut and transformed to (I) in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide may be orally absorbed from the gut and transformed to (I) in plasma. Many examples of such are known in the art and include by way of example lower alkyl amides, α-amino acid amides, alkoxyacyl amides, and alkylaminoalkylcarbonyl amides.

As used herein, "a subject" includes mammalian subjects such as, but not limited to, humans. In an embodiment, a subject is a human. In another embodiment, a subject is one who suffers from one or more of the aforesaid diseases, disease states, or conditions.

The term "female sexual dysfunction" refers to a failure or dysfunction in female arousal, desire, reception, or orgasm which is related to disturbances or abnormality in the function of any or all of the female sexual organs. Such disturbances or abnormalities may occur spontaneously or be a by-product of disease or treatment of disease, such as cancer or surgery to treat cancers, in particular cancer of the breast or cervix. In an embodiment, female sexual dysfunction may include female sexual arousal disorder (FSAD), desire disorders such as hypoactive sexual desire disorder (lack of interest in sex), and orgasmic disorders such as anorgasmia (unable to achieve orgasm).

The term "male sexual dysfunction" refers to a failure or dysfunction in male sexual function, which may involve impotence, erectile dysfunction, or loss of sexual desire.

The term "erectile dysfunction" refers to the failure of the male to achieve either erection and/or sexual function thereafter. "Erectile dysfunction" may be a by-product of factors such as but not limited to vascular disease, aging, surgery (particularly surgery involving organs of the male urogenital tract such as prostate), or diseases involving an imbalance of neurotransmitters or other biogenic amines or diseases involving the CNS such as depression.

The term "therapeutically effective amount" shall mean that amount of a drug or pharmaceutical agent that will elicit the therapeutic response of a subject that is being sought.

Compounds

Embodiments of the present invention comprise substituted aminothiazole derivatives, pharmaceutical compositions, and methods of use. The present invention may be embodied in a variety of ways.

In a first aspect, the present invention provides substituted aminothiazole derivatives as inhibitors of AgRP interaction with a melanocortin receptor which may be useful for the management and treatment of diseases and conditions that may be responsive to the modulation of one or more melanocortin receptors such as those associated obesity and obesity-related disorders.

In a first embodiment, the present invention provides a compound of Formula (I):

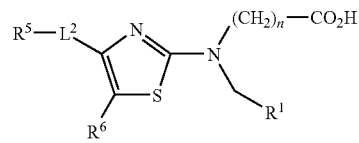

wherein n equals 1, 2 or 3;

$R^1$ is selected from the group consisting of:

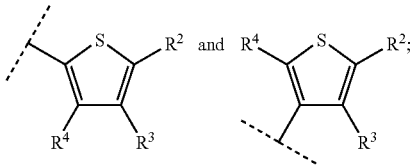

wherein $R^2$ is selected from the group consisting of: —$C_{1-4}$ alkyl and -$L^1$-$C_{1-4}$ alkyl, wherein $L^1$ is selected from the group consisting of —S—, and —$SO_2$—, $R^3$ is selected from the group consisting of: hydrogen and —$C_{1-4}$ alkyl, $R^4$ is selected from the group consisting of: hydrogen and —$C_{1-4}$ alkyl, wherein the alkyl groups in $R^2$, $R^3$, and $R^4$ are optionally substituted with one or more substituents independently selected from the group consisting of: fluoro and chloro;

$L^2$ is selected from the group consisting of: a direct bond or —$CH_2$—

$R^5$ is selected from the group consisting of:

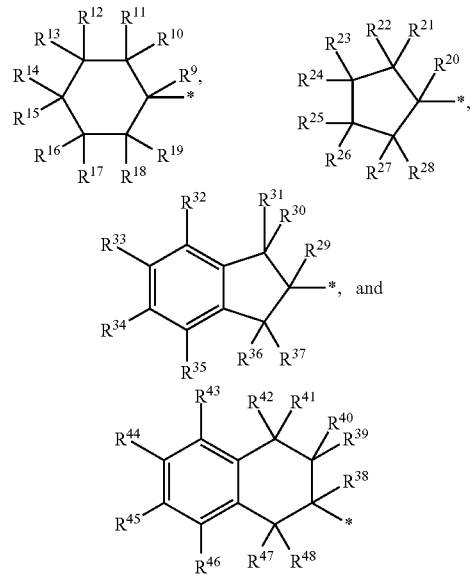

wherein
R$^9$, R$^{10}$, R$^{11}$, R$^{12}$, R$^{13}$, R$^{14}$, R$^{15}$, R$^{16}$, R$^{17}$, R$^{18}$ and R$^{19}$ are independently selected from the group consisting of: R$^a$, and
wherein
R$^{13}$ and R$^{14}$ may be taken together to be the group —[C(R$^{50}$)(R$^{51}$)]$_p$— wherein p is 3 or 4 and form a cyclopentyl or cyclohexyl ring bonded to the carbon atoms to which R$^{13}$ and R$^{14}$ are attached, or
R$^{14}$ and R$^{15}$ may be taken together to be the group —[C(R$^{50}$)(R$^{51}$)]$_q$— wherein q is 4 or 5 and form a cyclopentyl or cyclohexyl ring bonded to the carbon atom to which R$^{14}$ and R$^{15}$ are attached, or
R$^{13}$ and R$^{19}$ may be taken together to be the group —[C(R$^{50}$)(R$^{51}$)]$_r$— wherein r is 1 or 2 and form a cyclopentyl or cyclohexyl ring bonded to the carbon atoms to which R$^{13}$ and R$^{19}$ are attached,
wherein each R$^{50}$ and R$^{51}$ is independently selected from the group consisting of: R$^a$
R$^{20}$, R$^{21}$, R$^{22}$, R$^{23}$, R$^{24}$, R$^{25}$, R$^{26}$, R$^{27}$, and R$^{28}$ are independently selected from the group consisting of: R$^a$ and
wherein
R$^{24}$ and R$^{25}$ may be taken together to be the group —[C(R$^{54}$)(R$^{55}$)]$_p$— wherein p is 3 or 4 and form a cyclopentyl or cyclohexyl ring bonded to the carbon atoms to which R$^{24}$ and R$^{25}$ are attached,
wherein each R$^{54}$ and R$^{55}$ is independently selected from the group consisting of: R$^a$;
R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$ and R$^{48}$ are independently selected from the group consisting of: R$^a$;
R$^6$ is selected from the group consisting of: hydrogen, and methyl, wherein the methyl group is optionally substituted with one or more substituents independently selected from the group consisting of a halogen group;
wherein
R$^a$ is selected from the group consisting of: -hydrogen, -halogen, —C$_{1-6}$ alkyl, -phenyl, cycloalkyl, and —O—C$_{1-6}$ alkyl,
wherein the alkyl, cycloalkyl, and phenyl groups are optionally substituted with one or more substituents independently selected from R$^b$;
R$^b$ is selected from the group consisting of: halogen, —C$_{1-6}$ alkyl, and -halo-C$_{1-4}$ alkyl; or a pharmaceutically acceptable salt thereof.

Embodiment 2

A compound according to embodiment 1, wherein n is 1.

Embodiment 3

A compound according to embodiment 1, wherein n is 2.

Embodiment 4

A compound according to embodiment 1, wherein n is 3.

Embodiment 5

A compound according to any one of the previous embodiments, wherein
R$^1$ is

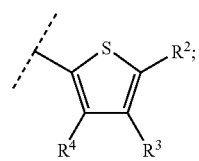

wherein
R$^2$ is selected from the group consisting of: —C$_{1-4}$ alkyl and -L$^1$-C$_{1-4}$ alkyl, wherein L$^1$ is selected from the group consisting of —S—, and —SO$_2$—,
R$^3$ is selected from the group consisting of: hydrogen and —C$_{1-4}$ alkyl,
R$^4$ is selected from the group consisting of: hydrogen and —C$_{1-4}$ alkyl, wherein the alkyl groups in R$^2$, R$^3$, and R$^4$ are optionally substituted with one or more substituents independently selected from the group consisting of: fluoro and chloro.

Embodiment 6

A compound according to embodiment 5, wherein R$^3$ is hydrogen.

Embodiment 7

A compound according to embodiment 5, wherein R$^3$ is selected from the group consisting of: methyl, ethyl, propyl, and isopropyl, wherein the methyl, ethyl, propyl, and isopropyl groups are optionally substituted with one or more substituents independently selected from the group consisting of: fluoro and chloro.

Embodiment 8

A compound according to embodiment 7, wherein R$^3$ is selected from the group consisting of: methyl and ethyl.

Embodiment 9

A compound according to any one of embodiments 5 to 8, wherein R$^4$ is hydrogen.

Embodiment 10

A compound according to any one of embodiments 5 to 8, wherein R$^4$ is selected from the group consisting of: methyl, ethyl, propyl, and isopropyl, wherein the methyl, ethyl, propyl, and isopropyl groups are optionally substituted with one or more substituents independently selected from the group consisting of: fluoro and chloro.

Embodiment 11

A compound according to embodiment 10, wherein R$^4$ is selected from the group consisting of: methyl and ethyl.

Embodiment 12

A compound according to any one of embodiments 5 to 11, wherein R$^2$ is selected from the group consisting of: methyl, ethyl, propyl, and isopropyl, wherein the methyl, ethyl, propyl, and isopropyl groups are optionally substituted with one or more substituents independently selected from the group consisting of: fluoro and chloro.

Embodiment 13

A compound according to embodiment 12, wherein R$^2$ is methyl.

Embodiment 14

A compound according to embodiment 12, wherein $R^2$ is ethyl.

Embodiment 15

A compound according to any one of embodiments 5 to 11, wherein $R^2$ is $-L^1-C_{1-4}$ alkyl, wherein $L^1$ is selected from the group consisting of —S— and —SO$_2$—.

Embodiment 16

A compound according to embodiment 15, wherein $R^2$ is $-L_1-CH_3$.

Embodiment 17

A compound according to any one of embodiments 1 to 4, wherein $R^1$ is

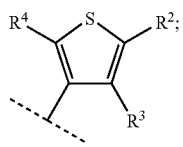

wherein
  $R^2$ is selected from the group consisting of: —$C_{1-4}$ alkyl and -$L^1-C_{1-4}$alkyl, wherein $L^1$ is selected from the group consisting of —S—, and —SO$_2$—,
  $R^3$ is selected from the group consisting of: hydrogen and —$C_{1-4}$ alkyl,
  $R^4$ is selected from the group consisting of: hydrogen and —$C_{1-4}$ alkyl, wherein the alkyl groups in $R^2$, $R^3$, and $R^4$ are optionally substituted with one or more substituents independently selected from the group consisting of: fluoro and chloro.

Embodiment 18

A compound according to embodiment 17, wherein $R^3$ is hydrogen.

Embodiment 19

A compound according to embodiment 17, wherein $R^3$ is selected from the group consisting of: methyl, ethyl, propyl, and isopropyl, wherein the methyl, ethyl, propyl, and isopropyl groups are optionally substituted with one or more substituents independently selected from the group consisting of: fluoro and chloro.

Embodiment 20

A compound according to embodiment 19, wherein $R^3$ is selected from the group consisting of: methyl and ethyl.

Embodiment 21

A compound according to any one of embodiments 17 to 20, wherein $R^4$ is hydrogen.

Embodiment 22

A compound according to any one of embodiments 17 to 20, wherein $R^4$ is selected from the group consisting of: methyl, ethyl, propyl, and isopropyl, wherein the methyl, ethyl, propyl, and isopropyl groups are optionally substituted with one or more substituents independently selected from the group consisting of: fluoro and chloro.

Embodiment 23

A compound according to embodiment 22, wherein $R^4$ is selected from the group consisting of: methyl and ethyl.

Embodiment 24

A compound according to any one of embodiments 17 to 23, wherein $R^2$ is selected from the group consisting of: methyl, ethyl, propyl, and isopropyl, wherein the methyl, ethyl, propyl, and isopropyl groups are optionally substituted with one or more substituents independently selected from the group consisting of: fluoro and chloro.

Embodiment 25

A compound according to embodiment 24, wherein $R^2$ is methyl.

Embodiment 26

A compound according to embodiment 24, wherein $R^2$ is ethyl.

Embodiment 27

A compound according to any one of embodiments 17 to 23, wherein $R^2$ is -$L^1-C_{1-4}$ alkyl, wherein $L^1$ is selected from the group consisting of —S— and —SO$_2$—.

Embodiment 28

A compound according to embodiment 27, wherein $R^2$ is -$L^1-CH_3$.

Embodiment 29

A compound according to any one of the previous embodiments, wherein $L^2$ is a direct bond.

Embodiment 30

A compound according to any one of the previous embodiments, wherein $L^2$ is —CH$_2$—.

Embodiment 31

A compound according to any one of the previous embodiments, wherein $R^5$ is

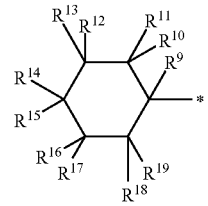

wherein
$R^9$, $R^{10}$, $R^{11}$, $R^{12}$, $R^{13}$, $R^{14}$, $R^{15}$, $R^{16}$, $R^{17}$, $R^{18}$ and $R^{19}$ are independently selected from the group consisting of: $R^a$, and wherein
$R^{13}$ and $R^{14}$ may be taken together to be the group —[C($R^{50}$)($R^{51}$)]$_p$— wherein p is 3 or 4 and form a cyclopentyl or cyclohexyl ring bonded to the carbon atoms to which $R^{13}$ and $R^{14}$ are attached, or $R^{14}$ and $R^{15}$ may be taken together to be the group —[C($R^{50}$)($R^{51}$)]$_q$— wherein q is 4 or 5 and form a cyclopentyl or cyclohexyl ring bonded to the carbon atom to which $R^{14}$ and $R^{15}$ are attached, or $R^{13}$ and $R^{19}$ may be taken together to be the group —[C($R^{50}$)($R^{51}$)]$_r$— wherein r is 1 or 2 and form a cyclopentyl or cyclohexyl ring bonded to the carbon atoms to which $R^{13}$ and $R^{19}$ are attached, wherein each $R^{50}$ and $R^{51}$ is independently selected from the group consisting of: $R^a$.

Embodiment 32

A compound according to embodiment 31, wherein $R^9$, $R^{10}$, $R^{11}$, $R^{12}$, $R^{13}$, $R^{14}$, $R^{15}$, $R^{16}$, $R^{17}$, $R^{18}$ and $R^{19}$ are independently selected from the group consisting of: $R^a$ Embodiment 33

A compound according to embodiment 32, wherein $R^9$, $R^{10}$, $R^{11}$, $R^{14}$, $R^{15}$, $R^{18}$, and $R^{19}$ are hydrogen, and $R^{12}$, $R^{13}$, $R^{16}$, and $R^{17}$ are independently selected from the group consisting of: hydrogen and $C_{1-4}$ alkyl, wherein the alkyl group is optionally substituted one or more times with halogen.

Embodiment 34

A compound according to embodiment 32, wherein $R^{10}$, $R^{11}$, $R^{12}$, $R^{13}$, $R^{16}$, $R^{17}$, $R^{18}$ and $R^{19}$ are hydrogen, and $R^9$, $R^{14}$, and $R^{15}$ are independently selected from the group consisting of: $R^a$, wherein at least one of $R^9$, $R^{14}$, and $R^{15}$ is not hydrogen.

Embodiment 35

A compound according to embodiment 34, wherein $R^{10}$, $R^{11}$, $R^{12}$, $R^{13}$, $R^{16}$, $R^{17}$, $R^{18}$ and $R^{19}$ are hydrogen, $R^9$ is selected from the group consisting of: —$C_{1-4}$ alkyl and -phenyl, wherein the phenyl group is optionally substituted one or more times with a substituent independently selected from the group consisting of: -halogen, —$C_{1-6}$ alkyl, and -halo-$C_{1-4}$ alkyl, and
$R^{14}$ and $R^{15}$ are independently selected from the group consisting of: hydrogen, $C_{1-6}$ alkyl, and phenyl.

Embodiment 36

A compound according to embodiment 34, wherein $R^9$, $R^{10}$, $R^{11}$, $R^{12}$, $R^{13}$, $R^{16}$, $R^{17}$, $R^{18}$ and $R^{19}$ are hydrogen, and
$R^{14}$ and $R^{15}$ are independently selected from the group consisting of: $R^a$, wherein at least one of $R^{14}$ and $R^{15}$ is not hydrogen.

Embodiment 37

A compound according to embodiment 36, wherein $R^{14}$ and $R^{15}$ are both either fluoro or —$C_{1-4}$ alkyl.

Embodiment 38

A compound according to embodiment 36, wherein $R^{14}$ is hydrogen, and
$R^{15}$ is selected from the group consisting of: -halogen, —$C_{1-6}$ alkyl, -phenyl, —$C_{5-6}$ cycloalkyl, and —O—$C_{1-16}$ alkyl, wherein the alkyl, cycloalkyl, and phenyl groups are optionally substituted one or more times with a group independently selected from $R^b$.

Embodiment 39

A compound according to embodiment 38, wherein $R^{15}$ is selected from the group consisting of: -methyl, -ethyl, -propyl, -isopropyl, -tert-butyl, -trifluoromethyl, -cyclohexyl, and phenyl, wherein the phenyl group is optionally substituted one or more times with a group independently selected from $R^b$.

Embodiment 40

A compound according to embodiment 38, wherein $R^{15}$ is selected from the group consisting of: -methyl, -ethyl, -propyl, -isopropyl, and -tert-butyl.

Embodiment 41

A compound according to embodiment 32, wherein $R^9$, $R^{10}$, $R^{11}$, $R^{12}$, $R^{13}$, $R^{14}$, $R^{15}$, $R^{16}$, $R^{17}$, $R^{18}$ and $R^{19}$ are hydrogen.

Embodiment 42

A compound according to embodiment 31, wherein
$R^9$, $R^{10}$, $R^{11}$, $R^{12}$, $R^{15}$, $R^{16}$, $R^{17}$, $R^{18}$ and $R^{19}$ are independently selected from the group consisting of: $R^a$, and
$R^{13}$ and $R^{14}$ are taken together to be the group —[C($R^{50}$)($R^{51}$)]$_p$— wherein p is 3 or 4 and form a cyclopentyl or cyclohexyl ring bonded to the carbon atoms to which $R^{13}$ and $R^{14}$ are attached,
wherein each $R^{50}$ and $R^{51}$ is independently selected from the group consisting of: $R^a$.

Embodiment 43

A compound according to embodiment 42, wherein $R^9$, $R^{10}$, $R^{11}$, $R^{12}$, $R^{15}$, $R^{16}$, $R^{17}$, $R^{18}$ and $R^{19}$ are hydrogen, and
$R^{13}$ and $R^{14}$ are taken together to be the group —[CH$_2$]$_p$— wherein p is 3 or 4 and form a cyclopentyl or cyclohexyl ring bonded to the carbon atoms to which $R^{13}$ and $R^{14}$ are attached.

Embodiment 44

A compound according to embodiment 31, wherein $R^9$, $R^{10}$, $R^{11}$, $R^{12}$, $R^{13}$, $R^{16}$, $R^{17}$, $R^{18}$ and $R^{19}$ are independently selected from the group consisting of: $R^a$, and
$R^{14}$ and $R^{15}$ are taken together to be the group —[C($R^{50}$)($R^{51}$)]$_q$— wherein q is 4 or 5 and form a cyclopentyl or cyclohexyl ring bonded to the carbon atom to which $R^{14}$ and $R^{15}$ are attached,
wherein each $R^{50}$ and $R^{51}$ is independently selected from the group consisting of: $R^a$.

Embodiment 45

A compound according to embodiment 44, wherein
$R^9$, $R^{10}$, $R^{11}$, $R^{12}$, $R^{13}$, $R^{16}$, $R^{17}$, $R^{18}$ and $R^{19}$ are hydrogen, and
$R^{14}$ and $R^{15}$ are taken together to be the group —$[CH_2]_q$— wherein q is 4 or 5 and form a cyclopentyl or cyclohexyl ring bonded to the carbon atom to which $R^{14}$ and $R^{15}$ are attached.

Embodiment 46

A compound according to embodiment 31, wherein
$R^9$, $R^{10}$, $R^{11}$, $R^{12}$, $R^{14}$, $R^{15}$, $R^{16}$, $R^{17}$ and $R^{18}$ are independently selected from the group consisting of: $R^a$, and
$R^{13}$ and $R^{19}$ are taken together to be the group —$[C(R^{50})(R^{51})]_r$— wherein r is 1 or 2 and form a cyclopentyl or cyclohexyl ring bonded to the carbon atoms to which $R^{13}$ and $R^{19}$ are attached,
wherein each $R^{50}$ and $R^{51}$ is independently selected from the group consisting of: $R^a$.

Embodiment 47

A compound according to embodiment 46, wherein
$R^9$, $R^{10}$, $R^{11}$, $R^{12}$, $R^{14}$, $R^{15}$, $R^{16}$, $R^{17}$ and $R^{18}$ are hydrogen, and
$R^{13}$ and $R^{19}$ are taken together to be the group —$[CH_2]_r$— wherein r is 1 or 2 to form a cyclopentyl or cyclohexyl ring bonded to the carbon atoms to which $R^{13}$ and $R^{19}$ are attached.

Embodiment 48

A compound according to any one of embodiments 1 to 30, wherein
$R^5$ is

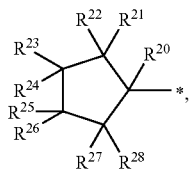

wherein
$R^{20}$, $R^{21}$, $R^{22}$, $R^{23}$, $R^{24}$, $R^{25}$, $R^{26}$, $R^{27}$, and $R^{28}$ are independently selected from the group consisting of: $R^a$ and
wherein
$R^{24}$ and $R^{25}$ may be taken together to be the group —$[C(R^{54})(R^{55})]_p$— wherein p is 3 or 4 and form a cyclopentyl or cyclohexyl ring bonded to the carbon atoms to which $R^{24}$ and $R^{25}$ are attached,
wherein each $R^{54}$ and $R^{55}$ is independently selected from the group consisting of: $R^a$.

Embodiment 49

A compound according to embodiment 48, wherein
$R^{20}$, $R^{21}$, $R^{22}$, $R^{23}$, $R^{24}$, $R^{25}$, $R^{26}$, $R^{27}$, and $R^{28}$ are hydrogen.

Embodiment 50

A compound according to embodiment 48, wherein
$R^{20}$, $R^{21}$, $R^{22}$, $R^{23}$, $R^{24}$, $R^{25}$, $R^{26}$, $R^{27}$, and $R^{28}$ are independently selected from the group consisting of: $R^a$, wherein at least one of $R^{20}$, $R^{21}$, $R^{22}$, $R^{23}$, $R^{24}$, $R^{25}$, $R^{26}$, $R^{27}$, and $R^{28}$ is not hydrogen.

Embodiment 51

A compound according to embodiment 50, wherein
$R^{20}$ is selected from the group consisting of: —$C_{1-6}$ alkyl, and -phenyl, wherein the alkyl and phenyl groups may be substituted one or more times with a group independently selected from $R^b$.

Embodiment 52

A compound according to embodiment 51, wherein
$R^{20}$ is selected from the group consisting of: -isobutyl and -phenyl, wherein the phenyl group is substituted once with a group selected from halogen and methyl.

Embodiment 53

A compound according to any one of embodiments 50 to 52, wherein
$R^{21}$, $R^{22}$, $R^{23}$, $R^{24}$, $R^{25}$, $R^{26}$, $R^{27}$, and $R^{28}$ are hydrogen.

Embodiment 54

A compound according to any one of embodiments 1 to 30, wherein $R^5$ is

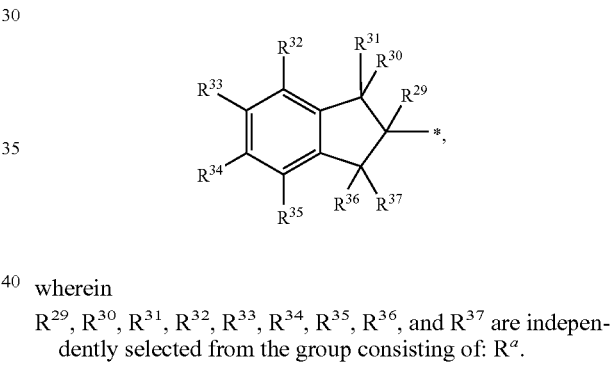

wherein
$R^{29}$, $R^{30}$, $R^{31}$, $R^{32}$, $R^{33}$, $R^{34}$, $R^{35}$, $R^{36}$, and $R^{37}$ are independently selected from the group consisting of: $R^a$.

Embodiment 55

A compound according to embodiment 54, wherein $R^{29}$, $R^{30}$, $R^{31}$, $R^{32}$, $R^{33}$, $R^{34}$, $R^{35}$, $R^{36}$, and $R^{37}$ are hydrogen.

Embodiment 56

A compound according to embodiment 54, wherein $R^{29}$, $R^{30}$, $R^{31}$, $R^{32}$, $R^{33}$, $R^{34}$, $R^{35}$, $R^{36}$ and $R^{37}$ are independently selected from the group consisting of: $R^a$, wherein at least one of $R^{29}$, $R^{30}$, $R^{31}$, $R^{32}$, $R^{33}$, $R^{34}$, $R^{35}$, $R^{36}$ and $R^{37}$ is not hydrogen.

Embodiment 57

A compound according to embodiment 56, wherein $R^{29}$, $R^{30}$, $R^{31}$, $R^{32}$, $R^{33}$, $R^{34}$, $R^{35}$, $R^{36}$ and $R^{37}$ are independently selected from the group consisting of: hydrogen and —$C_{1-4}$ alkyl, wherein the alkyl group is optionally substituted one or more times with halogen, and wherein at least one of $R^{29}$, $R^{30}$, $R^{31}$, $R^{32}$, $R^{33}$, $R^{34}$, $R^{35}$, $R^{36}$ and $R^{37}$ is not hydrogen.

Embodiment 58

A compound according to any one of embodiments 1 to 30, wherein $R^5$ is

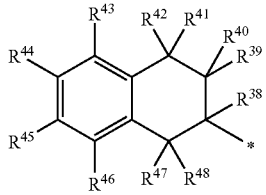

wherein
$R^{38}$, $R^{39}$, $R^{40}$, $R^{41}$, $R^{42}$, $R^{43}$, $R^{44}$, $R^{45}$, $R^{46}$, $R^{47}$ and $R^{48}$ are independently selected from the group consisting of: $R^a$.

Embodiment 59

A compound according to embodiment 58, wherein $R^{38}$, $R^{39}$, $R^{40}$, $R^{41}$, $R^{42}$, $R^{43}$, $R^{44}$, $R^{45}$, $R^{46}$, $R^{47}$ and $R^{48}$ are hydrogen.

Embodiment 60

A compound according to embodiment 58, wherein $R^{38}$, $R^{39}$, $R^{40}$, $R^{41}$, $R^{42}$, $R^{43}$, $R^{44}$, $R^{45}$, $R^{46}$, $R^{47}$ and $R^{48}$ are independently selected from the group consisting of: $R^a$, wherein at least one of $R^{29}$, $R^{30}$, $R^{31}$, $R^{32}$, $R^{33}$, $R^{34}$, $R^{35}$, $R^{36}$ is not hydrogen.

Embodiment 61

A compound according to embodiment 60, wherein $R^{38}$, $R^{39}$, $R^{40}$, $R^{41}$, $R^{42}$, $R^{43}$, $R^{44}$, $R^{45}$, $R^{46}$, $R^{47}$ and $R^{48}$ are independently selected from the group consisting of: hydrogen and —$C_{1-4}$ alkyl, wherein the alkyl group is optionally substituted one or more times with halogen, and wherein at least one of $R^{38}$, $R^{39}$, $R^{40}$, $R^{41}$, $R^{42}$, $R^{43}$, $R^{44}$, $R^{45}$, $R^{46}$, $R^{47}$ and $R^{48}$ is not hydrogen.

Embodiment 62

A compound according to any one of embodiments 1 to 30, wherein
$R^6$ is selected from the group consisting of: hydrogen, methyl, wherein the methyl group may be substituted one or more times with a halogen group.

Embodiment 63

A compound according to embodiment 62, wherein $R^6$ is hydrogen.

Embodiment 64

A compound according to embodiment 62, wherein $R^6$ is methyl.

Embodiment 65

A compound according to embodiment 1, wherein
n is 2;
$R_1$ is selected from the group consisting of:

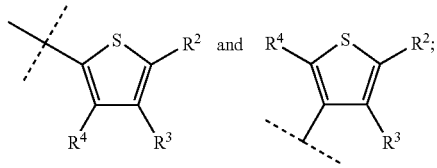

wherein
$R^2$ is selected from the group consisting of: —$C_{1-4}$ alkyl and -$L^1$-$C_{1-4}$ alkyl, wherein $L^1$ is selected from the group consisting of —S—, and —$SO_2$—,
$R^3$ is selected from the group consisting of: hydrogen and —$C_{1-4}$ alkyl,
$R^4$ is selected from the group consisting of: hydrogen and —$C_{1-4}$ alkyl,
wherein the alkyl groups in $R^2$, $R^3$, and $R^4$ are optionally substituted with one or more substituents independently selected from the group consisting of: fluoro and chloro;
$L^2$ is selected from the group consisting of: a direct bond or —$CH_2$—;
$R^5$ is selected from the group consisting of:

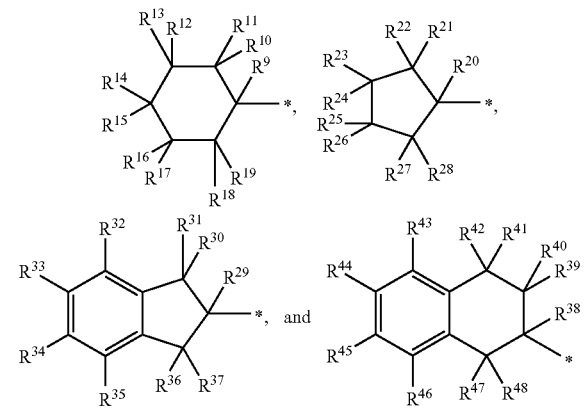

wherein
$R^9$, $R^{10}$, $R^{11}$, $R^{12}$, $R^{13}$, $R^{14}$, $R^{15}$, $R^{16}$, $R^{17}$, $R^{18}$ and $R^{19}$ are independently selected from the group consisting of: $R^a$;
$R^{20}$, $R^{21}$, $R^{22}$, $R^{23}$, $R^{24}$, $R^{25}$, $R^{26}$, $R^{27}$ and $R^{28}$ are independently selected from the group consisting of: $R^a$;
$R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$ are independently selected from the group consisting of: $R^a$;
$R^6$ is selected from the group consisting of: hydrogen and methyl;
wherein
$R^a$ is selected from the group consisting of: -hydrogen, —$C_{1-6}$ alkyl, -phenyl, and -cycloalkyl,
wherein the alkyl, cycloalkyl, and phenyl groups are optionally substituted with one or more substituents independently selected from $R^b$;
$R^b$ is selected from the group consisting of: halogen, —$C_{1-6}$ alkyl, and -halo-$C_{1-4}$ alkyl.

Embodiment 66

A compound according to embodiment 1, wherein
n is 2;
$R^1$ is selected from the group consisting of:

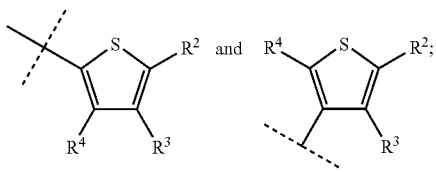

wherein
$R^2$ is selected from the group consisting of: —$C_{1-4}$ alkyl,
$R^3$ is selected from the group consisting of: hydrogen and —$C_{1-4}$ alkyl,
$R^4$ is selected from the group consisting of: hydrogen and —$C_{1-4}$ alkyl;
$L^2$ is a direct bond;
$R_5$ is

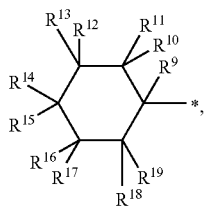

wherein
$R^9, R^{10}, R^{11}, R^{12}, R^{13}, R^{16}, R^{17}, R^{18}$ and $R^{19}$ are hydrogen;
$R^{14}$ and $R^{15}$ are independently selected from the group consisting of: $R^a$, wherein at least one of $R^{14}$ and $R^{15}$ is not hydrogen;
$R_6$ is hydrogen;
wherein
$R^a$ is selected from the group consisting of: -hydrogen, —$C_{1-6}$ alkyl, -phenyl, and -cyclohexyl,
wherein the alkyl, cyclohexyl, and phenyl groups are optionally substituted with one or more substituents independently selected from $R^b$; and
$R^b$ is selected from the group consisting of: —$C_{1-6}$ alkyl.

Embodiment 67

A compound according to embodiment 1, wherein
n is 2;
$R_1$ is

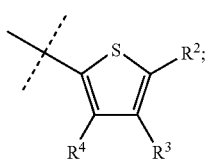

wherein
$R^2$ is selected from the group consisting of: ethyl and methyl,
$R^3$ and $R^4$ are hydrogen;
$L^2$ is a direct bond;
$R_5$ is

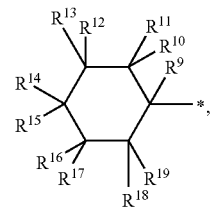

wherein
$R^9, R^{10}, R^{11}, R^{12}, R^{13}, R^{14}, R^{16}, R^{17}, R^{18}$ and $R^{19}$ are hydrogen;
$R^{15}$ is selected from the group consisting of: tert-butyl, isopropyl, and phenyl; and
$R_6$ is hydrogen.

Embodiment 68

A compound according to embodiment 67, wherein $R^2$ is methyl.

Embodiment 69

A compound according to any one of the previous embodiments, wherein the compound of Formula (I) is in the form of a hydrochloride salt.

Embodiment 70

A compound according to any one of the previous embodiments, wherein the compound of Formula (I) is in the form of a sodium salt.

Also included within the scope of the invention are the individual enantiomers of the compounds represented by Formula (I) above as well as any wholly or partially racemic mixtures thereof. Also, included within the scope of the present invention are all stereoisomers, geometric isomers and tautomeric forms of the compounds of formula (I), including compounds exhibiting more than one type of isomerism, and mixtures of one or more thereof. Also included are acid addition salts wherein the counterion is optically active, for example, d-lactate or racemic, for example, dl-tartrate.

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

In another aspect, the present invention provides a prodrug of compounds of Formula (I) or a pharmaceutically acceptable salt thereof. In an embodiment, the prodrug comprises a biohydrolyzable ester or biohydrolyzable amide of a compound of Formula (I) or a pharmaceutically acceptable salt thereof.

Examples of compounds of Formula (I) or pharmaceutically acceptable salts thereof having useful biological activity are listed the Examples section. The ability of compounds of Formula (I) or pharmaceutically acceptable salts thereof to inhibit AgRP interaction with MC-4R was established using the Biological Assay described below. The compounds of the Examples 1-64 showed an increase in cAMP production in this Assay and possess an effective concentration for half maximal effect (EC50) in the assay of less than 5 µM.

Compounds that inhibit AgRP functional interaction with a melanocortin receptor are potentially useful in treating diseases or conditions that may be responsive to the modulation of melanocortin receptors. The compounds of Formula (I) or pharmaceutically acceptable salts thereof may therefore be useful in the treatment of obesity and obesity-related disorders.

In another aspect, the present invention comprises a pharmaceutical composition comprising the compound of Formula (I) or a pharmaceutically acceptable salt thereof. In an embodiment, the pharmaceutical composition further comprises a pharmaceutically acceptable carrier, excipient, diluent, or mixture thereof.

The compounds of Formula (I) and pharmaceutically acceptable salts thereof may be useful for the treatment of bulimia and obesity including associated dyslipidemia and other obesity- and overweight-related complications such as, for example, cholesterol gallstones, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, Syndrome X, type II diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease. The compounds of Formula (I) and pharmaceutically acceptable salts thereof may also be useful for treating physiological disorders related to, for example, regulation of insulin sensitivity, inflammatory response, plasma triglycerides, HDL, LDL, and cholesterol levels and the like. The compounds of Formula (I) and pharmaceutically acceptable salts thereof may also be useful for treating female sexual dysfunction, male sexual dysfunction, and erectile dysfunction. These conditions may be treated by modulating the functional interaction of AgRP on a melanocortin receptor.

Thus in another aspect, the present invention provides pharmaceutical compositions and methods of treatment.

In an embodiment, the pharmaceutical compositions containing a compound of Formula (I) or a pharmaceutically acceptable salt thereof may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

In another embodiment, formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

In another embodiment, the composition may comprise an aqueous suspension. Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Also, oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

In another embodiment, the pharmaceutical compositions of the present invention may comprise a syrup or elixir. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The pharmaceutical compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

In an embodiment, for topical use, creams, ointments, jellies, solutions of suspensions, etc., containing the compounds of the invention may be employed. For the purpose of this application, topical applications shall include mouth washes and gargles.

In an embodiment, the compounds of Formula (I) and pharmaceutically acceptable salts thereof may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Pharmaceutically-acceptable salts of compounds of Formula (I), where a basic or acidic group is present in the structure, are also included within the scope of the invention. The term "pharmaceutically acceptable salts" refers to salts of the compounds of this invention which are not biologically or otherwise undesirable and which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartrate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

In an embodiment, the present invention provides a pharmaceutical formulation comprising a hydrochloric acidic salt of a compound of Formula (I).

In another embodiment, the present invention provides a pharmaceutical formulation comprising a sodium salt of a compound of Formula (I).

Other salts which are not pharmaceutically acceptable may be useful in the preparation of compounds of the invention and these form a further aspect of the invention.

Thus, in a further embodiment, there is provided a pharmaceutical composition comprising a compound of Formula (I) or pharmaceutically acceptable salts thereof, or a prodrug thereof and one or more pharmaceutically acceptable carriers, excipients, or diluents.

In another embodiment, the present invention provides a pharmaceutical composition comprising a compound of Formula (I) or a pharmaceutically acceptable salt thereof, in combination with a pharmaceutically acceptable carrier and one or more hypoglycemic agents. Hypoglycemic agents may include, but are not limited to, insulin or insulin mimetics; biguanidines such as metformin or buformin; PTP-1B inhibitors; PPAR-gamma agonists; sulfonylureas such as acetohexamide, chloropropamide, tolazamide, tolbutamide, glyburide, glipizide, glyciazide; or any other insulin secretagogue such as, for example, repaglinide and nateglinide; or α-glycosidase inhibitors such as acarbose, voglibose, or miglitol; or $\beta_3$-adrenoceptor agonists.

In another embodiment, the present invention provides a pharmaceutical composition comprising a compound of Formula (I), or a pharmaceutically acceptable salt thereof, in combination with a pharmaceutically acceptable carrier and HMG Co-A reductase inhibitors (statins), bile acid sequestrants, fibrates such as fenofibrate, cholesterol lowering agents, inhibitors of cholesterol absorption such as ACAT inhibitors, bile acid transport inhibitors, CETP inhibitors, or other antihyperlipidemic agents to improve the lipid profile of a subject.

In another embodiment, the present invention provides a pharmaceutical composition comprising a compound of Formula (I), or a pharmaceutically acceptable salt thereof, in combination with a pharmaceutically acceptable carrier and one or more agents selected from the group consisting of agents that modulate thermogenesis, lipolysis, gut motility, fat absorption, and satiety.

In another embodiment, the present invention provides a pharmaceutical composition comprising a compound of Formula (I), or a pharmaceutically acceptable salt thereof, in combination with a pharmaceutically acceptable carrier and one or more agents selected from the group consisting of agents that regulate hypertension (e.g., inhibitors of angiotensin converting enzyme (ACE), β-blockers, calcium channel blockers).

In another embodiment, the present invention provides a pharmaceutical composition comprising a compound of Formula (I), or a pharmaceutically acceptable salt thereof, in combination with a pharmaceutically acceptable carrier and one or more agents such as, but not limited to, antiobesity agents such as fenfluramine, dexfenfluramine, sibutramine, orlistat, or $\beta_3$ adrenoceptor agonists; feeding behavior modifying agents such as neuropeptide Y receptor antagonists, including those that antagonize the neuropeptide Y5 receptor;

α-MSH, α-MSH mimetics, or α-MSH derived peptides; MC-4R agonists or partial agonists such as, but not limited to, those disclosed in U.S. Pat. No. 6,350,760; MC-3R agonists; glucokinase activators; PPAR-δ agonists; PPAR-α/PPAR-γ agonists; PPAR-α/PPAR-γ/PPAR-δ agonists; PPAR-γ/PPAR-δ agonists; and agents useful in treatment of male and/or female sexual dysfunction, such as type V phosphodiesterase inhibitors such as sildenafil or tendamifil, dopamine agonists, or $α_2$-adrenoceptor antagonists.

In another embodiment, the present invention provides a pharmaceutical composition comprising a compound of Formula (I) or a pharmaceutically acceptable salt thereof, wherein the amount of the compound of Formula (I) is an amount sufficient to inhibit the function of AgRP at a melanocortin receptor. In an embodiment, the melanocortin receptor is MC-4R. In another embodiment, the melanocortin receptor is MC-3R.

A melanocortin receptor disorder, or a melanocortin receptor mediated disease, which may be treated by the methods provided herein, include, but are not limited to, any biological disorder or disease in which a melanocortin receptor is implicated, or which inhibition of a melanocortin receptor potentiates a biochemical pathway that is defective in the disorder or disease state. Factors which may influence what constitutes a therapeutically effective amount may depend upon the size and weight of the subject, the biodegradability of the therapeutic agent, the activity of the therapeutic agent, as well as its bioavailability.

The present invention also provides a method for the synthesis of compounds useful as intermediates in the preparation of compounds of Formula (I) and salts thereof along with methods for the preparation of pharmaceutical compositions comprising a compound of Formula (I) or a pharmaceutically acceptable salt thereof. Unless otherwise indicated, variables refer to those for Formula (I).

Scheme 1 illustrates a synthesis of compounds of Formula (I). Thiazole ring formation can be accomplished by combination of the alpha-bromoketone (1) and the thiourea derivative (2) (wherein R is an alkyl group) under conditions such as those described in general procedure C to provide compound (3). The ester group of compound (3) may then be hydrolyzed under conditions, such as those in general procedure G, to provide a compound of Formula (I).

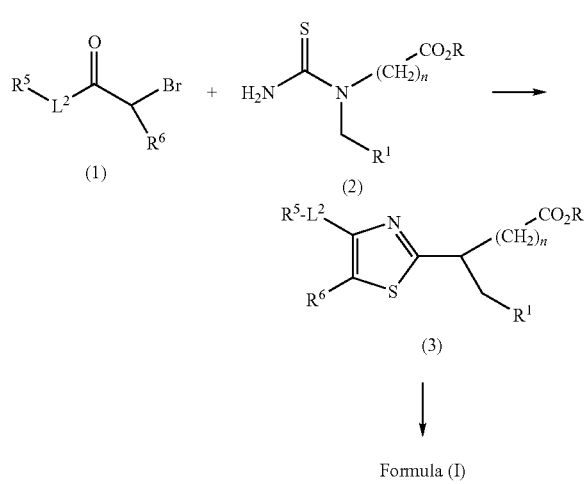

Scheme 1

Methods of Treatment

In another aspect, the present invention provides a method of treatment comprising administering to a subject a therapeutically effective amount of a compound of Formula (I) or a pharmaceutically acceptable salt thereof.

In another embodiment, the present invention provides a method of treatment of an obesity-related disorder comprising: administering to a subject a therapeutically effective amount of a compound of Formula (I) or a pharmaceutically acceptable salt thereof. In another embodiment, the obesity-related disorder is selected from the group consisting of: dyslipidemia, hypertriglyceridemia, hypertension, diabetes, Syndrome X, atherosclerotic disease, cardiovascular disease, cerebrovascular disease, peripheral vessel disease, cholesterol gallstones, cancer, menstrual abnormalities, infertility, polycystic ovaries, osteoarthritis, and sleep apnea.

In another embodiment, the present invention provides a method of treatment of a disorder comprising: administering to a subject a therapeutically effective amount of a compound of Formula (I) or a pharmaceutically acceptable salt thereof, wherein the disorder is selected from the group consisting of female sexual dysfunction, male sexual dysfunction, and erectile dysfunction. In another embodiment, the present invention provides a method of stimulating sexual response in a mammal comprising: administering to a mammal a therapeutically effective amount of a compound of Formula (I) or a pharmaceutically acceptable salt thereof. In embodiment, the mammal is a male. In another embodiment, the mammal is a female. In another embodiment, the mammal is a human.

The compounds of Formula (I) or pharmaceutically acceptable salts thereof may be used in combination with one or more therapeutic agents which are used in the treatment, amelioration, and/or suppression of diseases for which the compounds of Formula (I) or pharmaceutically acceptable salts thereof are useful; such other therapeutic agents may be administered by a like route or different route as that of the compound of Formula (I) or pharmaceutically acceptable salt thereof. Where a compound of Formula (I) or a pharmaceutically acceptable salt thereof is utilized in combination with another therapeutic agent, the composition may contain the compound of Formula (I) or a pharmaceutically acceptable salt there of in combination with the other therapeutic agent(s). Where separate dosage formulations are used, the compound of Formula (I) or pharmaceutically acceptable salt thereof and one or more additional therapeutic agents may be administered at essentially the same time (e.g., concurrently) or at separately staggered times (e.g., sequentially).

In another embodiment, the present invention provides a method of treatment of an obesity-related disorder comprising: administering to a subject a therapeutically effective amount of a compound of Formula (I) or a pharmaceutically acceptable salt thereof in combination with one or more hypoglycemic agents.

In another embodiment, the present invention provides a method of treatment of an obesity-related disorder comprising: administering to a subject a therapeutically effective amount of a compound of Formula (I) or a pharmaceutically acceptable salt thereof in combination with one or more agents that modulate digestion and/or metabolism. The agents that modulate digestion and/or metabolism may include, but are not limited to, agents that modulate thermogenesis, lipolysis, gut motility, fat absorption, and satiety.

In another embodiment, the present invention provides a method of treating obesity and obesity-related disorders comprising: administering to a subject a therapeutically effective amount of a compound of Formula (I) or a pharmaceutically acceptable salt thereof in combination with one or more agents selected from the group consisting of HMG CoA reductase inhibitor, bile acid binding agent, fibric acid derivative, and agent that regulates hypertension.

In another embodiment, the present invention provides a method of treatment comprising: administering to a subject a therapeutically effective amount of a compound of Formula (I) or a pharmaceutically acceptable salt thereof in combination with one or more agents such as, but not limited to, antiobesity agents such as fenfluramine, dexfenfluramine, sibutramine, orlistat, or $\beta_3$ adrenoceptor agonists; feeding behavior modifying agents such as neuropeptide Y receptor antagonists, including those that antagonize the neuropeptide Y5 receptor; α-MSH, α-MSH mimetics, or α-MSH derived peptides; MC-4R agonists or partial agonists such as, but not limited to, those disclosed in U.S. Pat. No. 6,350,760; MC-3R agonists; glucokinase activators; PPAR-δ agonists; PPAR-α/PPAR-γ agonists; PPAR-α/PPAR-γ/PPAR-δ agonists; PPAR-γ/PPAR-δ agonists; and agents useful in treatment of male and/or female sexual dysfunction, such as type V phosphodiesterase inhibitors such as sildenafil or tendamifil, dopamine agonists, or $\alpha_2$-adrenoceptor antagonists.

In another embodiment, the present invention provides a method of treatment comprising: administering to a subject a therapeutically effective amount of a compound of Formula (I) or a pharmaceutically acceptable salt thereof, wherein said therapeutically effective amount is sufficient to induce weight loss in the subject.

In another embodiment, the present invention provides a method of prevention of weight gain comprising: administering to a subject a therapeutically effective amount of a compound of Formula (I) or a pharmaceutically acceptable salt thereof which is sufficient to prevent weight gain.

In another embodiment, the present invention provides a method of treatment comprising: administering to a subject a therapeutically effective amount of a compound of Formula (I) or a pharmaceutically acceptable salt thereof, wherein the compound is administered in an amount is sufficient to induce weight loss in the subject.

In another embodiment, the present invention provides a method of treatment comprising: administering to a subject a therapeutically effective amount of a compound of Formula (I) or a pharmaceutically acceptable salt thereof, wherein the compound is administered in an amount is sufficient to halt weight gain in the subject.

In another embodiment, the present invention provides a method of treatment comprising: administering to a subject a therapeutically effective amount of a compound of Formula (I) or a pharmaceutically acceptable salt thereof, wherein the compound is administered in an amount is sufficient to decrease the rate of weight gain in the subject.

In another embodiment, the present invention provides a method of reducing a subject's desire for food comprising: administering to a subject a therapeutically effective amount of a compound of Formula (I) or a pharmaceutically acceptable salt thereof, wherein said therapeutically effective amount is sufficient to decrease a subject's desire for food in the subject.

In another embodiment, the present invention provides a method of reducing a subject's caloric intake comprising: administering to a subject a therapeutically effective amount of a compound of Formula (I) or a pharmaceutically acceptable salt thereof, wherein said therapeutically effective amount is sufficient to reduce a subject's caloric intake.

In another embodiment, the present invention provides a method of melanocortin receptor modulation comprising: administering to a subject an amount of a compound of Formula (I) or a pharmaceutically acceptable salt thereof so as to modulate a melanocortin receptor in the subject. In another embodiment, the present invention provides a method of melanocortin receptor modulation comprising: administering to a subject an amount of a compound of Formula (I) or a pharmaceutically acceptable salt thereof, so as to enhance the downstream effects of agonist binding to the melanocortin receptor in the subject.

In another embodiment, the present invention provides a method of treatment of a disorder comprising: administering to a subject a therapeutically effective amount of a compound of Formula (I) or a pharmaceutically acceptable salt thereof, wherein the disorder is selected from the group consisting of female sexual dysfunction.

In another embodiment, the present invention provides a method of treatment of a disorder comprising: administering to a subject a therapeutically effective amount of a compound of Formula (I) or a pharmaceutically acceptable salt thereof, wherein the disorder is selected from the group consisting of male sexual dysfunction.

In another embodiment, the present invention provides a method of treatment comprising: administering to a subject a therapeutically effective amount of a compound of Formula (I) or a pharmaceutically acceptable salt thereof, wherein the compound is administered in an amount sufficient to induce weight loss, halt weight gain, or decrease the rate of weight gain in the subject.

The compounds of the invention may be useful in the treatment of diseases, disorders or conditions including, but not limited to, treating male and female sexual dysfunctions including hypoactive sexual desire disorder, sexual arousal disorder, orgasmic disorder and/or sexual pain disorder in females, male erectile dysfunction, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, lower urinary tract dysfunction conditions, cancer, gall bladder disease, sleep apnea, depression, anxiety, compulsion, neuroses, insomnia/sleep disorder, substance abuse, pain, fever, inflammation, immune modulation, rheumatoid arthritis, skin tanning, acne and other skin disorders, neuroprotective and cognitive and memory enhancement including the treatment of Alzheimer's disease. Accordingly the present invention provides for the use of a compound of formula (I) or a pharmaceutically acceptable salt thereof as a medicament.

The substituted aminothiazoles derivatives of the present invention may be useful in treating female sexual dysfunctions including hypoactive sexual desire disorder, sexual arousal disorder, orgasmic disorder, sexual pain disorder.

The categories of FSD are best defined by contrasting them to the phases of normal female sexual response: desire, arousal and orgasm (Leiblum, S. R. (1998)—Definition and classification of female sexual disorders. Int. J. Impotence Res., 10, S104-S106). Desire or libido is the drive for sexual expression. Its manifestations often include sexual thoughts either when in the company of an interested partner or when exposed to other erotic stimuli. Arousal is the vascular response to sexual stimulation, an important component of which is genital engorgement and includes increased vaginal lubrication, elongation of the vagina and increased genital sensation/sensitivity. Orgasm is the release of sexual tension that has culminated during arousal.

Hence, FSD occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders. The substituted aminothiazoles derivatives of the present invention may improve the genital response to sexual stimulation (as in female sexual arousal disorder), in doing so it may also improve the associated pain, distress and discomfort associated with intercourse and so treat other female sexual disorders.

Hypoactive sexual desire disorder is present if a woman has no or little desire to be sexual, and has no or few sexual thoughts or fantasies. This type of FSD can be caused by low testosterone levels due either to natural menopause or to surgical menopause. Other causes include illness, medications, fatigue, depression and anxiety. Thus, the substituted aminothiazoles derivatives of the present invention may treat hypoactive sexual desire disorder.

Female Sexual Arousal Disorder (FSAD) may be defined as being: a persistent or recurrent inability to attain or to maintain until completion of the sexual activity adequate lubrication-swelling response of sexual excitement. The disturbance may cause marked distress or interpersonal difficulty. Female sexual arousal disorder may be characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants e.g. selective serotonin reuptake inhibitors (SSRIs) or antihypertensive agents.

Sexual pain disorders (includes dyspareunia and vaginismus) is characterised by pain resulting from penetration and may be caused by medications which reduce lubrication, endometriosis, pelvic inflammatory disease, inflammatory bowel disease or urinary tract problems.

Thus, in accordance with another embodiment of the invention, there is provided use of a compound of formula (I) or a pharmaceutically acceptable salt thereof in the preparation of a medicament for the treatment of female sexual dysfunction, more particularly hypoactive sexual desire disorder, sexual arousal disorder, orgasmic disorder and sexual pain disorder.

The compounds of formula (I) or pharmaceutically acceptable salts thereof may be useful in the treatment of sexual arousal disorder, orgasmic disorder, and hypoactive sexual desire disorder. The compounds of formula (I) or pharmaceutically acceptable salts thereof may be useful in the treatment of a subject with female sexual arousal disorder and concomitant hypoactive sexual desire disorder.

The compounds of formula (I) or pharmaceutically acceptable salts thereof may be useful in the preparation of a medicament for the treatment of female sexual arousal disorder.

The compounds of the invention may find application in the following sub-populations of patients with FSD: the young, the elderly, pre-menopausal, peri-menopausal, post-menopausal women with or without hormone replacement therapy.

The compounds of the invention find may find application in patients with FSD arising from: i) Vasculogenic etiologies e.g. cardiovascular or atherosclerotic diseases, hypercholesterolemia, cigarette smoking, diabetes, hypertension, radiation and perineal trauma, traumatic injury to the iliohypogastric pudendal vascular system; ii) Neurogenic etiologies such as spinal cord injuries or diseases of the central nervous system including multiple sclerosis, diabetes, Parkinsonism, cerebrovascular accidents, peripheral neuropathies, trauma or radical pelvic surgery; iii) Hormonal/endocrine etiologies such as dysfunction of the hypothalamic/pituitary/gonadal axis, or dysfunction of the ovaries, dysfunction of the pancreas, surgical or medical castration, androgen deficiency, high circulating levels of prolactin e.g. hyperprolactinemia, natural menopause, premature ovarian failure, hyper and hypothyroidism; iv) Psychogenic etiologies such as depression, obsessive compulsive disorder, anxiety disorder, post-natal depression/"Baby Blues", emotional and relational issues, performance anxiety, marital discord, dysfunctional attitudes, sexual phobias, religious inhibition or a traumatic past experiences; and/or v) Drug-induced sexual dysfunction resulting from therapy with selective serotonin reuptake inhibitors (SSR is) and other antidepressant therapies (tricyclics and major tranquilizers), anti-hypertensive therapies, sympatholytic drugs, chronic oral contraceptive pill therapy.

In another embodiment, the present invention provides a method of melanocortin receptor modulation comprising: administering to a subject a therapeutically effective amount of a compound of Formula (I), wherein the compound of Formula (I) inhibits the function of AgRP on MC-4R. In another embodiment, the present invention provides a method of melanocortin receptor modulation comprising: administering to a subject a therapeutically effective amount of a compound of Formula (I), wherein the compound of Formula (I) inhibits the function of AgRP on MC-3R.

Generally speaking, a compound of Formula (I) may be administered at a dosage level of from about 0.003 to 500 mg/kg of the body weight of the subject being treated. In an embodiment, a compound of Formula (I) may be administered at a dosage range between about 0.003 and 200 mg/kg of body weight per day. In an embodiment, a compound of Formula (I) may be administered at a dosage range between about 0.1 to 100 mg/kg of body weight per day. The amount of active ingredient that may be combined with the carrier materials to produce a single dosage may vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms may generally contain between from about 5 mg to about 500 mg of active ingredient. This dosage may be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

The general procedures used in the methods to prepare the compounds of the present invention are described below.
General Experimental Section:

LC-MS data were obtained using gradient elution on a parallel MUX™ system, running four Waters® 1525 binary HPLC pumps, equipped with a Mux-UV 2488 multichannel UV-Vis detector (recording at 215 and 254 nM) and a Leap Technologies HTS PAL Auto sampler using a Sepax GP-C18, 4.6×50 mm; 5 micron particle-size column. A three minute gradient was run from 25% B (97.5% acetonitrile, 2.5% water, 0.05% TFA) and 75% A (97.5% water, 2.5% acetonitrile, 0.05% TFA) to 100% B. The system is interfaced with a Waters® Micromass ZQ mass spectrometer using electrospray ionization. MassLynx software was employed. All MS data were obtained in the positive mode unless otherwise noted. $^1$H NMR data were obtained on a Varian® 400 MHz spectrometer and chemical shifts were referenced using either the residual solvent signal (e.g., residual $CHCl_3$ in $CDCl_3$) or the TMS signal as an internal reference. Microwave heating procedures were used in some experiments and, in these cases, a Discover® microwave synthesis system (CEM, Matthews, N.C., USA) was used which included the use of pressurized glass reaction vessels at elevated temperatures.

All reagents and solvents including anhydrous solvents were commercially available and were used as received unless described otherwise. Solutions of Grignard reagents and organolithium reagents were commercially available and were used as received and at the concentrations listed on their labels. HCl in dioxane is a commercially-available solution of hydrogen chloride in dioxane and was used as received. Sodium hydride was purchased and used as a 60% suspension in oil without removal of the oil before reaction with acidic materials. Reactions are stirred using a magnetic stirring apparatus and magnetic stir bar in most cases. All reactions using air-sensitive reagents were run under inert gas. For reactions not heated using a microwave-generating apparatus, the reaction temperatures reported in the experimental section refer to the temperatures of an oil bath or cooling bath placed around a reaction vessel. For reactions performed using a microwave-generating apparatus, the temperatures refer to the temperatures reported by the microwave apparatus.

The compounds specifically exemplified below were named based on their chemical structure using Autonom 2000 (Version 4.1, SP1, Elsevier MDL) plug-in for ISIS Draw.

Abbreviations used in the Examples and text are as follows:
Aq=aqueous
DBU=1,8-diazabicyclo[5.4.0]undecene
DCM=dichloromethane
DIEA=diisopropylethylamine
DMF=N,N-dimethylformamide
DMSO=dimethylsulfoxide
Me=methyl
t-Bu=tert-butyl
Bu=butyl
iBu=isobutyl
EtOAc=ethyl acetate
g=gram
h=hour
HBTU=O-benzotriazol-1-yl-N,N,N',N'-tetramethyluronium hexafluorophosphate
HMPA=hexamethylphosphoric triamide
L=liter
LC-MS=liquid chromatography-mass spectrometry analysis
LDA=lithium diisopropylamide
M=molar
m/z=mass to charge ratio
MeOH=methanol
mg=milligram
min=minute
mL=milliliter
mM=millimolar
mmol=millimole
mol=mole
MS=mass spectrometry
N=normal
NCS=N-chlorosuccinimide
NMR=nuclear magnetic resonance spectroscopy
ppm=parts per million
psi=pounds per square inch
rt or RT=room temperature
TFA=trifluoroacetic acid
THF=tetrahydrofuran
THP=tetrahydropyranyl
TLC=thin layer chromatography
TMS=tetramethylsilane General Procedure A: Preparation of a Ketone from a Carboxylic Acid:

Method A1: A diethylether solution (5-40 mL) of carboxylic acid (1-10 mmol; 1 eq) in an ice bath is charged with a slow addition of methyl lithium in ethyl ether (1.5-1.6 M, 2.2-22 mmol; 2.2 eq) under nitrogen. The reaction is slowly warmed to room temperature and stirred for 4-16 h, with monitoring by TLC. The reaction mass is poured into water and is partitioned between cold aqueous sodium bicarbonate and ethyl acetate (1:1). The organic phase is washed with brine, dried over $Na_2SO_4$, concentrated under vacuum and is either used crude, or is filtered through a bed of silica gel using an eluent to afford the desired ketone after evaporation of the eluent under reduced pressure.

Method A2: To a solution of a carboxylic acid (2.0 mmol; 1 eq) in DMF (10 mL) is added HBTU (3.0 mmol; 1.5 eq), and DIEA (8.0 mmol; 4 eq). After stirring for 30 min at room temperature, N,O-dimethylhydroxylamine hydrochloride (3.0 mmol; 1.5 eq) is added. The reaction is stirred at room temperature while being monitored by TLC. After completion, the reaction is quenched by the addition of water (10 mL). The reaction mixture is extracted into ethyl acetate (3×20 mL), and the combined organic layers are dried over $Na_2SO_4$ and concentrated to obtain the desired N—(O-Methyl)amide derivative. The amide is dissolved in THF (10 mL) and the solution is cooled to 0° C. (ice bath). Methylmagnesium bromide (3.0 M in ethyl ether, 4 mmol; 2 eq) is added dropwise and the reaction is slowly allowed to warm to room temperature. The reaction is stirred at room temperature while being monitored by TLC. The reaction is cooled to 0° C. and is quenched by the addition of saturated aqueous ammonium chloride solution (10 mL) and then the mixture is extracted with EtOAc (3×20 mL). The combined organic layer is dried over $Na_2SO_4$, filtered and concentrated under vacuum. Purification by flash chromatography (e.g., hexanes, or ethyl acetate:hexanes 1:19 to 1:1) gives the desired methyl ketone.

This method can also be used similarly to produce ethyl ketones or other ketones by changing the lithium reagent used, e.g., by using ethyl lithium or another organolithium compound.

General Procedure B: alpha-Bromination of a Ketone:

Method B1: To a methanol solution (2-4 mL) of a ketone (1 mmol; 1 eq) in an ice bath is added pyrrolidone hydrotribromide (1.1-1.2 mmol; 1.1-1.2 eq). The reaction is slowly warmed to a temperature selected between room temperature and 60° C., and is stirred at the same temperature for 2-24 h, monitoring with TLC. After the reaction is judged to be complete, the reaction mass is concentrated under vacuum and is partitioned between cold aqueous sodium bicarbonate and ethyl acetate (30 mL, 1:1). The organic phase is dried with $Na_2SO_4$, concentrated under vacuum, and is either used crude or is filtered through a bed of silica gel to afford the desired 2-bromo ketone after evaporation of the eluent.

Method B2: To a methanol solution of a ketone (1-6 mmol; 1 eq) in an ice bath is added bromine (1.05-6.5 mmol; 1.05-1.1 eq) slowly over 15 min. The reaction is slowly warmed to room temperature and is stirred at the same temperature for 30 min, monitoring by TLC. The reaction mass is concentrated and the resulting 2-bromoketone is either used in the next step without further purification or is used after filtration through silica gel using an eluent, following evaporation of the eluent.

General Procedure C: Preparation of a 2-Aminothiazole Derivative:

A 2-bromoketone (0.1-1 mmol; 1 eq) in methanol or dichloromethane (1-5 mL) is added to the appropriate thiourea derivative such as TU1, TU2, TU3, TU4 or TU5 below (0.11-1.1 mmol; 1.1 eq) either neat, or as a solution in THF (0.5-3 mL). The reaction is stirred at a selected temperature between RT and 60° C. for between 30 min to 24 hours. The reaction is monitored by TLC until judged complete; or if required, another portion of bromoketone is added to bring the reaction to completion. The reaction mass is concentrated under vacuum and is partitioned between aqueous sodium bicarbonate and ethyl acetate (30 mL, 1:1). The aqueous layer is washed with ethyl acetate (3×15 mL), and the combined organic layers are washed with brine, dried over $Na_2SO_4$ and concentrated under vacuum. The crude residue is purified by silica gel chromatography using ethyl acetate:hexanes to afford the desired 2-aminothiazole derivative.

General Procedure D: Preparation of a N,N-Disubstituted Thiourea Derivative:

A mixture of the appropriate aldehyde (1 mmol; 1 eq) and the appropriate amine or amine hydrochloride derivative (1.2 mmol; 1.2 eq) in DCM (5 mL) is stirred for 5 min. Sodium triacetoxyborohydride (1.2-2.5 mmol; 1.2 to 2.5 eq) is added in portions and the reaction is stirred until completion of the reaction is shown by TLC or LCMS. The reaction mixture is partitioned between DCM or dichloroethane (10 mL) and saturated aqueous $NaHCO_3$ solution (15 mL). The aqueous layer is extracted again with DCM or dichloroethane (1×15 mL). The combined organic extracts are dried over $K_2CO_3$. After evaporating the solvents, the crude product is dissolved in DCM or dichloroethane (20 mL) and Fmoc-isothiocyanate (1.0 mmol; 1.0 eq; (CAS: [199915-38-3])) is added. The reaction is stirred at room temperature for 0.5-15 h. After LCMS or TLC indicates that the reaction is complete, piperidine (0.5-3 mL; 2-15 eq) is added and stirred for 1-2 h at room temperature to remove the Fmoc group. The solvents are evaporated under vacuum, and the crude residue is filtered on a bed of silica gel using ethyl acetate:hexane or ethyl acetate:DCM to afford the desired N,N-disubstituted thiourea derivative. These thiourea derivatives, in general, are unstable and should be kept cold to improve their stability when stored.

General Procedure E: Preparation of an ester from a Carboxylic Acid:

To a methanol solution of a carboxylic acid (1 mmol) is added 4N HCl in dioxane solution (1 mL) at room temperature. The reaction is stirred at room temperature for 7-8 h and is monitored by TLC or LCMS. The reaction is concentrated under vacuum and is partitioned between aqueous sodium bicarbonate and ethyl acetate (30 mL, 1:1). The organic phase is dried with $Na_2SO_4$, concentrated and is filtered through a bed of silica gel to afford the desired ester.

General Procedure F: LDA Alkylation:

To a stirred solution of an ester or sterically-hindered aldehyde (1 mmol; 1 eq) in dry THF (10 mL) under nitrogen atmosphere at −78° C. (dry-ice/acetone bath) is added a solution of LDA in THF (1.2 mmol; 1.2 eq) over 15 min. The resulting reaction mixture is brought to room temperature slowly over 30 min. The reaction mixture is cooled to −78° C., and then the appropriate alkyl halide (2 mmol; 2 eq) is added. After completion of the addition, the reaction mixture is allowed to attain room temperature and stirring is continued at room temperature until the completion of the reaction is noted, as determined by TLC or LCMS monitoring. The reaction mixture is poured into brine (20 mL) and is extracted with ethyl acetate (2×30 mL). The combined organic layers are washed with brine, dried over $Na_2SO_4$, and concentrated under reduced pressure. The residue is purified by silica gel flash column chromatography to give the desired product.

General Procedure G: Hydrolysis of an ester:

Method G1: To a solution of the appropriate ester (0.1-1 mmol; 1 eq) in THF:MeOH (2:1, 1-10 mL) is added NaOH (0.5-2 mmol; 2-5 eq) dissolved in $H_2O$ (1-10 mL). The reaction is stirred at a temperature between room temperature and 60° C. until complete, as judged by TLC or LCMS. The solvent is evaporated, and the residue is partitioned between a solvent, such as ethyl ether or DCM, and water. The pH of the aqueous layer is adjusted to ~pH 7 with 10% aq HCl (or with citric acid) and then the product is extracted with DCM or ethyl acetate (3×5 mL). The combined organic layers are dried over $Na_2SO_4$, concentrated and filtered on bed of silica gel to give the desired acid after evaporation of the eluent.

Method G2: To a solution of the appropriate ester (1 mmol) in THF:EtOH (2:1, 3 mL) or ethanol in a resealable, glass pressure-vessel equipped with a magnetic stirbar is added KOH (3 mmol) dissolved in $H_2O$ (1 mL). The resulting reaction mixture is heated in a CEM Discover PLS™ microwave at 150° C. for 2 h. The solvent is evaporated under vacuum, and the residue is acidified with 2N aq HCl. The product is extracted with DCM (3×5 mL), dried over $Na_2SO_4$ and is concentrated under reduced pressure to give the desired carboxylic acid.

General Procedure H: Sodium Salt Formation:

A NaOH (aq) solution (0.1-0.11 mmol; 1-1.1 eq) is added to a solution of the appropriate carboxylic acid (0.1 mmol; 1 eq) in THF (0.1-2 mL) and MeOH (0.1-2 mL). After stirring for 15 min all the volatiles are evaporated under reduced pressure and the solid is triturated with ethyl ether or DCM, and then is dried under high vacuum to give the desired carboxylate salt.

General Procedure I: Grignard Reaction:

To a THF solution of the appropriate aldehyde (1.0 mmol; 1 eq) in an ice bath is added dropwise a solution of the appropriate alkylmagnesium halide (1.5 mmol; 1.5 eq) in an appropriate solvent under nitrogen. The reaction is slowly warmed to room temperature and is stirred for 7-8 h with occasional monitoring by TLC. After completion of the reaction, ammonium chloride solution (aq) is added and the product is extracted into ethyl acetate (2×15 mL). The combined organic phase is washed with brine, dried over $Na_2SO_4$, concentrated under vacuum, and the product is filtered through a bed of silica gel using an eluent to afford the desired alcohol after evaporation of the eluent at reduced pressure.

General Procedure J: PCC Oxidation:

To a dichloromethane solution of the appropriate alcohol (1.0 mmol) is added molecular sieves (oven-dried 4A sieves; about 10% of the weight of the alcohol) and pyridinium chlorochromate (PCC, 1.5 mmol) at room temperature. The reaction is stirred for 7-8 h, with monitoring by TLC. The reaction mixture is loaded onto a bed of silica gel, and the product is eluted with ethyl ether or another appropriate eluent. The eluent is evaporated under vacuum to afford the desired ketone.

General Procedure K: Wittig Reaction:

(Methoxymethyl)triphenylphosphonium chloride (1.0 mmol; 1.0 eq) is dissolved or suspended in toluene and the solution is evaporated to dryness. This process is repeated once, and then the phosphonium salt is dissolved or suspended in dry THF. To this THF solution of dry phosphonium salt is added NaH (1.0 mmol; 1 eq) at 0° C. The reaction is slowly warmed to room temperature and stirred for 6 h until an orange-colored solution or suspension is formed. This solution is charged with the appropriate ketone (1.0 mmol) and the reaction is stirred at room temperature for 7-8 h. The reaction is monitored by TLC. The reaction is partitioned between water and ethyl acetate (30 mL, 1:1). The organic phase is dried with Na$_2$SO$_4$, concentrated under reduced pressure, and is filtered through a bed of silica gel to afford the purified enol ether product after evaporation of the eluent under reduced pressure.

General Procedure L: Hydrolysis of an Enol Ether:

A trifluoroacetic acid: dichloromethane (5 mL, 8:2) solution of the appropriate vinyl ether derivative (1.0 mmol) is stirred at room temperature for 10-20 min; the reaction is monitored by TLC or LCMS. The completed reaction is concentrated under vacuum and the residue is then partitioned between cold saturated sodium bicarbonate solution and ethyl acetate (30 mL, 1:1). The organic phase is dried with Na$_2$SO$_4$, and is concentrated under reduced pressure. If needed, the product can be dissolved in EtOAc/hexanes and filtered through a bed of silica gel to afford the purified aldehyde product after evaporation of the eluent under reduced pressure.

General Procedure M: Hydrogenation of an Aromatic Ring or Aromatic Chloride:

To a stirred solution of the appropriate aromatic compound (1-3 mmol) dissolved in acetic acid, or dissolved in a mixture of MeOH:HOAc (1:1) in a resealable glass pressure-reaction vessel equipped with a manometer and magnetic stirbar is added PtO$_2$ (0.1 mmol). The resultant solution is subjected to hydrogenation at 50-55 psi of hydrogen with stirring via use of the magnetic stirbar and a stirplate. After completion of the reaction, the catalyst is filtered off using a pad of Celite®, and the Celite® is washed with methanol (10 mL). The combined filtrate is evaporated under reduced pressure to give the desired product. This product is used in the next step without further purification.

Intermediate TU1: 3-[1-(5-Methyl-thiophen-2-ylmethyl)-thioureido]-propionic acid tert-butyl ester

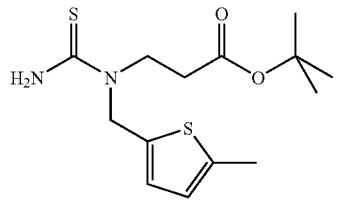 [SMILES: Cc1ccc(CN(CCC(=O)OC(C)(C)C)C(N)=S)s1]

A mixture of 5-methyl-thiophene-2-carboxaldehyde (8.0 g, 63.5 mmol) and 3-amino-propionic acid tert-butyl ester hydrochloride (13.8 g, 76.03 mmol) in DCM (500 mL) was stirred for 5 min. Sodium triacetoxyborohydride (35 g, 158.75 mmol) was added in portions over 20 min. The reaction mixture was slowly warmed to room temperature and stirred for two days. The reaction mixture was slowly poured onto an aq solution of K$_2$CO$_3$ and stirred for 1 h. The organic layer was separated, dried over sodium sulfate and filtered through Celite. To this DCM solution was added Fmoc-isothiocyanate (21.4 g, 76.19 mmol) and the reaction was stirred at room temperature for 1 h. After completion of the reaction, the solvent was evaporated under reduced pressure, and the crude material was purified on a silica gel column (eluent: 20:1 to 4:1 hexanes/ethyl acetate) to give the Fmoc-protected thiourea derivative (17.5 g, 51.5% yield).

To a DCM (100 mL) solution of the above obtained Fmoc-protected thiourea derivative (17.5 g, 32.7 mmol) was added piperidine (16.5 mL, 162.5 mmol) and the reaction was stirred for 15 min at room temperature, at which point the TLC analysis showed completion of the reaction. The reaction was diluted with hexanes (200 mL) and loaded onto a silica gel column. The product was eluted using mixtures of hexanes and ethyl acetate (10:1:hexanes:ethyl acetate to 1:1: hexanes:ethyl acetate) and the appropriate fractions were concentrated under reduced pressure to afford the desired thiourea (9.2 g, 89.75% yield). This material is unstable and should be kept in the cold to prevent cyclization and loss of t-BuOH. LC-MS m/z: 315 (M+1)$^+$. $^1$H NMR (400 MHz, CDCl$_3$): δ 8.40 (bd, 1H), 6.88 (d, 1H), 6.61 (d, 1H), 5.23 (s, 2H), 3.61 (t, 2H), 2.66 (t, 3H), 2.45 (s, 3H), 1.44 (s, 9H).

Intermediate TU2: 3-[1-(5-Ethyl-thiophen-2-ylmethyl)-thioureido]-propionic acid tert-butyl ester

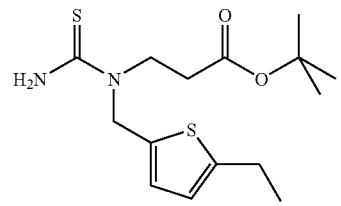 [SMILES: CCc1ccc(CN(CCC(=O)OC(C)(C)C)C(N)=S)s1]

A mixture of 5-ethyl-thiophene-2-carboxaldehyde (14.25 g, 101.6 mmol) and 3-amino-propionic acid tert-butyl ester hydrochloride (22.2 g, 122 mmol) in DCM was stirred for 3 hr at RT. Sodium triacetoxyborohydride (30.1 g, 142.2 mmol) was added in portions and the reaction was stirred for 2 h, at which point TLC indicated the completion of the reaction. To the reaction mixture was added a saturated aq solution of sodium bicarbonate, and then the phases were separated. The aqueous layer was extracted with DCM two times. The combined organic extracts were dried over sodium sulfate, concentrated under vacuum and the resulting material was purified on a silica gel column (eluent: hexanes→2% hexanes in EtOAc→5% hexanes in EtOAc→10% hexanes in EtOAc→20% hexanes in EtOAc→50% hexanes in EtOAc) to give 3-[(5-ethyl-thiophen-2-ylmethyl)-amino]-propionic acid tert-butyl ester (8.91 g, 32.6% yield).

The above obtained 3-[(5-ethyl-thiophen-2-ylmethyl)-amino]-propionic acid tert-butyl ester (8.91 g, 33.07 mmol) was dissolved in DCM and cooled to 0° C., then Fmoc-isothiocyanate (8.46 g, 30.07 mmol) was added. The reaction was stirred at room temperature for 3 h. After TLC indicated the completion of the reaction, the reaction was cooled to 0° C. and piperidine (8.46 g, 9.8 mL, 79.4 mmol) was added. The deprotection reaction was stirred for 2 h at room temperature. The solvents were evaporated under vacuum, and the crude residue was triturated with hexanes (3×100 mL). The solvent was concentrated under vacuum, then the residue was dried on vacuum to afford the above titled thiourea product (10.95 g). This material is unstable and should be kept in the cold to prevent cyclization and loss of t-BuOH. LC-MS m/z: 329 (M+1)$^+$. $^1$H NMR (400 MHz, CDCl$_3$): δ 6.90 (d, 1H), 6.64 (d, 1H), 5.24 (s, 2H), 3.60 (t, 2H), 2.80 (q, 2H), 2.63 (t, 2H), 1.44 (s, 9H), 1.28 (t, 3H).

Intermediate TU3: 3-[1-(2,5-Dimethyl-thiophen-3-ylmethyl)-thioureido]-propionic acid tert-butyl ester

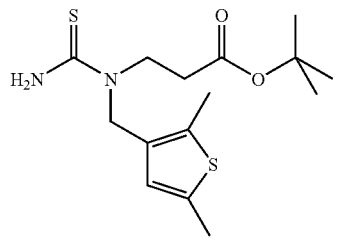 [SMILES: Cc1cc(CN(CCC(=O)OC(C)(C)C)C(N)=S)c(C)s1]

To DMF (100 mL) stirred in an ice bath was added POCl$_3$ (25 mL) drop wise followed by the addition of 2,5-dimethyl-thiophene (5 mL). The solution was warmed to room temperature and then was heated at 80° C. overnight. The reaction was cooled to room temperature and was slowly added to ice. Sodium acetate was added to bring the pH to between 5 and 6. The aqueous portion was extracted with ethyl acetate, and the organic portion was dried over sodium sulfate, concentrated under reduced pressure and purified on a silica gel column (eluent: 10:1:hexanes:EtOAc→4:1:hexanes:EtOAc to yield 2,5-dimethyl-thiophene-3-carboxaldehyde (1.5 g).

A mixture of above obtained aldehyde (1.2 g, 8.57 mmol) and 3-amino-propionic acid tert-butyl ester hydrochloride (1.9 g, 10.28 mmol) in DCM (30 mL) was stirred for 5 min. Sodium triacetoxyborohydride (4.5 g, 21.42 mmol) was added in portions and the reaction was stirred at room temperature overnight. Saturated aqueous NaHCO$_3$ solution was added and the mixture was stirred for 30 min. The layers were separated and the aqueous layer was extracted again with DCM. The organic layers were combined and to this solution was added Fmoc-isothiocyanate (Fmoc-NCS, 3.5 g, 12.46 mmol). After stirring the reaction for 1 h, the mixture was concentrated and the crude material was purified on a silica gel column (eluent: 10:1:hexanes:EtOAc→4:1:hexanes:EtOAc) to yield the purified Fmoc-protected thiourea derivative. This Fmoc-protected thiourea derivative was dissolved in DCM and to the solution was added piperidine (2.5 eq). After stirring the reaction mixture for 30 min, it was diluted with hexanes and the soluble material was concentrated under vacuum to give an oil. The oil was loaded onto a silica gel column for purification (eluent: hexanes→DCM→10% EtOAc in DCM→20% EtOAc in DCM). Concentration of the appropriate fractions gave the desired thiourea (2.0 g, 71.4% yield from aldehyde). This material is unstable and should be kept in the cold to prevent decomposition by cyclization and loss of t-BuOH. LC-MS m/z: 329 (M+1)$^+$. $^1$H NMR (400 MHz, CDCl$_3$): δ 6.61 (s, 1H), 5.01 (s, 2H), 3.48 (t, 2H), 2.64 (t, 2H), 2.39 (s, 3H), 2.38 (s, 3H), 1.46 (s, 9H).

Intermediate TU4: 3-[1-(5-Methanesulfonyl-thiophen-2-ylmethyl)-thioureido]-Propionic acid tert-butyl ester

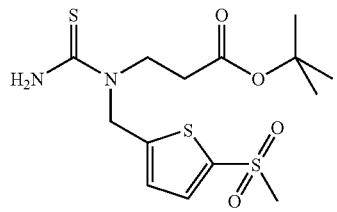 [SMILES: CC(C)(C)OC(=O)CCN(Cc1ccc(S(C)(=O)=O)s1)C(N)=S]

To a THF (3 mL) solution of 5-methanesulfonyl-thiophene-2-carboxylic acid (900 mg, 4.32 mmol) at RT was added borane in THF (1M solution, 6 mL) and the reaction was stirred at room temperature overnight. The reaction was cooled in an ice bath and quenched with methanol. The solvent was evaporated under reduced pressure and the mixture was purified on a silica gel column to afford (5-methanesulfonyl-thiophen-2-yl)-methanol (500 mg, 60.2% yield).

The above obtained alcohol (500 mg, 2.6 mmol) was converted to 5-methanesulfonyl-thiophene-2-carboxaldehyde (250 mg, 50% yield) following General Procedure J using pyridinium chlorochromate (1.5 g, 4 mmol) in DCM (10 mL).

A mixture of the above obtained aldehyde (250 mg, 1.3 mmol) and 3-amino-propionic acid tert-butyl ester hydrochloride (230 mg, 1.57 mmol) in DCM (5 mL) was stirred for 15 min. Sodium triacetoxyborohydride (422 mg, 2 mmol) was added and the reaction was stirred at room temperature overnight. The reaction mixture was partitioned between aqueous sodium bicarbonate and DCM, and the layers were separated. The organic layer was dried over sodium sulfate and concentrated to give the crude amine product: 3-[(5-methanesulfonyl-thiophen-2-ylmethyl)-amino]-propionic acid tert-butyl ester (300 mg, 63% yield). This crude amine (300 mg, 0.82 mmol) was dissolved in DCM and Fmoc-isothiocyanate (250 mg, 0.9 mmol) was added to the solution. After stirring the reaction overnight at room temperature, piperidine (3 mL) was added and the ensuing deprotection reaction was stirred for 30 min. The reaction mixture was concentrated and purified by silica gel chromatography to obtain the desired thiourea (250 mg, 72% yield) after evaporation of the eluent at reduced pressure. This material is unstable and should be kept in the cold to prevent decomposition by cyclization and loss of t-BuOH.

Intermediate TU5: 3-[1-(5-methylsulfanyl-thiophen-2-ylmethyl)-thioureido]-propionic acid tert-butyl ester

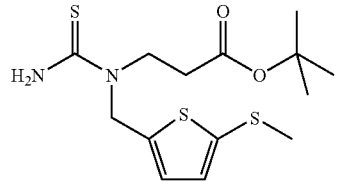 [SMILES: CSc1ccc(CN(CCC(=O)OC(C)(C)C)C(N)=S)s1]

A mixture of 5-methylsulfanyl-thiophene-2-carbaldehyde (1.0 g, 6.3 mmol) and 3-amino-propionic acid tert-butyl ester hydrochloride (1.02 g, 7 mmol) in DCM (20 mL) was stirred at RT for 15 min. Sodium triacetoxyborohydride (2 g, 9.45 mmol) was added and the reaction was stirred at room temperature overnight. The reaction mass was partitioned between aqueous sodium bicarbonate and DCM. The organic layer was dried over sodium sulfate and concentrated to give the crude 3-[(5-methylsulfanyl-thiophen-2-ylmethyl)-amino]-propionic acid tert-butyl ester (800 mg, 38% yield). This crude amine (800 mg, 2.4 mmol) was dissolved in DCM (10 mL) and Fmoc-isothiocyanate (740 mg, 2.6 mmol) was added. After stirring the reaction overnight at room temperature, piperidine (3 mL) was added and the deprotection reaction was stirred for 30 min. The reaction mixture was concentrated and purified using a silica gel column. Concentration of the appropriate fractions under vacuum gave the desired thiourea (600 mg, 63% yield). This material is unstable and should be kept in the cold to prevent decomposition by cyclization and loss of t-BuOH. LC-MS m/z: 347 (M+1)+. ¹H NMR (400 MHz, CDCl₃): δ 6.85 (d, 1H), 6.82 (d, 1H), 5.85 (s, 2H), 3.52 (t, 2H), 2.65 (t, 2H), 2.41 (s, 3H), 2.38 (s, 3H), 1.38 (s, 9H).

Example 1

Sodium; 3-[(4-bicyclo[2.2.1]hept-2-yl-thiazol-2-yl)-(5-ethyl-thiophen-2-ylmethyl)-amino]-propionate

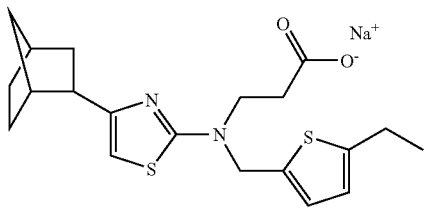 [SMILES: CCc1ccc(CN(CCC(=O)[O-])c2nc(C3CC4CCC3C4)cs2)s1 ; [Na+]]

1-Bicyclo[2.2.1]hept-2-yl-ethanone (500 mg, 3.62 mmol) was treated with pyrrolidone hydrotribromide (1.97 g, 3.98 mmol) in MeOH (about 10 mL) following a method analogous to General Procedure B1. The reaction was stirred overnight at RT, and after completion of the reaction, as determined by TLC, the solvent was evaporated under reduced pressure. Ethyl acetate and aq sodium bicarbonate solution were added, and the layers were separated. The aq layer was extracted 2 times with ethyl acetate, and the combined organic portion was dried over sodium sulfate. The solution was decanted from the drying agent and the solvent was evaporated under reduced pressure to afford the 2-bromoketone derivative which was used in next step without further purification.

Following a method analogous to General Procedure C, a portion of the above crude alpha-bromoketone (81 mg, 0.37 mmol) was added to a methanol (about 10 mL) solution of 3-[1-(5-ethyl-thiophen-2-ylmethyl)-thioureido]-propionic acid tert-butyl ester (122 mg, 0.371 mmol) and the reaction was heated at 60° C. and stirred overnight. The solvent was evaporated and ethyl acetate and saturated aq sodium bicarbonate solution were added to the residue. Extraction of the aq layer was performed two times with ethyl acetate. The combined organic portion was dried over sodium sulfate, and the dried solvent was decanted from the drying agent. The solvent was removed under reduced pressure to give the crude material. This was purified using silica gel chromatography (eluent: hexanes→19:1 hexanes:EtOAc→9:1 hexanes:EtOAc to give the purified 3-[(4-bicyclo[2.2.1]hept-2-yl-thiazol-2-yl)-(5-ethyl-thiophen-2-ylmethyl)-amino]-propionic acid tert-butyl ester (139 mg, 0.311 mmol, 84%) after evaporation of the eluent under reduced pressure.

The above tert-butyl propionate derivative (139 mg, 0.311 mmol) was hydrolyzed following a method analogous to General Procedure G1 using aq NaOH: THF: MeOH at 60° C. to afford 3-[(4-bicyclo[2.2.1]hept-2-yl-thiazol-2-yl)-(5-ethyl-thiophen-2-ylmethyl)-amino]-propionic acid (74 mg, 0.189 mmol, 61%) after workup and silica gel chromatography (eluent: hexanes→4:1 hexanes:EtOAc→1:1 hexanes:EtOAc. LC-MS m/z: 391 (M+1)+. The sodium salt of this acid (title compound) was prepared following a method analogous to General Procedure H using 0.105 N NaOH (aq., 1.80 mL), THF (2 mL) and MeOH (2 mL). ¹H NMR (400 MHz, CD₃OD, Sodium salt): δ 6.84 (d, 1H), 6.60 (d, 1H), 6.13 (s, 1H), 4.81 (s, 2H), 3.60 (t, 2H), 2.76 (q, 2H), 2.66 (dd, 1H), 2.50 (t, 2H), 2.37 (s, 1H), 2.28 (s, 1H), 1.78-1.48 (m, 5H), 1.45-1.32 (m, 2H), 1.30-1.21 (m, 4H).

Example 2

3-[(4-cyclohexyl-thiazol-2-yl)-(5-ethyl-thiophen-2-ylmethyl)-amino]-propionic acid

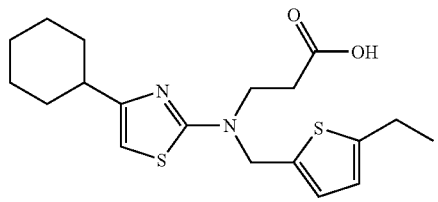 [SMILES: CCc1ccc(CN(CCC(=O)O)c2nc(C3CCCCC3)cs2)s1]

To 1-cyclohexyl-ethanone (314 mg, 2.49 mmol) in methanol (8 mL) was added pyrrolidone hydrotribromide (1.5 g, 3.0 mmol) and the reaction was stirred at room temperature overnight. To this reaction mixture of the 2-bromoketone intermediate was added thiourea (227 mg, 3.0 mmol) and the reaction was stirred at room temperature for 2 h to generate 2-amino-4-cyclohexylthiazole. After concentrating the reaction mixture, dichloromethane and aq sodium bicarbonate solution were added and the layers were separated. The dichloromethane layer was dried over sodium sulfate and the solution was concentrated to give the crude 2-amino-4-cyclohexylthiazole. This crude material was used for next step without further purification.

To a dichloromethane (20 mL) solution of above obtained 2-amino-4-cyclohexylthiazole was added 5-ethyl-thiophene-2-carboxaldehyde (0.37 mL, 0.3 mmol) and titanium (IV) isopropoxide (1.31 mL, 5.5 mmol) at room temperature. After stirring for 10 min at room temperature, sodium triacetoxyborohydride (5 mmol) was added. The reaction was stirred at room temperature for 2 h and the reaction's progress was monitored by TLC. After completion of the reaction, saturated aq NaHCO₃ solution was slowly added and the aq portion was extracted with dichloromethane (2×20 mL). The combined organic layer was dried over Na₂SO₄ and concentrated under reduced pressure to afford (4-cyclohexyl-thiazol-2-yl)-(5-ethyl-thiophen-2-ylmethyl)-amine. This crude amine was used in next step without further purification.

A mixture of above obtained (4-cyclohexyl-thiazol-2-yl)-(5-ethyl-thiophen-2-ylmethyl)-amine, ethyl acrylate (1 mL) and DBU (0.1 mL) were heated at 60° C. for 2 h. After the reaction was completed, excess ethyl acrylate was distilled off using a rotary evaporator. The crude residue was purified by silica gel chromatography to obtain the product: 3-[(4-cyclohexyl-thiazol-2-yl)-(5-ethyl-thiophen-2-ylmethyl)-amino]-propionic acid ethyl ester. (300 mg, 30% yield for three steps).

The above obtained propionic acid ethyl ester was hydrolyzed using a method similar to General Procedure G1 to give 3-[(4-cyclohexyl-thiazol-2-yl)-(5-ethyl-thiophen-2-ylmethyl)-amino]-propionic acid (106 mg, 38% yield). LC-MS m/z: 379 (M+1)+. ¹H NMR (400 MHz, CDCl₃): δ 6.83 (d, 1H), 6.35 (d, 1H), 6.11 (s, 1H), 4.60 (s, 2H), 3.76 (dd, 2H), 2.81 (q, 2H), 2.70 (dd, 2H), 2.56 (m, 1H), 2.00 (m, 2H), 1.80-1.60 (m, 4H), 1.40-1.20 (m, 7H). LC-MS m/z: 379 (acid, M+1)+. The sodium salt of the title compound could be prepared following a procedure similar to General Procedure H.

Example 3

3-[(4-Cyclohexylmethyl-thiazol-2-yl)-(5-ethyl-thiophen-2-ylmethyl)-amino]-propionic acid Cyclohexylacetone (300 mg, 2.14 mmol) in MeOH (5 mL) was treated with pyrrolidone hydrotribromide (1.3 g, 4.28 mmol) and the reaction was stirred at RT overnight. To the resulting solution of crude alpha-bromoketone in MeOH (without workup) was directly added solid sodium bicarbonate to neutralize the acid formed in the bromination step. To this neutralized bromoketone mixture was added 3-[1-(5-ethyl-thiophen-2-ylmethyl)-thioureido]-propionic acid tert-butyl ester (150 mg) in THF (2 mL) and the reaction was stirred for 1 h at RT. The solvent was removed at reduced pressure and the residue was dissolved in water and ethyl acetate. The aq portion was extracted two times with EtOAc, and the combined organic portion was washed with brine and then dried over sodium sulfate. Solvent removal under reduced pressure gave the crude product which was partially purified by silica gel chromatography (eluent: 10:1 hexanes:EtOAc) to give the aminothiazole derivative (300 mg).

A portion of this material (150 mg) was hydrolyzed with 2N aq NaOH (1.5 mL) in THF (4 mL): MeOH (2 mL) at 50° C. overnight. The solvent was evaporated at reduced pressure and the residue was dissolved in water and the solution was washed with EtOAc two times (2×10 mL). The aq layer was acidified with 2N citric acid and the aq portion was extracted two times with EtOAc (2×15 mL). The combined organic portion from the acidified extractions was washed with brine and dried over sodium sulfate. The solution was concentrated under vacuum to give the crude product, which was purified by silica gel chromatography (eluent: hexanes:EtOAc:10:1→2:1) to give 106 mg of the desired acid. LC-MS m/z: 393 (M+1)$^+$. $^1$H NMR (400 MHz, CDCl$_3$): δ 6.83 (d, 1H), 6.64 (d, 1H), 6.12 (s, 1H), 4.61 (s, 2H), 3.76 (t, 2H), 2.78 (q, 2H), 2.70 (t, 2H), 2.43 (d, 2H), 1.70-0.90 (m, 14H).

The carboxylate sodium salt of title compound could be prepared by a procedure analogous to General Procedure H.

Example 4

3-[(4-Cyclopentylmethyl-thiazol-2-yl)-(5-ethyl-thiophen-2-ylmethyl)-amino]-propionic acid Cyclopentylacetone (300 mg, 2.38 mmol) and pyrrolidone hydrotribromide (1.42 g, 2.6 mmol) were used to produce a MeOH solution of alpha-bromoketone, in an analogous fashion to Example 3. This solution of bromoketone (without workup) was treated with solid sodium bicarbonate and then with 3-[1-(5-ethyl-thiophen-2-ylmethyl)-thioureido]-propionic acid tert-butyl ester (150 mg), in an identical fashion as in Example 3 for the cyclohexyl derivative, to give the aminothiazole t-butyl propionate intermediate (250 mg) after chromatography. A portion of this material (150 mg) was hydrolyzed in a manner analogous to the procedure given in Example 3 to give the desired acid (82 mg). LC-MS m/z: 379 (M+1)$^+$. $^1$H NMR (400 MHz, CDCl$_3$): δ6.83 (d, 1H), 6.63 (d, 1H), 6.13 (s, 1H), 4.61 (s, 2H), 3.76 (t, 2H), 2.79 (q, 2H), 2.71 (t, 2H), 2.57 (d, 2H), 1.70-1.10 (m, 12H).

The carboxylate sodium salt of the title compound could be prepared by a procedure analogous to General Procedure H.

Example 5

Sodium; 3-{(5-ethyl-thiophen-2-ylmethyl)-[4-(4-methyl-cyclohexyl)-thiazol-2-yl]-amino}-propionate trans-4-Methyl-cyclohexanecarboxylic acid (2.84 mg, 2.0 mmol), was converted to 1-(trans-4-methyl-cyclohexyl)-ethanone following a method analogous to General Procedure A2 using N,O-dimethylhydroxylamine hydrochloride (292 mg, 3.0 mmol), HBTU (1.14 g, 3.0 mmol), and DIEA (1.4 mL, 8.0 mmol) to form the intermediate O-Methyl amide by stirring in DMF at RT overnight; work up by diluting the reaction with water and EtOAc, separating the phases, extracting the aq phase two times with EtOAc, and drying the combined organic portion with sodium sulfate, followed by evaporation of the solvent gave the crude O-methyl amide product after drying it overnight under vacuum. This crude material was then dissolved in THF, cooled to 0° C., and methylmagnesium bromide (3.0 M in ethyl ether, 1.33 mL, 4 mmol) was added. After 4 h, an additional equivalent of MeMgBr was added, and the reaction was stirred overnight at RT. The reaction was then cooled to 0° C. and the reaction was quenched with aq ammonium chloride, diluted with ethyl acetate, and the aqueous portion was extracted with EtOAc three times. The combined organic portion was dried over sodium sulfate and the solvent was removed under reduced pressure. The crude ketone was purified by silica gel chromatography (eluent: 19:1:hexanes:EtOAc→9:1:hexanes:EtOAc). A portion of this ketone (50 mg, 0.36 mmol) in MeOH was then converted into 2-Bromo-1-(trans-4-methyl-cyclohexyl)-ethanone (76 mg) using a method analogous to General Procedure B1. Pyrrolidone hydrotribromide (195 mg, 0.39 mmol) was added to the above methyl ketone in MeOH and the reaction was heated at 60° C. overnight. When complete, the solvent was evaporated and the residue was partitioned between EtOAc and saturated aq sodium bicarbonate solution. The phases were separated and the aqueous portion was extracted with EtOAc two times. The combined organic portion was dried over sodium sulfate and the solvent was removed under reduced pressure. The crude alpha-bromoketone was used directly in the next step.

2-Bromo-1-(trans-4-methyl-cyclohexyl)-ethanone (61 mg, 0.277 mmol) was added to a methanol (about 4 mL) solution of 3-[1-(5-ethyl-thiophen-2-ylmethyl)-thioureido]-propionic acid tert-butyl ester (100 mg, 0.304 mmol) and the reaction was heated at 60° C. overnight to obtain the 3-[[4-(trans-4-methyl-cyclohexyl)-thiazol-2-yl]-(5-ethyl-thiophen-2-ylmethyl)-amino]-propionic acid tert-butyl ester product following a method analogous to General Procedure C. The solvent was removed at reduced pressure and the residue was dissolved in aqueous saturated sodium bicarbonate solution and ethyl acetate. The aq portion was extracted two times with EtOAc, and the combined organic portion was dried over sodium sulfate. Solvent removal under reduced pressure gave the crude product which was purified by silica gel chromatography (eluent: hexanes→19:1 hexanes:EtOAc→9:1 hexanes:EtOAc) to give the aminothiazole derivative (52 mg).

This material (52 mg) was hydrolyzed with NaOH (100 mg) in 1:1:1 water:THF:MeOH (about 2 mL) at 50° C. overnight. The solvent was evaporated at reduced pressure and the residue was dissolved in water. The aq layer was acidified with 3M HCl to about pH 5-6 and the aq portion was extracted three times with DCM. The combined organic portion was dried over sodium sulfate. The solution was concentrated under vacuum to give the crude product, which was purified by silica gel chromatography (eluent: hexanes→4:1:hexanes:EtOAc→1:1 hexanes:EtOAc→) to give 31 mg of the desired acid. LC-MS m/z: 393 (M+1)$^+$. (400 MHz, CD$_3$OD): δ 6.84 (d, 1H), 6.60 (d, 1H), 6.13 (s, 1H), 4.81 (s, 2H), 3.60 (t, 2H), 2.76 (q, 2H), 2.50 (t, 2H), 2.43 (m, 1H), 2.05 (d, 2H), 1.79 (d, 2H), 1.47-1.30 (m, 3H), 1.24 (t, 3H), 1.13-0.99 (m, 2H), 0.93 (d, 3H).

The corresponding carboxylate sodium salt (title compound) was prepared by a procedure analogous to General Procedure H using the above acid (20 mg) and aq NaOH (485 μL of 0.105 N NaOH).

Example 6

Sodium; 3-{(5-methyl-thiophen-2-ylmethyl)-[4-(1-phenyl-cyclohexyl)-thiazol-2-yl]-amino}-propionate The title compound was made using a sequence of reactions that included bromination of 1-phenyl-1-acetylcyclohexane (600 mg, 3 mmol) with pyrrolidone hydrotribromide (1.5 g, 3.15 mmol) in MeOH (7 mL) and subsequent coupling of a portion of the resulting bromoketone (100 mg, 0.35 mmol) with 3-[1-(5-methyl-thiophen-2-ylmethyl)-thioureido]-propionic acid tert-butyl ester (123 mg, 0.4 mmol) in MeOH (3 mL) to give the propionic ester derivative (70 mg) as an intermediate. This ester intermediate (70 mg, 0.14 mmol) was hydrolyzed in MeOH: THF: 2N aq NaOH (1:1:1, 3 mL) at 50° C. to give the corresponding acid after workup with aq HCl and EtOAc, followed by drying and evaporation of the solvent under reduced pressure. LC-MS m/z: 441 (M+1)$^+$. The corresponding sodium carboxylate salt (title compound) was generated using 1.1 eq of 2N NaOH in 1:1 MeOH:THF at room temperature. The title compound was then isolated by evaporation of solvent at reduced pressure (Yield: 40 mg).

Example 7

Sodium; 3-[[4-(trans-4-tert-butyl-cyclohexyl)-thiazol-2-yl]-(5-methyl-thiophen-2-ylmethyl)-amino]-propionate

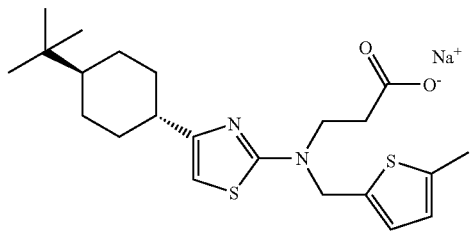 [SMILES: Cc1ccc(CN(CCC(=O)[O-])c2nc([C@H]3CC[C@H](C(C)(C)C)CC3)cs2)s1 ; [Na+]]

To trans-4-tert-butyl-cyclohexanecarboxylic acid (921 mg, 5.0 mmol) in ethyl ether (35 mL) was added methyl lithium (1.6 M in ethyl ether, 7.1 mL, 11.4 mmol) to produce 1-(trans-4-tert-butyl-cyclohexyl)-ethanone (769 mg, 4.22 mmol, 84%) following a method analogous to General Procedure A1. Workup involved treatment of the reaction mixture with water (50 mL), and the organic portion was washed with aq NaHCO$_3$ and then brine, and dried over sodium sulfate. Solvent evaporation under reduced pressure gave the crude methyl ketone (769 mg). This crude ketone product was converted into the corresponding 2-bromoketone (525 mg, 2.01 mmol) following a method analogous to General Procedure B2 using bromine (0.228 mL, 4.43 mmol) and MeOH (about 10 mL).

3-[1-(5-methyl-thiophen-2-ylmethyl)-thioureido]-propionic acid tert-butyl ester (100 mg, 0.318 mmol) in MeOH (about 4 mL) was treated with two portions of 2-Bromo-1-(trans-4-tert-butyl-cyclohexyl)-ethanone (2×83 mg, 2×0.318 mmol) (second addition spaced at an interval of 2 hours after first portion) at 60° C. following a method analogous to General Procedure C to produce 3-[[4-(trans-4-tert-Butyl-cyclohexyl)-thiazol-2-yl]-(5-methyl-thiophen-2-ylmethyl)-amino]propionic acid tert-butyl ester (158 mg). which was isolated by a workup that included evaporation of the solvent and partitioning the resulting material between EtOAc and saturated aq sodium bicarbonate solution. Extraction of the aq sodium bicarbonate layer with EtOAc (2 times), drying the combined organic portion over sodium sulfate and evaporation of the solvent gave the crude material which was purified using silica gel chromatography (eluent hexanes→19:1 ethyl acetate:hexanes→9:1 ethyl acetate:hexanes).

Hydrolysis of above ester product (158 mg) at 50° C. using 1 N NaOH (aq) solution (2 mL), THF (1 mL) and MeOH (1 mL) following a method analogous to General Procedure G1 gave 3-[[4-(trans-4-tert-butyl-cyclohexyl)-thiazol-2-yl]-(5-methyl-thiophen-2-ylmethyl)-amino]-propionic acid after aq workup (evaporation of solvent, dissolution of residue in water, treatment with 3 M HCl to pH 5-6, extraction with DCM three times, drying of combined organic portion over sodium sulfate, solvent evaporation) and silica gel chromatography (eluent: hexanes→4:1 ethyl acetate:hexanes→1:1 ethyl acetate:hexanes (97 mg, 0.231 mmol, 73%). LC-MS m/z: 421 (M+1)$^+$. The sodium salt was prepared from this material following a method analogous to General Procedure H using a solution of 0.105 N NaOH (aq) solution (2.20 mL), THF (about 2 mL) and MeOH (about 2 mL), and stirring for 15 minutes. Evaporation of the solvent, followed by treatment with DCM, evaporation (3×), and pumping under vacuum gave the desired sodium salt (title compound). $^1$H NMR (400 MHz, DMSO-d$_6$, Sodium salt): δ 6.80 (d, 1H), 6.60 (d, 1H), 6.17 (s, 1H), 4.72 (s, 2H), 3.35 (t, 2H), 2.36-2.27 (m, 4H), 2.12 (t, 2H), 2.01 (d, 2H), 1.78 (d, 2H), 1.37-1.22 (m, 2H), 1.11-0.94 (m, 3H), 0.83 (s, 9H).

Example 8

Sodium; 3-[[4-(trans-4-tert-butyl-cyclohexyl)-thiazol-2-yl]-(5-ethyl-thiophen-2-ylmethyl)-amino]-propionate

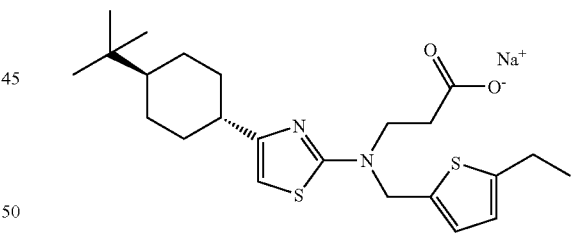

trans-4-tert-Butyl-cyclohexanecarboxylic acid (365 mg, 2.0 mmol), was converted to 1-(trans-4-tert-butyl-cyclohexyl)-ethanone (245 mg, 67%) following a method analogous to General Procedure A2 and similar to as shown in Example 5 using N,O-dimethylhydroxylamine hydrochloride (292 mg, 3.0 mmol), HBTU (1.14 g, 3.0 mmol), DIEA (1.4 mL, 8.0 mmol), and methylmagnesium bromide (3.0 M in ethyl ether, 1.33 mL, 4 mmol). 2-Bromo-1-(trans-4-tert-butyl-cyclohexyl)-ethanone (382 mg) was then prepared from this ketone (245 mg, 1.35 mmol) following a method analogous to General Procedure B1 (and the procedure given in Example 5) using pyrrolidone hydrotribromide (701 mg, 1.41 mmol) and MeOH (about 10 mL).

2-Bromo-1-(trans-4-tert-butyl-cyclohexyl)-ethanone (72 mg, 0.277 mmol) was added to a methanol (about 4 mL)

solution of 3-[1-(5-ethyl-thiophen-2-ylmethyl)-thioureido]-propionic acid tert-butyl ester (100 mg, 0.304 mmol) to obtain 3-[[4-(trans-4-tert-butyl-cyclohexyl)-thiazol-2-yl]-(5-ethyl-thiophen-2-ylmethyl)-amino]-propionic acid tert-butyl ester (108 mg, 0.220 mmol) following a method analogous to General Procedure C (and similar to the procedure found in Example 5). Hydrolysis of this ester following a method analogous to General Procedure G1 using 1 N NaOH (aq) solution (2 mL), THF (1 mL) and MeOH (1 mL) gave 3-[[4-(trans-4-tert-butyl-cyclohexyl)-thiazol-2-yl]-(5-ethyl-thiophen-2-ylmethyl)-amino]-propionic acid (37 mg, 0.085 mmol). LC-MS m/z: 435 (M+1)$^+$.

The sodium salt of the above acid (title compound) was prepared following a method analogous to General Procedure H using 0.105 N NaOH (aq) solution (0.811 mL), THF (2 mL) and MeOH (2 mL). $^1$H NMR (400 MHz, DMSO-d$_6$; Sodium salt): δ 6.85 (d, 1H), 6.61 (d, 1H), 6.15 (s, 1H), 4.80 (s, 2H), 3.62 (t, 2H), 2.76 (q, 2H), 2.53 (t, 2H), 2.43 (m, 1H), 2.12 (d, 2H), 1.89 (d, 2H), 1.43-1.30 (m, 2H), 1.24 (t, 3H), 1.18-0.95 (m, 3H), 0.89 (s, 9H).

Example 9

Sodium; 3-[[4-(4-trans-isopropyl-cyclohexyl)-thiazol-2-yl]-(5-methyl-thiophen-2-ylmethyl)-amino]-propionate The title compound was synthesized from a sequence of reactions starting from trans-4-isopropylcyclohexanecarboxylic acid (2.0 g, 11.75 mmol) and MeLi (1.6 M, 2.28 eq, 26.8 mmol) in ethyl ether to generate the methyl ketone after workup (1.91 g) (See Example 5 for similar workup conditions). Bromination of a portion of this ketone (1.0 g, 5.95 mmol) was accomplished using bromine (998 mg, 6.24 mmol) in MeOH at 0° C. followed by warming to room temperature, and the crude bromoketone was isolated after workup (821 mg) (See Example 5 for similar workup conditions). Treatment of a portion of the crude bromoketone (100 mg, 0.405 mmol) with 3-[1-(5-methyl-thiophen-2-ylmethyl)-thioureido]-propionic acid tert-butyl ester (127 mg, 0.405 mmol) in MeOH at 60° C., followed by workup (See Example 5 for similar workup conditions) and chromatography (eluent: hexanes→2.5% ethyl acetate in hexanes→5% ethyl acetate in hexanes) gave the propionate t-Bu-ester derivative (187 mg). Hydrolysis of this ester with NaOH (about 100 mg) in aq THF:MeOH as in Example 5 gave the carboxylic acid after workup (96 mg). LC-MS m/z: 421 (M+1)$^+$. This acid material can be converted to the sodium salt (title compound) using 0.105N aq NaOH as in Example 5. (400 MHz, CD$_3$OD, Sodium salt): δ 6.82 (d, 1H), 6.57 (d, 1H), 6.13 (s, 1H), 4.80 (s, 2H), 3.60 (t, 2H), 2.50 (t, 2H), 2.44 (m, 1H), 2.39 (s, 3H), 2.10 (d, 2H), 1.83 (d, 2H), 1.49-1.27 (m, 3H), 1.19-1.06 (m, 3H), 0.90 (d, 6H).

Example 10

Sodium; 3-[(5-ethyl-thiophen-2-ylmethyl)-[4-(4-trans-isopropyl-cyclohexyl)-thiazol-2-yl]-amino]-propionate In a sequence analogous to that given in Example 9, trans-4-isopropylcyclohexanecarboxylic acid was converted into the title compound by treating the bromoketone intermediate (133 mg, 0.405 mmol) with 3-[1-(5-ethyl-thiophen-2-ylmethyl)-thioureido]-propionic acid tert-butyl ester (127 mg, 0.405 mmol), to give the ester intermediate (147 mg) and hydrolyzing this new ester product as given in Example 9 to give the carboxylic acid after workup. LC-MS m/z: 421 (M+1)$^+$. (400 MHz, CD$_3$OD): δ 6.84 (d, 1H), 6.60 (d, 1H), 6.13 (s, 1H), 4.81 (s, 2H), 3.61 (t, 2H), 2.76 (q, 2H), 2.50 (t, 2H), 2.44 (m, 1H), 2.10 (d, 2H), 1.83 (d, 2H), 1.49-1.30 (m, 3H), 1.24 (t, 3H), 1.19-1.07 (m, 3H), 0.90 (d, 6H). The desired sodium salt (title compound) was generated from 106 mg of the acid in a similar manner as that described in Example 5.

The compounds shown in Examples 11-37 in the table below could be made in a manner similar to using the sequences of reactions given for Examples 9 and 10 above. The starting carboxylic acids were commercially-available, and incorporated the structures of R$_2$ given in the table below (e.g., the starting carboxylic acid for Examples 9 and 10 below is trans-4-cyclohexanecarboxylic acid, and the starting carboxylic acid for Examples 11 and 12 is indanecarboxylic acid). The appropriate starting N,N-disubstituted-thioureas used in the coupling with bromoketones in these procedures were made by methods as exemplified earlier in Examples TU1-TU5 or by similar methods. If the name of a compound in the table below is given as a sodium salt, this indicates that the sodium salt was prepared from the acid.

| Ex | Name | R$^x$ | R$^y$ | LC-MS m/z (acid, M + 1)$^+$ |
|---|---|---|---|---|
| 11 | 3-[(5-Ethyl-thiophen-2-ylmethyl)-(4-indan-2-yl-thiazol-2-yl)-amino]-propionic acid | 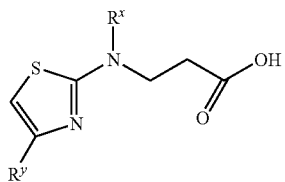 | | 413 |

-continued

| Ex | Name | Rˣ | Rʸ | LC-MS m/z (acid, M + 1)⁺ |
|---|---|---|---|---|
| 12 | 3-[(4-Indan-2-yl-thiazol-2-yl)-(5-methyl-thiophen-2-ylmethyl)-amino]-propionic acid | 5-methyl-thiophen-2-ylmethyl | indan-2-yl | 399 |
| 13 | 3-{(5-Ethyl-thiophen-2-ylmethyl)-[4-(1,2,3,4-tetrahydro-naphthalen-2-yl)-thiazol-2-yl]-amino}-propionic acid | 5-ethyl-thiophen-2-ylmethyl | 1,2,3,4-tetrahydro-naphthalen-2-yl | 427 |
| 14 | 3-{(5-Methyl-thiophen-2-ylmethyl)-[4-(1,2,3,4-tetrahydro-naphthalen-2-yl)-thiazol-2-yl]-amino}-propionic acid | 5-methyl-thiophen-2-ylmethyl | 1,2,3,4-tetrahydro-naphthalen-2-yl | 413 |
| 15 | 3-{(5-Ethyl-thiophen-2-ylmethyl)-[4-(4-methyl-cyclohexylmethyl)-thiazol-2-yl]-amino}-propionic acid | 5-ethyl-thiophen-2-ylmethyl | 4-methyl-cyclohexylmethyl | 407 |
| 16 | 3-[[4-(4-Methyl-cyclohexylmethyl)-thiazol-2-yl]-(5-methyl-thiophen-2-ylmethyl)-amino]-propionic acid | 5-methyl-thiophen-2-ylmethyl | 4-methyl-cyclohexylmethyl | 393 |
| 17 | 3-{(5-Ethyl-thiophen-2-ylmethyl)-[4-(4-trifluoromethyl-cyclohexyl)-thiazol-2-yl]-amino}-propionic acid | 5-ethyl-thiophen-2-ylmethyl | 4-trifluoromethyl-cyclohexyl | 447 |
| 18 | 3-{(5-Methyl-thiophen-2-ylmethyl)-[4-(4-trifluoromethyl-cyclohexyl)-thiazol-2-yl]-amino}-propionic acid | 5-methyl-thiophen-2-ylmethyl | 4-trifluoromethyl-cyclohexyl | 433 |

-continued

| Ex | Name | R$^x$ | R$^y$ | LC-MS m/z (acid, M + 1)$^+$ |
|---|---|---|---|---|
| 19 | 3-[[4-(4-Ethyl-cyclohexyl)-thiazol-2-yl]-(5-methyl-thiophen-2-ylmethyl)-amino]-propionic acid | | | 393 |
| 20 | 3-[[4-(4-Ethyl-cyclohexyl)-thiazol-2-yl]-(5-ethyl-thiophen-2-ylmethyl)-amino]-propionic acid | | | 407 |
| 21 | 3-{(5-Methyl-thiophen-2-ylmethyl)-[4-(4-propyl-cyclohexyl)-thiazol-2-yl]-amino}-propionic acid | | | 407 |
| 22 | 3-{(5-Ethyl-thiophen-2-ylmethyl)-[4-(4-propyl-cyclohexyl)-thiazol-2-yl]-amino}-propionic acid | | | 421 |
| 23 | Sodium; 3-[[4-(4,4-difluoro-cyclohexyl)-thiazol-2-yl]-(5-methyl-thiophen-2-ylmethyl)-amino]-propionate | | | 401 |
| 24 | Sodium; 3-[[4-(4,4-difluoro-cyclohexyl)-thiazol-2-yl]-(5-ethyl-thiophen-2-ylmethyl)-amino]-propionate | | | 415 |
| 25 | 3-[[4-(4-tert-Butyl-cyclohexyl)-thiazol-2-yl]-(2,5-dimethyl-thiophen-3-ylmethyl)-amino]-propionic acid | | | 435 |
| 26 | 3-{(2,5-Dimethyl-thiophen-3-ylmethyl)-[4-(4-isopropyl-cyclohexyl)-thiazol-2-yl]-amino}-propionic acid | | | 421 |

-continued

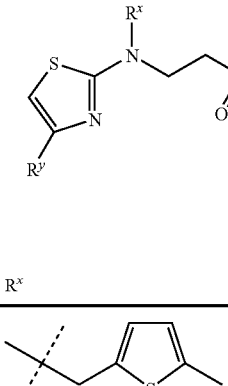

| Ex | Name | R$^x$ | R$^y$ | LC-MS m/z (acid, M + 1)$^+$ |
|---|---|---|---|---|
| 27 | 3-[[4-(4-tert-Butyl-cyclohexyl)-thiazol-2-yl]-(5-methyl-thiophen-2-ylmethyl)-amino]-propionic acid | 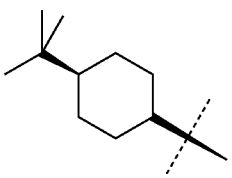 | 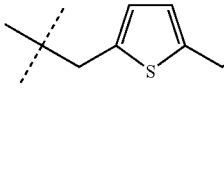 | 421 |
| 28 | 3-[[4-(4-tert-Butyl-cyclohexyl)-thiazol-2-yl]-(5-ethyl-thiophen-2-ylmethyl)-amino]-propionic acid | 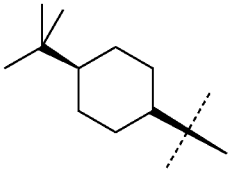 | 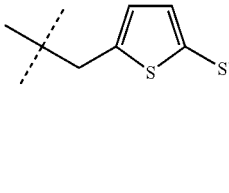 | 435 |
| 29 | Sodium; 3-[[4-(4-tert-butyl-cyclohexyl)-thiazol-2-yl]-(5-methylsulfanyl-thiophen-2-ylmethyl)-amino]-propionate | 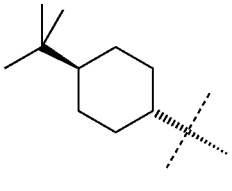 | 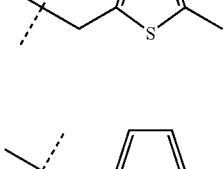 | 453 |
| 30 | 3-[[4-(4-Methoxy-cyclohexyl)-thiazol-2-yl]-(5-methyl-thiophen-2-ylmethyl)-amino]-propionic acid | 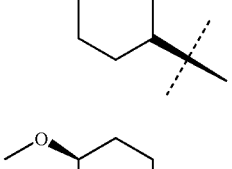 | 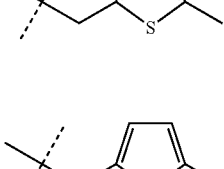 | 395 |
| 31 | 3-[[4-(4-Methoxy-cyclohexyl)-thiazol-2-yl]-(5-methyl-thiophen-2-ylmethyl)-amino]-propionic acid | 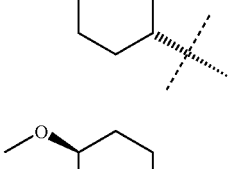 | 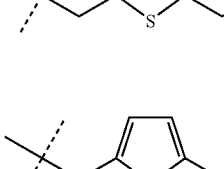 | 395 |
| 32 | 3-{(5-Ethyl-thiophen-2-ylmethyl)-[4-(4-methoxy-cyclohexyl)-thiazol-2-yl]-amino}-propionic acid | 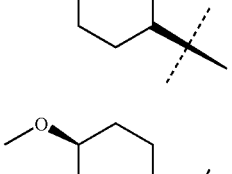 | 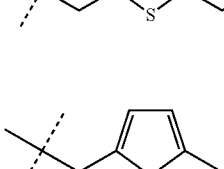 | 409 |
| 33 | 3-{(5-Ethyl-thiophen-2-ylmethyl)-[4-(4-methoxy-cyclohexyl)-thiazol-2-yl]-amino}-propionic acid | 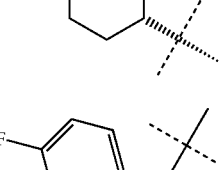 | 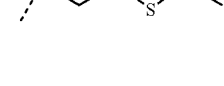 | 409 |
| 34 | Sodium; 3-[{4-[1-(4-fluoro-phenyl)-cyclopentyl]-thiazol-2-yl}-(5-methyl-thiophen-2-ylmethyl)-amino]-propionate | | 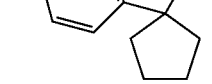 | 445 |

-continued

| Ex | Name | R$^x$ | R$^y$ | LC-MS m/z (acid, M + 1)$^+$ |
|---|---|---|---|---|
| 35 | Sodium; 3-{(5-methyl-thiophen-2-ylmethyl)-[4-(1-p-tolyl-cyclopentyl)-thiazol-2-yl]-amino}-propionate | | | 441 |
| 36 | 3-[[4-(4-tert-Butyl-cyclohexyl)-thiazol-2-yl]-(5-methanesulfonyl-thiophen-2-ylmethyl)-amino]-propionic acid | | | 485 |
| 37 | 3-[[4-(4-Isopropyl-cyclohexyl)-thiazol-2-yl]-(5-methanesulfonyl-thiophen-2-ylmethyl)-amino]-propionic acid | | | 471 |

Example 38

Sodium; 3-{(5-methyl-thiophen-2-ylmethyl)-[4-(trans-4-phenyl-cyclohexyl)-thiazol-2-yl]-amino}-propionate

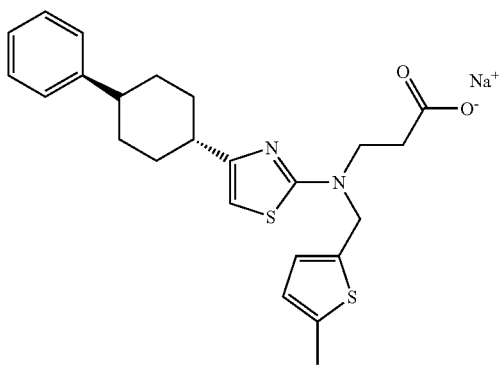

To a solution of 1-[4-(trans-4-chloro-phenyl)-cyclohexyl]-ethanone (600 mg, 2.5 mmol) in methanol (5 ml) was added Pd (30 mg; 20% on activated carbon) and the resultant mixture was stirred at RT under hydrogen pressure at 20 psi in a resealable glass pressure vessel (equipped with a manometer and pressure valve) overnight. The catalyst was filtered off using a pad of Celite®, and the Celite® was washed with methanol (about 10 mL) then the combined filtrate was evaporated under reduced pressure to give 1-(trans-4-phenyl-cyclohexyl)-ethanone (454 mg, 90% yield).

This above ketone was treated with pyrrolidone hydrotribromide (1.2 g, 2.36 mmol) in methanol (about 5 mL) at RT for 5 hours following a method analogous to General Procedure B1 to produce 2-bromo-1-(trans-4-phenyl-cyclohexyl)-ethanone (562 mg) after evaporation of the solvent, extractive workup with EtOAc and saturated aq sodium bicarbonate solution, drying the organic layer and evaporation of the solvent under reduced pressure.

Treatment of the above crude 2-bromo ketone (100 mg, 0.35 mmol) in MeOH (about 2 mL) with 3-[1-(5-methyl-thiophen-2-ylmethyl)-thioureido]-propionic acid tert-butyl ester (126 mg, 0.4 mmol) at 50° C. for 1 hr, following a method analogous to General Procedure C gave 3-{(5-methyl-thiophen-2-ylmethyl)-[4-(trans-4-phenyl-cyclohexyl)-thiazol-2-yl]-amino}-propionic acid tert-butyl ester (40 mg) after evaporation of the solvent and purification.

Treatment of the above tert-butyl propionate ester derivative with NaOH (1.0 mmol in 1:2 1:water:MeOH, THF; 1.5 mL) at 50° C. following a method analogous to General Procedure G1 gave 3-{(5-methyl-thiophen-2-ylmethyl)-[4-(trans-4-phenyl-cyclohexyl)-thiazol-2-yl]-amino}-propionic acid as a solid after treatment with 1N HCl, extractive workup with EtOAc, and purification. LC-MS m/z: 441 (M+1)$^+$. $^1$H NMR (400 MHz, CDCl$_3$): δ 7.17-7.33 (m, 5H), 6.82 (d, 1H), 6.61 (d, 1H), 6.17 (s, 1H), 4.62 (s, 2H), 3.78 (t, 2H), 2.73 (t, 2H), 2.66 (m, 1H), 2.57 (m, 1H), 2.44 (s, 3H), 2.13-2.20 (m, 2H), 1.96-2.03 (m, 2H), 1.51-1.67 (m, 4H). The corresponding sodium salt (title compound) was prepared following a method analogous to General Procedure H.

The following two examples were made starting from 2-bromo-1-(trans-4-phenyl-cyclohexyl)-ethanone (see Example 38) using the appropriate thiourea intermediates exemplified earlier and a sequence of methods analogous to General Procedures C, G1 and H.

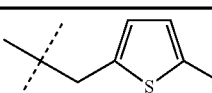

| Ex | Name | $R^x$ | $R^y$ | LC-MS m/z (acid, M + 1)$^+$ |
|---|---|---|---|---|
| 39 | Sodium; 3-{(5-ethyl-thiophen-2-ylmethyl)-[4-(4-phenyl-cyclohexyl)-thiazol-2-yl]-amino}-propionate | 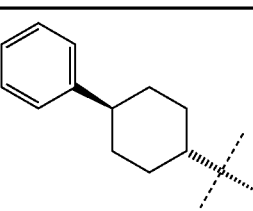 | 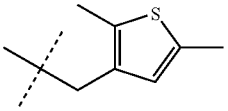 | 455 |
| 40 | Sodium; 3-{(2,5-dimethyl-thiophen-3-ylmethyl)-[4-(4-phenyl-cyclohexyl)-thiazol-2-yl]-amino}-propionate | 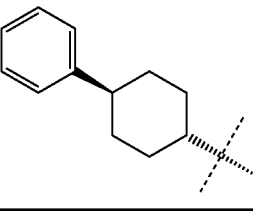 | 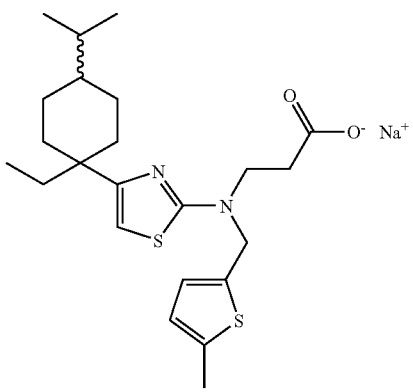 | 455 |

Example 41

Sodium; 3-[[4-(1-ethyl-4-isopropyl-cyclohexyl)-thiazol-2-yl]-(5-methyl-thiophen-2-ylmethyl)-amino]-propionate 4-Isopropyl-cyclohexanecarboxylic acid (1.0 g, 6.0 mmol) was converted to 4-Isopropyl-cyclohexanecarboxylic acid methyl ester (1.1 g, 99% crude yield) following a method analogous to General Procedure E using HCl-dioxane (2 mL, 4.0M) and methanol (10 mL) by stirring at RT overnight, and then evaporating the solvent under reduced pressure, followed by workup.

4-Isopropyl-cyclohexanecarboxylic acid methyl ester (1.1 g, 6 mmol) was alkylated using a method analogous to General Procedure F using LDA (9 mmol) and iodoethane (1.4 g, 9 mmol) in THF (20 mL) at −78° C. to RT to produce 1-ethyl-4-isopropyl-cyclohexanecarboxylic acid methyl ester (1.0 g, 78% yield) as a mixture of isomers. Hydrolysis of this ester using KOH (12.5 mmol) in aqueous EtOH (1:1; 5 mL) at 150° C. for 2 hr in a pressurized vessel following a microwave method analogous to General Procedure G2 gave 1-ethyl-4-isopropyl-cyclohexanecarboxylic acid (800 mg, 86% yield) as a mixture of isomers after workup by evaporation of the solvent, treatment with aq 2 N HCl, extractive workup, and evaporation of the solvent.

1-Ethyl-4-isopropyl-cyclohexanecarboxylic acid (800 mg, 4.7 mmol) in ethyl ether (about 20 mL) at 0° C. was treated with MeLi (5.5 mL in ethyl ether; 8.8 mmol) and stirred overnight at RT following a method analogous to General Procedure A1 to generate the corresponding methyl ketone (600 mg) after quenching the reaction with water, aq extractive workup, evaporation of the solvent and purification of the crude ketone. The resulting ketone (600 mg, 3 mmol) was treated with pyrrolidone hydrotribromide (1.6 g, 3.3 mmol) in MeOH (10 mL) and stirred at RT overnight following a method analogous to General Procedure B1 to produce 2-bromo-1-(1-ethyl-4-isopropyl-cyclohexyl)-ethanone (600 mg, 55% overall yield for two steps) after evaporation of the solvent, extractive workup with EtOAc and aq sodium bicarbonate, drying of the organic portion and removal of the solvent under vacuum.

A portion of the above 2-bromo ketone (50 mg, 0.18 mmol) was treated with 3-[1-(5-methyl-thiophen-2-ylmethyl)-thioureido]-propionic acid tert-butyl ester (63 mg, 0.20 mmol) in methanol (3 mL) at 50° C. for 1 hr following a method analogous to General Procedure C to produce 3-[[4-(1-ethyl-4-isopropyl-cyclohexyl)-thiazol-2-yl]-(5-methyl-thiophen-2-ylmethyl)-amino]-propionic acid tert-butyl ester (40 mg, 45% yield) after evaporation of the solvent, extractive workup with EtOAc and aq sodium bicarbonate, drying of the organic portion, removal of the solvent under vacuum, and purification.

The above tert-butyl propionate ester derivative (40 mg) was hydrolyzed using NaOH in 1:1:1: water:MeOH:THF (1.5 mL) following a method analogous to General Procedure G1 to produce 3-[[4-(1-ethyl-4-isopropyl-cyclohexyl)-thiazol-2-yl]-(5-methyl-thiophen-2-ylmethyl)-amino]-propionic acid (25 mg, 72% yield) as a mixture of cis/trans isomers after workup. LC-MS m/z: 435 (M+1)$^+$. $^1$H NMR (400 MHz, CDCl$_3$): δ 6.81 (m, 1H), 6.59 (m, 1H), 6.1-6.15 (2s, 1H), 4.64 (m, 2H), 3.74 (m, 2H), 2.73 (m, 2H), 2.44 (s, 3H), 2.30 (m, 1H), 2.01 (m, 1H), 1.75 (m, 1H), 1.53-1.61 (m, 2H), 1.51 (m, 1H), 1.23-1.30 (m, 4H), 1.00-1.06 (m, 2H), 0.88 (m, 3H), 0.81 (m, 3H), 0.60 (m, 3H). The sodium salt of this acid (title compound) was prepared following a method analogous to General Procedure H.

The compounds in the table below were prepared following synthetic routes similar to those described for Example 41, using sequences of reaction methods analogous to General Procedures E, F, G2, A1, B1, C, G1 and H.

The alpha-isobutylcyclopentanecarboxylic acid used as a starting material for the products in Examples 42-44 below was generated by alkylation of the methyl ester of cyclopentanecarboxylic acid (1 g, 7.8 mmol) using LDA (2M, 8.9 mL, 2.2 eq) and isobutyl iodide (excess) in THF (25 mL) at −78° C. to RT with stirring overnight. Extractive workup (2×50 mL EtOAc) after quenching with water, followed by washing with brine, drying over sodium sulfate, and concentration under reduced pressure gave the crude alkylated ester. Hydrolysis of this material with 6M NaOH (1 mL) in MeOH: THF (5 mL: 5 mL) in a pressurized vessel at 100° C. using microwave radiation for 45 min; concentration of the reaction to dryness, acidification, and purification using silica gel chromatography (eluent: 10:1 hexanes:EtOAc→2:1 hexanes: EtOAc) gave the desired alpha-isobutylcyclopentanecarboxylic acid (650 mg), which could be converted into the thiazole products of Examples 43-35 via the corresponding ketone and bromoketone intermediates and coupling with thiourea derivatives, and other procedures as similarly exemplified in Example 41.

The 1-ethyl-4-methylcyclohexanecarboxylic acid used as a starting material for the product in Example 45 below was generated by alkylation of the methyl ester of 4-methylcyclohexanecarboxylic acid (700 mg, 4.5 mmol) using LDA (1.5 eq) and ethyl iodide (1.5 eq) in THF (10 mL) at −78° C. to RT with stirring overnight. Extractive workup with EtOAc after quenching with water, followed by purification gave the alkylated ester (500 mg) as a mixture of isomers. Hydrolysis of this material (500 mg, 2.7 mmol) with an excess of concentrated aq KOH in EtOH:THF (2 mL:1 mL) in a pressurized vessel at 100° C. using microwave radiation for 4 hr; concentration of the reaction to dryness, acidification, extractive workup with EtOAc, and purification gave the desired 1-ethyl-4-methylcyclohexanecarboxylic acid (300 mg) as a mixture of isomers, which could be converted into the thiazole product of Example 46 via the corresponding ketone and bromoketone intermediates and coupling with the appropriate thiourea derivative, and other procedures as similarly exemplified in Example 41.

The 1-methyl-4-methylcyclohexanecarboxylic acid used as a starting material for the products in Examples 46-47 below was generated in a sequence of reactions similar to that given above for the synthesis of 1-ethyl-4-methylcyclohexanecarboxylic acid, with the exception that methyl iodide instead of ethyl iodide was used as the alkylating agent in the LDA alkylation step. This material could be converted into the thiazole products of Examples 46 and 47 via the corresponding ketone and bromoketone intermediates and coupling with the appropriate thiourea derivatives, and other subsequent procedures as similarly exemplified in Example 41.

Similarly, the 1-methyl-4-isopropylcyclohexanecarboxylic acid used as a starting material for the products in Examples 48-49 below was generated as a mixture of isomers in a sequence of reactions similar to that given above for the synthesis of 1-methyl-4-methylcyclohexanecarboxylic acid, with the exception that the methyl ester of 4-isopropylcyclohexanecarboxylic acid was used instead of the methyl ester of 4-methylcyclohexanecarboxylic acid in the LDA alkylation step. This alkylated material could be converted into the thiazole products of Examples 48 and 49 via the corresponding ketone and bromoketone intermediates and coupling with the appropriate thiourea derivatives, and other subsequent procedures as similarly exemplified in Example 41.

Similarly, the 1-methyl-4-t-butylcyclohexanecarboxylic acid used as a starting material for the product in Example 50 below was generated as a mixture of isomers in a sequence of reactions similar to that given above for the synthesis of 1-methyl-4-methylcyclohexanecarboxylic acid, with the exception that the methyl ester of 4-t-butylcyclohexanecarboxylic acid was used instead of the methyl ester of 4-methylcyclohexanecarboxylic acid in the LDA alkylation step. This alkylated material could be converted into the thiazole product of Example 50 via the corresponding ketone and bromoketone intermediates and coupling with the appropriate thiourea derivative, and other subsequent procedures as similarly exemplified in Example 41.

Similarly, the 1-methyl-4-phenylcyclohexanecarboxylic acid used as a starting material for the product in Example 51 below was generated as a mixture of isomers in a sequence of reactions similar to that given above for the synthesis of 1-methyl-4-methylcyclohexanecarboxylic acids with the exception that the methyl ester of 4-phenylcyclohexanecarboxylic acid was used instead of the methyl ester of 4-methylcyclohexanecarboxylic acid in the LDA alkylation step. This alkylated material could be converted into the thiazole product of Example 51 via the corresponding ketone and bromoketone intermediates and coupling with the appropriate thiourea derivative, and other subsequent procedures as similarly exemplified in Example 41. If the name of a compound in the table below is given as a sodium salt, this indicates that the sodium salt was prepared from the acid.

| Ex | Name | Rˣ | Rʸ | LC-MS m/z (acid, M + 1)⁺ |
|---|---|---|---|---|
| 42 | 3-[[4-(1-Isobutyl-cyclopentyl)-thiazol-2-yl]-(5-methyl-thiophen-2-ylmethyl)-amino]-propionic acid | | | 407 |
| 43 | 3-{(5-Ethyl-thiophen-2-ylmethyl)-[4-(1-isobutyl-cyclopentyl)-thiazol-2-yl]-amino}-propionic acid | | | 421 |
| 44 | 3-{(2,5-Dimethyl-thiophen-3-ylmethyl)-[4-(1-isobutyl-cyclopentyl)-thiazol-2-yl]-amino}-propionic acid | | | 421 |
| 45 | Sodium; 3-[[4-(1-ethyl-4-methyl-cyclohexyl)-thiazol-2-yl]-(5-methyl-thiophen-2-ylmethyl)-amino]-propionate | | | 407 |
| 46 | Sodium; 3-[[4-(1,4-dimethyl-cyclohexyl)-thiazol-2-yl]-(5-methyl-thiophen-2-ylmethyl)-amino]-propionate | | | 393 |
| 47 | Sodium; 3-[[4-(1,4-dimethyl-cyclohexyl)-thiazol-2-yl]-(5-ethyl-thiophen-2-ylmethyl)-amino]-propionate | | | 407 |
| 48 | Sodium; 3-[[4-(4-isopropyl-1-methyl-cyclohexyl)-thiazol-2-yl]-(5-methyl-thiophen-2-ylmethyl)-amino]-propionate | | | 421 |
| 49 | Sodium; 3-{(5-ethyl-thiophen-2-ylmethyl)-[4-(4-isopropyl-1-methyl-cyclohexyl)-thiazol-2-yl]-amino}-propionate | | | 435 |

-continued

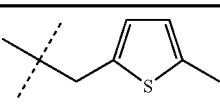

| Ex | Name | R$^x$ | R$^y$ | LC-MS m/z (acid, M + 1)$^+$ |
|---|---|---|---|---|
| 50 | 3-[[4-(4-tert-Butyl-1-methyl-cyclohexyl)-thiazol-2-yl]-(5-methyl-thiophen-2-ylmethyl)-amino]-propionic acid | 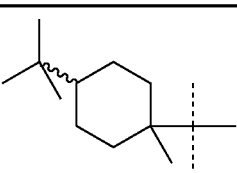 | 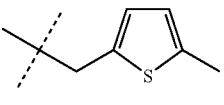 | 435 |
| 51 | 3-[[4-(1-Methyl-4-phenyl-cyclohexyl)-thiazol-2-yl]-(5-methyl-thiophen-2-ylmethyl)-amino]-propionic acid | | 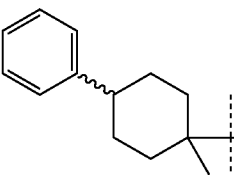 | 455 |

Example 52

3-[[4-(1,4,4-trimethyl-cyclohexyl)-thiazol-2-yl]-(5-methyl-thiophen-2-ylmethyl)-amino]-propionic acid 4,4-dimethylcyclohexanone was converted by a five-step process into 1-(1,4,4-trimethylcyclohexyl)ethanone. The five-step process is similar to that given in Example 53, but also includes an aldehyde alkylation step using LDA and MeI. The Wittig reagent generated as in Example 53 from (methoxymethyl)triphenylphosphonium chloride (1 eq, 24 mmol) and NaH (1 eq, 24 mmol) in THF (100 mL) was used to form the enol ether product from 4,4-dimethylcyclohexanone (3.0 g, 24 mmol): (4-methoxymethylene-1,1-dimethyl-cyclohexane).

This enol ether (2.5 g, 16 mmol) was hydrolyzed by stirring in TFA:DCM (10 mL, 80:20) at RT for 20 min to generate the corresponding aldehyde (2.0 g) after workup and isolation (involving solvent evaporation under vacuum, partitioning of the residue between aq saturated sodium bicarbonate solution and EtOAc, drying of the organic layer over sodium sulfate, and solvent removal at reduced pressure). A portion of this aldehyde (1.0 g, 1 eq) was dissolved in THF (15 mL) and the solution was cooled to −78° C. A solution of LDA (1.5 eq) was added slowly to the mixture and the reaction was stirred for 30 min, then methyl iodide (1.5 eq) was added and the reaction was allowed to warm to room temperature and was stirred overnight. The reaction mixture was added to water and the product was extracted with EtOAc. Evaporation of the solvent gave the crude material, which was purified to give 1,4,4-trimethylcyclohexanecarboxaldehyde (500 mg). This alkylated aldehyde (500 mg, 1 eq) was dissolved in THF and the solution was cooled to 0° C. in an ice bath. A MeMgBr (1.5 eq) solution in THF was added and the reaction was allowed to come to RT overnight. The reaction was quenched with 2N HCl and the aq portion was extracted with EtOAc to give the methylcarbinol derivative (250 mg) after drying, evaporation of the solvent, and purification.

Oxidation of this material (250 mg) using PCC (1.5 eq) in DCM (5 mL) gave the desired 1-(1,4,4-trimethylcyclohexyl) ethanone. Also in an analogous fashion to the process disclosed in Example 53, this methylketone derivative (200 mg, 1 eq) was then treated with pyrrolidone hydrotribromide (1.1 eq) in MeOH (5 mL) to give the 2-bromoketone derivative (190 mg) after workup. This bromoketone intermediate (100 mg, 1 eq) was subsequently treated with the appropriate thiourea derivative (1.1 eq) in MeOH (3 mL) to produce the desired aminothiazole propionate ester derivative (60 mg) after reaction overnight at RT, workup, and chromatography on silica gel. Hydrolysis of the t-butyl ester with NaOH in aq THF: MeOH and purification of the product after acidic workup gave the desired acid (35 mg). LC-MS m/z: 407 (M+1)$^+$. The sodium salt of title compound could be obtained using a method similar to General Method H to generate the sodium carboxylate salt.

Example 53

3-{(5-methyl-thiophen-2-ylmethyl)-[4-(3,3,5,5-tetramethyl-cyclohexyl)-thiazol-2-yl]-amino}-propionic acid

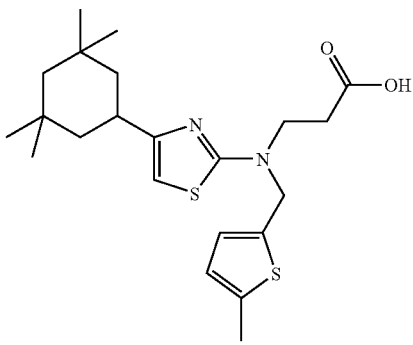 [SMILES: Cc1ccc(CN(CCC(=O)O)c2nc(C3CC(C)(C)CC(C)(C)C3)cs2)s1]

The title compound was prepared by the following method: (Methoxymethyl)triphenylphosphonium chloride (2.7 g, 8.0 mmol) was suspended in toluene and then the toluene was evaporated under vacuum to remove water. The drying process was repeated once more, and then the phosphonium salt was suspended in THF (20 mL). The suspension was cooled to 0° C., and then a suspension of NaH in oil (312 mg, 6.5 mmol; 60% in oil) was added. The reaction was warmed to RT and stirred for 6 hrs to give an orange solution containing a suspended precipitate. The ppt was allowed to settle, then the solution was added to a solution of 3,3,5,5-Tetramethyl-cyclohexanone (1.0 g, 6.5 mmol) in THF. The reaction was stirred overnight at RT, then the reaction was quenched with water and concentrated under vacuum. The material was extracted with EtOAc, and the organic portion was dried over sodium sulfate. The solvent was decanted and evaporated under vacuum to give the crude product which was purified using silica gel chromatography to give 5-methoxymethylene-1,1,3,3-tetramethyl-cyclohexane (800 mg, 67% yield). This enol ether was converted to 3,3,5,5-tetramethyl-cyclohexanecarboxaldehyde (650 mg, 90% yield) following a method analogous to General Procedure L by stirring at RT in trifluoroacetic acid:dichloromethane (10 mL, 8:2) solution for 20 mins, then evaporating the solvent under vacuum, partitioning the residue between EtOAc and saturated aq sodium bicarbonate solution, washing the organic portion with saturated aq sodium bicarbonate solution, drying the organic portion, and evaporating the solvent under reduced pressure.

The crude 3,3,5,5-Tetramethyl-cyclohexanecarboxaldehyde (650 mg, 3.8 mmol) was treated with methylmagnesium bromide (4.5 mmol, 1.2 eq) in THF (20 mL) at 0° C., and allowing to warm to RT following a method analogous to General Procedure I to produce 1-(3,3,5,5-tetramethyl-cyclohexyl)-ethanol (400 mg) after quenching the reaction at 0° C. with 2N HCl, extraction of the product with EtOAc, and evaporation of the solvent under vacuum. The crude material was used without purification in the next step.

The above alcohol was converted to 1-(3,3,5,5-tetramethyl-cyclohexyl)-ethanone (250 mg) following a method analogous to General Procedure J using PCC (3.0 mmol, 1.5 eq) in DCM (10 mL) and stirring at RT overnight. Filtration through Celite® and concentration of the filtrate under vacuum gave the desired ketone.

Treatment of this ketone product (250 mg, 1.3 mmol) with pyrrolidone hydrotribromide (709 mg, 1.4 mmol) in methanol (5 mL) at RT overnight following a method analogous to General Procedure B1 gave 2-bromo-1-(3,3,5,5-tetramethyl-cyclohexyl)-ethanone (245 mg, 72% yield) after evaporation of the solvent, partitioning the residue between EtOAc and saturated aq sodium bicarbonate solution, washing the organic portion with saturated aq sodium bicarbonate solution, drying the organic portion and concentrating the solution under vacuum. This material was used in crude form for the next step.

The above obtained 2-bromo ketone was reacted with 3-[1-(5-methyl-thiophen-2-ylmethyl)-thioureido]-propionic acid tert-butyl ester (132 mg, 0.42 mmol) by stirring in methanol (3 mL) at RT for 5 hr following a method analogous to General Procedure C to afford 3-{(5-methyl-thiophen-2-ylmethyl)-[4-(3,3,5,5-tetramethyl-cyclohexyl)-thiazol-2-yl]-amino}-propionic acid tert-butyl ester (60 mg, 33% yield) after evaporation of the solvent, workup and purification.

3-{(5-methyl-thiophen-2-ylmethyl)-[4-(3,3,5,5-tetramethyl-cyclohexyl)-thiazol-2-yl]-amino}-propionic acid tert-butyl ester (60 mg, 0.12 mmol) was treated with NaOH (2N NaOH: 1 mL; MeOH: 1 mL; THF: 1 mL) and the reaction was heated at 50° C. for 3 hrs following a method analogous to General Procedure G1 to produce 3-{(5-methyl-thiophen-2-ylmethyl)-[4-(3,3,5,5-tetramethyl-cyclohexyl)-thiazol-2-yl]-amino}-propionic acid (25 mg) after workup and purification. LC-MS m/z: 421 (M+1)$^+$. $^1$H NMR (400 MHz, CDCl$_3$): δ 6.81 (d, 1H), 6.60 (d, 1H), 6.12 (s, 1H), 4.60 (S, 2H), 3.75-3.80 (m, 2H), 2.92 (m, 1H), 2.68-2.73 (m, 2H), 2.44 (s, 3H), 1.73 (d, 2H), 1.27-1.32 (m, 1H), 1.00-1.17 (m, 3H), 1.07 (s, 6H), 0.93 (s, 6H). The sodium carboxylate salt of the title compound could be prepared from this acid using a method analogous to General Procedure H.

The compounds listed in the Examples 54, 55 and 56 below were made starting from a common cyclohexanone precursor. For the synthesis of the compounds in Examples 54 and 55 below, 4,4-dimethylcyclohexanone was converted by a four-step process into 1-(4,4-dimethylcyclohexyl)ethanone. The 4-step process is similar to that given in Example 53: the Wittig reagent generated as in Example 53 from (methoxymethyl)triphenylphosphonium chloride and NaH in THF was used to form the corresponding enol ether product from 4,4-dimethylcyclohexanone: (4-methoxymethylene-1,1-dimethyl-cyclohexane). This enol ether was hydrolyzed using TFA:DCM to generate the corresponding aldehyde. This aldehyde was treated with MeMgBr in THF/Et$_2$O to give a methylcarbinol derivative which was then oxidized using PCC in DCM to give the desired 1-(4,4-dimethylcyclohexyl)ethanone. Also in an analogous fashion to the process disclosed in Example 53, this ketone was then treated with pyrrolidone hydrotribromide to give the 2-bromoketone derivative, and this bromoketone intermediate was subsequently treated with the appropriate thiourea derivatives in MeOH to produce the products shown in Examples 54 and 55 after hydrolysis of the esters, purification of the acids, and generation of the sodium carboxylate salts.

For the synthesis of the compound shown in Example 56, the aldehyde intermediate from the above procedure was treated with ethyl magnesium bromide instead of methyl magnesium bromide in THF to generate an ethyl carbinol intermediate. This intermediate was used to generate the ethyl ketone by PCC oxidation in an analogous fashion to the method given in Example 53. The ethyl ketone was treated with pyrrolidone hydrotribromide in MeOH to give the bromoketone derivative, and this material was reacted with the appropriate thiourea derivative in MeOH to produce the product shown in Example 56 after hydrolysis of the ester, purification of the acid, and generation of the sodium carboxylate salt. If the name of a compound in the table below is given as a sodium salt, this indicates that the sodium salt was prepared from the acid.

| Ex | Name | R$^x$ | R$^y$ | R$^z$ | LC-MS m/z (acid, M + 1)$^+$ |
|---|---|---|---|---|---|
| 54 | 3-[[4-(4,4-Dimethyl-cyclohexyl)-thiazol-2-yl]-(5-ethyl-thiophen-2-ylmethyl)-amino]-propionic acid | | | H | 407 |
| 55 | 3-[[4-(4,4-Dimethyl-cyclohexyl)-thiazol-2-yl]-(5-methyl-thiophen-2-ylmethyl)-amino]-propionic acid | | | H | 393 |
| 56 | Sodium; 3-[[4-(4,4-dimethyl-cyclohexyl)-5-methyl-thiazol-2-yl]-(5-methyl-thiophen-2-ylmethyl)-amino]-propionate | | | Me | 407 |

Example 57

3-{(5-Methyl-thiophen-2-ylmethyl)-[4-(octahydro-inden-2-yl)-thiazol-2-yl]-amino}-propionic acid

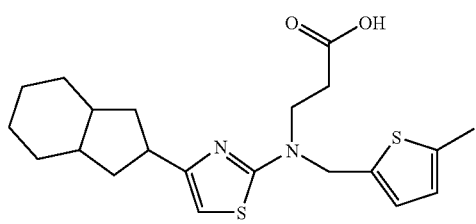 [SMILES: Cc1ccc(CN(CCC(=O)O)c2nc(C3CC4CCCCC4C3)cs2)s1]

An acetic acid solution of indan-2-carboxylic acid (500 mg, 3.0 mmol) was stirred under hydrogen pressure (40 psi) in the presence of a small amount of PtO$_2$ in a sealed glass pressure vessel equipped with a manometer and pressure valve following a method analogous to General Procedure M to produce octahydro-indene-2-carboxylic acid (490 mg, 95% yield) as a mixture of isomers.

Octahydro-indene-2-carboxylic acid (490 mg, 2.92 mmol) was treated with MeLi following a method analogous to General Procedure A1 to produce the corresponding methyl ketone. The methyl ketone in MeOH was then treated with pyrrolidone hydrotribromide following a method analogous to General Procedure B1 to produce 2-bromo-1-(octahydro-inden-2-yl)-ethanone (600 mg, 84% overall crude yield). The above obtained bromoketone (150 mg, 0.61 mmol) was treated with 3-[1-(5-methyl-thiophen-2-ylmethyl)-thioureido]-propionic acid tert-butyl ester (150 mg) following a method analogous to General Procedure C to produce the aminothiazole propionic acid ester: 3-{(5-methyl-thiophen-2-ylmethyl)-[4-(octahydro-inden-2-yl)-thiazol-2-yl]-amino}-propionic acid tert-butyl ester.

The above obtained tert-butyl propionate ester derivative was hydrolyzed using NaOH following a method analogous to General Procedure G1 to produce 3-{(5-methyl-thiophen-2-ylmethyl)-[4-(octahydro-inden-2-yl)-thiazol-2-yl]-amino}-propionic acid (75 mg). LC-MS m/z: 405 (M+1)$^+$. $^1$H NMR (400 MHz, CDCl$_3$): δ6.81 (m, 1H), 6.60 (m, 1H), 6.15-6.12 (2s, 1H), 4.60 (m, 2H), 3.75 (m, 2H), 3.41-3.10 (2m, 1H), 2.70 (m, 2H), 2.43 (2s, 3H), 2.20-1.20 (m, 14H). The corresponding sodium carboxylate salt of the title compound could be prepared using a method analogous to General Procedure H.

Examples 58 and 59 in the table below were prepared starting from the above octahydroindene-2-carboxylic acid and the appropriate N,N-disubstituted thiourea derivatives following methods analogous to the synthetic procedures described for Example-57.

The methylketone starting material for Example 60 in the table below was prepared from trans-4-(4-chlorophenyl)cyclohexyl-1-ethanone (1 g, 4.2 mmol) in two steps. Hydrogenation of the aromatic ring with concomitant reduction of the aromatic ketone to the alcohol and concomitant hydrogenolysis of the carbon-chlorine bond was accomplished using hydrogen gas ($H_2$ pressure=50 psi) in a resealable glass pressure vessel equipped with a manometer and pressure valve. The reaction was stirred under $H_2$ pressure for 2 days in MeOH:AcOH (1:1; 6 mL) using $PtO_2$ (200 mg) as the catalyst to effect the desired transformation. Filtration through Celite® and evaporative workup gave the crude alcohol product (900 mg) which was used as-is in the preparation of the corresponding ketone by oxidation with PCC (6.3 mmol, 1.5 eq), the reaction being effected by stirring overnight in DCM containing molecular sieves (about 100 mg) at RT. The [4-(cyclohexyl)-cyclohexyl]methylketone product (700 mg) was isolated after workup and filtration through a silica gel column to remove impurities.

A portion of this [4-(cyclohexyl)-cyclohexyl]methylketone (100 mg, 0.5 mmol) was then brominated by heating with pyrrolidone hydrotribromide (260 mg, 1.05 eq) in MeOH (3 mL) at 50° C. for 2-3 hours. The 2-bromoketone intermediate (120 mg) was isolated after workup and was used as the crude material for the next step. Treatment with the appropriate thiourea derivative (145 mg, 0.46 mmol, 1.1 eq) gave the aminothiazole propionic acid ester intermediate (150 mg) and subsequent hydrolysis yielded the desired propionic acid (90 mg). Preparation of the corresponding sodium carboxylate salt using a procedure similar to General Procedure H yielded the compound of Example 60.

If the name of a compound in the table below is given as a sodium salt, this indicates that the sodium salt was prepared from the acid.

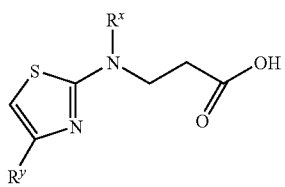

| Ex | Name | $R^x$ | $R^y$ | LC-MS m/z (acid, M + 1)$^+$ |
|----|------|-------|-------|------------------------------|
| 58 | 3-{(5-Ethyl-thiophen-2-ylmethyl)-[4-(octahydro-inden-2-yl)-thiazol-2-yl]-amino}-propionic acid | | | 419 |
| 59 | 3-{(2,5-Dimethyl-thiophen-3-ylmethyl)-[4-(octahydro-inden-2-yl)-thiazol-2-yl]-amino}-propionic acid | | | 419 |
| 60 | Sodium; 3-[(4-bicyclohexyl-4-yl-thiazol-2-yl)-(5-methyl-thiophen-2-ylmethyl)-amino]-propionate | | | 447 |

Example 61

Sodium; 3-[{4-[4-(4-fluoro-phenyl)-cyclohexyl]-thiazol-2-yl}-(5-methyl-thiophen-2-ylmethyl)-amino]-propionate

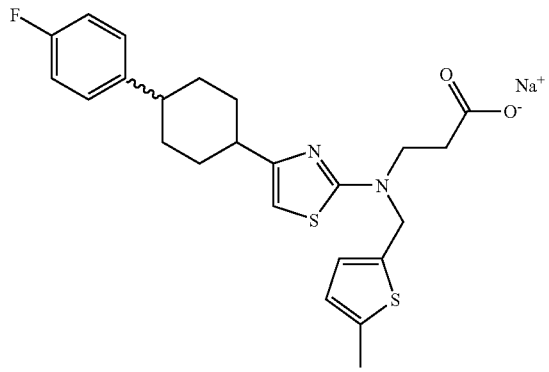 [SMILES: Cc1ccc(CN(CCC(=O)[O-])c2nc(C3CCC(c4ccc(F)cc4)CC3)cs2)s1 ; [Na+]]

(See: Karamysheva, L. A., Torgova, S. I., Agafonova, I. F., Geivandov, R. K., Bykova, V. V., Burylin, P. A., Journal of Organic Chemistry of the USSR, 28 (1), no. 5, pp. 736-741 (1992)).

To a fluorobenzene (5 mL) solution of cyclohexene (82 mg, 1 mmol) at RT was added acetyl chloride (86 mg, 1.1 mmol) and then the reaction was cooled in an ice bath. Aluminum chloride (150 mg, 1.1 mmol) was slowly added to the solution, then the reaction was slowly allowed to warm to room temperature, was stirred at room temperature for 24 h and was then heated to 80° C. for 1 h. The reaction mixture was cooled to room temperature and was then slowly added to ice cold water. The mixture was extracted with ethyl acetate and the organic portion was dried over sodium sulfate, concentrated under vacuum, and purified on a silica gel column to afford 1-[4-(4-fluoro-phenyl)-cyclohexyl]-ethanone containing about 30% of another unidentified substance (176 mg).

The above impure ketone was brominated using pyrrolidone hydrotribromide (262 mg, 0.84 mmol) in methanol (3 mL) following a method analogous to General Procedure B1 to afford 2-bromo-1-[4-(4-fluoro-phenyl)-cyclohexyl]-ethanone contaminated with about 30% of an unknown substance (215 mg). This impure bromo ketone was treated with 3-[1-(5-methyl-thiophen-2-ylmethyl)-thioureido]-propionic acid tert-butyl ester (248 mg, 0.79 mmol) in methanol (3 mL) following a method analogous to General Procedure C to afford 3-[{4-[4-(4-Fluoro-phenyl)-cyclohexyl]-thiazol-2-yl}-(5-methyl-thiophen-2-ylmethyl)-amino]-propionic acid tert-butyl ester containing about 30% of an unidentified substance (220 mg).

The above obtained tert-butyl propionate derivative was hydrolyzed with NaOH following a method analogous to General Procedure G1 to produce 3-[{4-[4-(4-fluoro-phenyl)-cyclohexyl]-thiazol-2-yl}-(5-methyl-thiophen-2-ylmethyl)-amino]-propionic acid containing about 30% of an unidentified substance (155 mg). LC-MS m/z: 459 (M+1)$^+$. $^1$H NMR (400 MHz, CDCl$_3$): δ 7.67 (m, 1H), 7.56-7.61 (m, 1H), 7.00 (m, 1H), 6.84 (d, 1H), 6.65 (s, 1H), 6.60 (m, 1H), 5.23 (s, 1H), 4.75 (s, 2H), 3.82 (t, 2H), 2.83-2.92 (m, 1H), 2.79 (t, 2H), 2.43 (s, 3H), 1.8-1.92 (m, 3H), 1.7-1.80 (m, 2H), 1.39-1.54 (m, 4H). The sodium salt of the carboxylate (title compound) was prepared using a method analogous to General Procedure H, yielding sodium 3-[{4-[4-(4-fluoro-phenyl)-cyclohexyl]-thiazol-2-yl}-(5-methyl-thiophen-2-ylmethyl)-amino]-propionate containing about 30% of an unidentified impurity (155 mg).

Example 62

3-[(5-methyl-thiophen-2-ylmethyl)-(4-spiro[4.5]dec-8-yl-thiazol-2-yl)-amino]-propionic acid

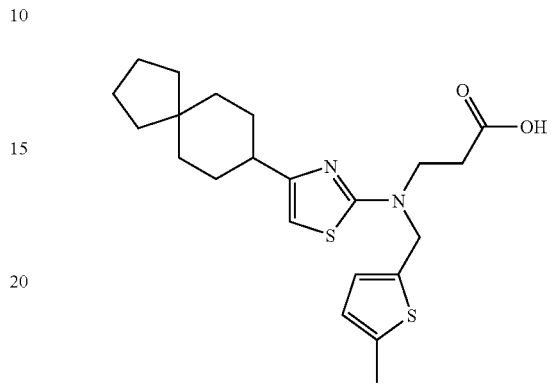

To a stirred solution of (1-carboxymethyl-cyclopentyl)-acetic acid (1.0 g, 5.3 mmol) at 0° C. was added borane in THF (20 mL, 1.0 M; 20 mmol) and the resultant reaction mixture was stirred and allowed to come to RT overnight. The reaction mixture was cooled in an ice bath and quenched by dropwise addition of methanol (about 5 mL). The solvent was evaporated under reduced pressure and the residue was partitioned between aqueous sodium bicarbonate and ethyl acetate (about 50 mL, 1:1). The organic phase was dried over Na$_2$SO$_4$, concentrated under reduced pressure and filtered through a bed of silica gel to afford 2-[1-(2-hydroxy-ethyl)-cyclopentyl]-ethanol (800 mg) after evaporation of the eluent.

To a dichloromethane (20 mL) solution of the above diol (800 mg, 5.0 mmol) in an ice bath was added PBr$_3$ (3.0 g, 11 mmol) dropwise under nitrogen. The reaction was slowly warmed to room temperature then was refluxed for about 15 h. Progress of the reaction was monitored by TLC. The reaction was cooled in an ice bath and cold aqueous sodium bicarbonate was added. The two layers were separated and the aqueous phase was extracted with dichloromethane once. The combined organic layers were dried with Na$_2$SO$_4$, concentrated under reduced pressure, and filtered through a bed of silica gel (eluent: hexane:EtOAc, 1:1) to afford the bis-bromide (1.3 g).

To a dimethylformamide (2 mL) solution of 3-oxo-butyric acid ethyl ester (0.06 mL, 0.5 mmol) under nitrogen in an ice bath was added an oil suspension of NaH (60 mg, 1.5 mmol, 3.0 eq). The reaction was stirred at 0° C. for 20 min followed by a slow addition of the above bis-bromide (200 mg, 0.7 mmol). The reaction was slowly warmed to room temperature and then heated to 60-70° C. for 2 h. The reaction mixture was cooled to room temperature, and water was slowly added. The mixture was extracted with ethyl acetate (2× about 15 mL). The combined organic phases were washed with water and then brine, and were then dried over Na$_2$SO$_4$, and concentrated under reduced pressure to give 1-spiro[4.5]dec-8-yl-ethanone (120 mg).

1-Spiro[4.5]dec-8-yl-ethanone (120 mg, 0.66 mmol) was treated with pyrrolidone hydrotribromide (360 mg, 0.72 mmol) in methanol (3 mL) following a method analogous to General Procedure B1 to produce 2-bromo-1-spiro[4.5]dec-8-yl-ethanone (120 mg). This bromo ketone was used without further purification. It was treated with 3-[1-(5-methyl-thiophen-2-ylmethyl)-thioureido]-propionic acid tert-butyl ester (158 mg, 0.5 mmol) following a method analogous to General Procedure C to afford 3-[(5-methyl-thiophen-2-ylmethyl)-(4-spiro[4.5]dec-8-yl-thiazol-2-yl)-amino]-propionic acid tert-butyl ester after workup and purification (30 mg).

Hydrolysis of the above obtained propionate ester derivative (30 mg, 0.06 mmol) with NaOH (0.5 mL of a 2.0N aq solution added to 1 mL of MeOH:THF:1:1) following a method analogous to General Procedure G1 gave 3-[(5-methyl-thiophen-2-ylmethyl)-(4-spiro[4.5]dec-8-yl-thiazol-2-yl)-amino]-propionic acid (10 mg). LC-MS m/z: 419 (M+1)$^+$. $^1$H NMR (400 MHz, CDCl$_3$): δ 6.80 (d, 1H), 6.59 (d, 1H), 6.11 (s, 1H), 4.60 (s, 2H), 3.75 (t, 2H), 2.71 (t, 2H), 2.51 (m, 1H), 2.43 (s, 3H), 1.80-1.86 (m, 2H), 1.20-1.64 (m, 14H). The corresponding sodium carboxylate salt of the title compound could be prepared following a method analogous to General Procedure H.

Example 63

3-[(5-methyl-thiophen-2-ylmethyl)-(4-spiro[5.5]undec-3-yl-thiazol-2-yl)-amino]-propionic acid

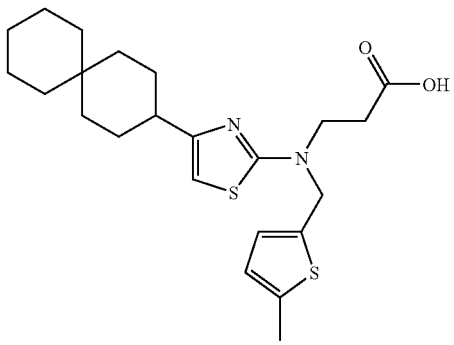 [SMILES: Cc1ccc(CN(CCC(=O)O)c2nc(C3CCC4(CCCCC4)CC3)cs2)s1]

(1-Carboxymethyl-cyclohexyl)-acetic acid was converted to 2-bromo-1-spiro[5.5]undec-3-yl-ethanone following a sequence of procedures similar to those described in Example 62 for the preparation of 2-bromo-1-spiro[4.5]dec-8-yl-ethanone.

2-bromo-1-spiro[5.5]undec-3-yl-ethanone (200 mg, 0.7 mmol) in MeOH (2 mL) was treated with 3-[1-(5-methyl-thiophen-2-ylmethyl)-thioureido]-propionic acid tert-butyl ester (250 mg, 0.8 mmol) following a method analogous to General Procedure C to produce 3-[(5-methyl-thiophen-2-ylmethyl)-(4-spiro[5.5]undec-3-yl-thiazol-2-yl)-amino]-propionic acid tert-butyl ester after workup and purification (45 mg). This propionate ester derivative (45 mg, 0.09 mmol) was hydrolyzed using NaOH (0.5 mL of 2.0N aq solution in 1 mL of 1:1:MeOH:THF) following a method analogous to General Procedure G1 to produce 3-[(5-methyl-thiophen-2-ylmethyl)-(4-spiro[5.5]undec-3-yl-thiazol-2-yl)-amino]-propionic acid after workup (15 mg, 33% yield). LC-MS m/z: 433 (M+1)$^+$. $^1$H NMR (400 MHz, CDCl$_3$): δ 6.80 (d, 1H), 6.59 (d, 1H), 6.11 (s, 1H), 4.60 (s, 2H), 3.75 (t, 2H), 2.71 (t, 2H), 2.51 (m, 1H), 2.43 (s, 3H), 1.82 (m, 2H), 1.71 (m, 2H), 1.50 (m, 2H), 1.3-1.5 (m, 7H), 1.27-1.13 (m, 5H). Sodium salt of the title compound could be prepared from the title compound following a method analogous to General Procedure H.

Example 64

3-[[4-(4,4-dimethyl-cyclohexylmethyl)-thiazol-2-yl]-(5-methyl-thiophen-2-ylmethyl)-amino]-propionic acid

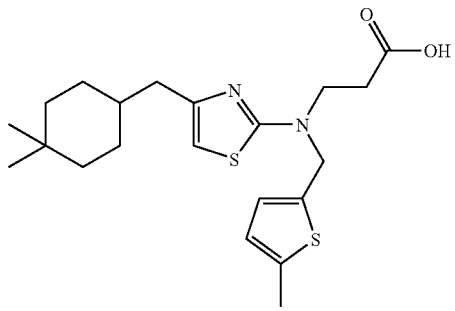 [SMILES: Cc1ccc(CN(CCC(=O)O)c2nc(CC3CCC(C)(C)CC3)cs2)s1]

To a toluene (5 mL) solution containing 4,4-dimethyl-cyclohexanone (500 mg, 4.0 mmol) was added methyl (triphenylphosphoranylidene)acetate (2.0 g, 6.0 mmol) and the reaction was heated to 60-70° C. for 48 h. The reaction was monitored by TLC. The reaction was cooled to room temperature, diluted with dichloromethane, washed with water, concentrated under vacuum, and the crude product was purified on a silica gel column to afford (4,4-dimethyl-cyclohexylidene)-acetic acid methyl ester (100 mg, 14% yield).

To a stirred solution of the above alkene (100 mg, 0.54 mmol) in a mixture of ethyl acetate-methanol (0.8 mL, 1:1) was added Pd—C (10 mg, 20% on activated carbon) and the resultant mixture was stirred under hydrogen pressure (50 psi) for 2 h in a resealable glass pressure vessel equipped with a manometer and pressure valve. The catalyst was filtered off using a pad of Celite® and the Celite® pad was washed with an ethyl acetate-methanol mixture (1:1, about 10 mL). The combined filtrate was concentrated under reduced pressure to give the desired (4,4-dimethyl-cyclohexyl)-acetic acid methyl ester (80 mg).

Hydrolysis of (4,4-dimethyl-cyclohexyl)-acetic acid methyl ester (80 mg, 0.43 mmol) with NaOH following a method analogous to General Procedure G1 gave (4,4-dimethyl-cyclohexyl)-acetic acid after purification (70 mg, 95% yield). This acid (70 mg) was converted to 1-(4,4-dimethyl-cyclohexyl)-propan-2-one (60.0 mg, 89% yield) using MeLi in ethyl ether following a method analogous to General Procedure A1. Pyrrolidone hydrotribromide (190 mg, 0.38 mmol) treatment of the above ketone following a method analogous to General Procedure B1 gave 1-bromo-3-(4,4-dimethyl-cyclohexyl)-propan-2-one (70 mg).

The above obtained 2-bromo ketone was treated with 3-[1-(5-methyl-thiophen-2-ylmethyl)-thioureido]-propionic acid tert-butyl ester (100 mg, 0.3 mmol) in methanol (3 mL) following a method analogous to General Procedure C to produce 3-[[4-(4,4-dimethyl-cyclohexylmethyl)-thiazol-2-yl]-(5-methyl-thiophen-2ylmethyl)-amino]-propionic acid tert-butyl ester, which was purified by silica gel chromatography (40 mg).

The tert-butyl propionate ester derivative above was treated with NaOH following a method analogous to General Procedure G1 to produce 3-[[4-(4,4-dimethyl-cyclohexylmethyl)- thiazol-2-yl]-(5-methyl-thiophen-2-ylmethyl)-amino]-propionic acid (20 mg) after workup. $^1$H NMR (400 MHz, CDCl$_3$): δ 6.81 (d, 1H), 6.60 (d, 1H), 6.12 (s, 1H), 4.61 (s, 2H), 3.75 (t, 2H), 2.70 (t, 2H), 2.46 (d, 2H), 2.44 (s, 3H), 1.50-1.65 (m, 2H), 1.32-1.37 (m, 2H), 1.25-1.32 (m, 1H), 1.12-1.22 (m, 4H), 0.88 (s, 3H), 0.86 (s, 3H). The sodium salt of the title compound could be prepared following a method analogous to General Procedure H.

Comparative Compounds

Compounds other than Examples 1-64 are referenced in the biological assays below. These reference compounds are listed below and may be prepared by methods similar to those described above or by methods described in PCT International Publication No. WO/2005/103022.

Reference Compound A: Sodium 3-{[4-(4-isopropyl-phenyl)-thiazol-2-yl]-thiophen-2-ylmethyl-amino}-propionate

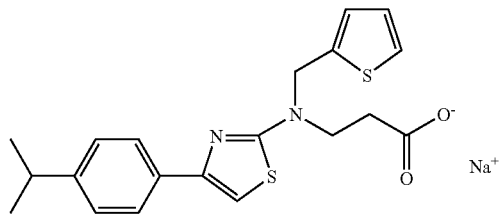 [SMILES: CC(C)c1ccc(-c2csc(N(CCC(=O)[O-])Cc3cccs3)n2)cc1 ; [Na+]]

Reference Compound B: Sodium 3-[(4-biphenyl-4-yl-thiazol-2-yl)-thiophen-2-ylmethylamino]-propionate

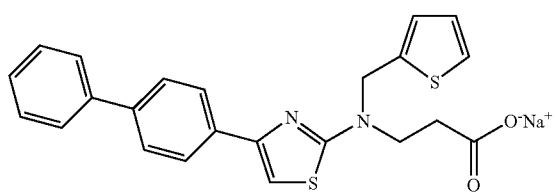

Reference Compound C: Sodium 3-({4-[4-(trans-4-methyl-cyclohexyloxy)-phenyl]-thiazol-2-yl}-thiophen-2-ylmethyl-amino)-propionate

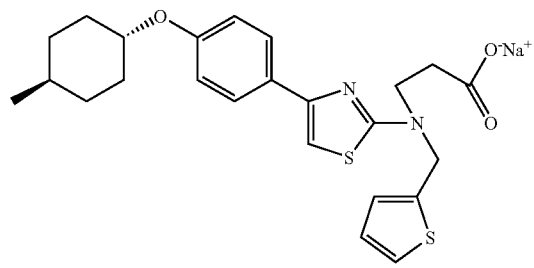

Reference Compound D: Sodium 3-[[4-(trans-4-tert-butyl-cyclohexyl)-thiazol-2-yl]-(thiophen-2-ylmethyl)-amino]-propionate

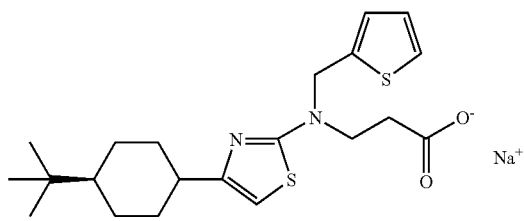

Reference Compound E: Sodium 3-[[4-(trans-4-phenyl-cyclohexyl)-thiazol-2-yl]-(5-thiophen-2-ylmethyl)-amino]-propionate

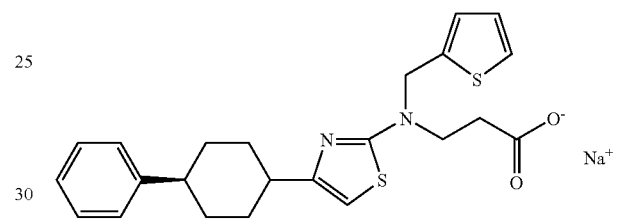

Reference Compound F: Sodium 3-[[4-(4-(pyrrolidin-1-yl)-phenyl)-thiazol-2-yl]-(5-thiophen-2-ylmethyl)-amino]-propionate

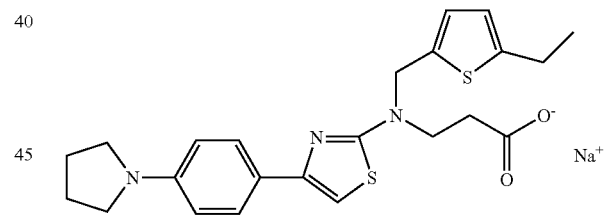

Biological Assay

The following method is illustrative of techniques that may be employed to measure the ability of the compounds of Formula (I) to functionally modulate the binding of AgRP to melanocortin receptors. In particular, the assay below measures the ability of compounds of Formula (I) or pharmaceutically acceptable salts thereof to functionally modulate the binding of AgRP to MC-4R in the presence of a MC-4R agonist, such as alpha-MSH.

Cell Culture and Maintenance

HEK293 cells stably expressing human MC-4R receptors were grown in high glucose Dulbecco's Modified Eagle Medium (DMEM) with 4500 mg glucose/L, L-glutamine, NaHCO$_3$, pyrdoxin HCl, 10 mM HEPES (pH 7.4), 0.1 mM NEAA (non-essential amino acid medium) (GIBCO Cat#11140-050), 10% fetal bovine serum and 700 μg/mL G418. Cells were grown in T-225 flasks at 37° C. with CO$_2$ and humidity control.

Assay

On the day of assay, cells were washed twice with phosphate buffered saline without calcium and magnesium (PBS) and incubated with 10 mL PBS until the cells were detached from the flask. The detached cells were centrifuged at 240 g for 5 min. The cell pellet was re-suspended in assay buffer (Earle's balanced salt solution (Sigma E3024) supplemented with 10 mM HEPES, pH 7.4, 0.5 mM IBMX and protease inhibitor cocktail (Roche, 1 complete tablet/75 mL buffer)).

The inhibitory or enhancement effect of compounds on AgRP activity was measured in a multi-component assay containing testing compounds, AgRP$_{83-132}$ (human, Phoenix Pharma, cat no. 003-53), cells expressing MC-4R, and αMSH (Bachem, cat no. H-1075). Test compounds, AgRP and αMSH were diluted with assay buffer. Test compounds and AgRP were mixed to 4 times of the final concentration and incubated at room temperature for 30 min. Five μL of testing compound/AgRP solution followed with 10 μL of cells (20,000 cells/well) were added to each well of a 384-well reaction plate before 5 μL of αMSH was added. Cells were stimulated with αMSH for an additional 30 min at 37° C.

Stimulation of cells was stopped by adding a lysis buffer and cells were lysed. The intracellular concentration of cAMP may be measured by various techniques known to one of skill in the art including, but not limited to, fluorescence polarization (FP) and time-resolved fluorescence (TRF).

Compounds of Examples 1-64 inhibit the functional interaction of AgRP with MC-4R. The inhibition was shown by an increase in MC-4R mediated cAMP production. Such compounds possess an effective concentration for half maximal effect (EC50) in the assay of less than 5 μM. For specific EC50's of a particular Example, see Table 1 below.

Control Assay 1

In a control experiment, the direct effect of the test compounds on cells (referred to as basal activity) may be measured in the absence of AgRP and αMSH. Briefly, 10 μl of a test compound in assay buffer and 10 μl of cells (20,000 cells/well), in the same buffer may be added to each well of a 384-well reaction plate and incubated at 37° C. for 30 min. The reaction is stopped by adding a lysis buffer, the cells are lysed, and the intracellular concentration of cAMP is measured. Based on control assays on one or more related compounds, the compounds of Examples 1-64 are expected to show minimal activity in inducing cAMP production of MC-4R expressing cells under such conditions.

Control Assay 2

The potentiating effect of test compounds on αMSH activity may also be measured. Five μL of a test compound solution in assay buffer may be mixed with 10 μL cells (20,000 cells/well) and incubated at 37° C. for 15 min before 5 μL αMSH solution is added. Cells are stimulated with a sub-maximal concentration of αMSH at 37° C. for additional 30 min. The reaction is stopped by adding a lysis buffer, the cells are lysed, and the intracellular concentration of cAMP is measured. Based on control assays on one or more related compounds, the compounds of Examples 1-64 are expected to show minimal effect on αMSH induced cAMP production in the MC-4R expressing cells under such conditions.

TABLE 1

| Example | Average EC50 (nM) in Biological Assay |
|---|---|
| 1 | 126 |
| 2 | 135 |
| 3 | 246 |

TABLE 1-continued

| Example | Average EC50 (nM) in Biological Assay |
|---|---|
| 4 | 324 |
| 5 | 241 |
| 6 | 250 |
| 7 | 159 |
| 8 | 210 |
| 9 | 274 |
| 10 | 260 |
| 11 | 252 |
| 12 | 384 |
| 13 | 528 |
| 14 | 602 |
| 15 | 221 |
| 16 | 205 |
| 17 | 259 |
| 18 | 416 |
| 19 | 386 |
| 20 | 389 |
| 21 | 372 |
| 22 | 394 |
| 23 | 366 |
| 24 | 79 |
| 25 | 80 |
| 26 | 276 |
| 27 | 114 |
| 28 | 171 |
| 29 | 427 |
| 30 | 3887 |
| 31 | 1575 |
| 32 | 2276 |
| 33 | 1233 |
| 34 | 269 |
| 35 | 132 |
| 36 | 267 |
| 37 | 524 |
| 38 | 145 |
| 39 | 275 |
| 40 | 219 |
| 41 | 58 |
| 42 | 116 |
| 43 | 173 |
| 44 | 191 |
| 45 | 159 |
| 46 | 76 |
| 47 | 58 |
| 48 | 73 |
| 49 | 102 |
| 50 | 154 |
| 51 | 143 |
| 52 | 267 |
| 53 | 307 |
| 54 | 36 |
| 55 | 70 |
| 56 | 217 |
| 57 | 187 |
| 58 | 94 |
| 59 | 160 |
| 60 | 191 |
| 61 | 246 |
| 62 | 321 |
| 63 | 283 |
| 64 | 90 |

Stability in Liver Microsomes

Various compounds were tested for their stability in human, monkey, dog, rat, and mouse liver microsomes. At a final concentration of 1 μM, compounds were incubated with either human, monkey, dog, rat, or mouse liver microsomes (0.5 mg protein/mL) in the presence of an NADPH-solution for 60 minutes at 37° C., pH 7.4 in phosphate buffer. Incubations were performed in duplicate. Reactions were terminated by the addition of methanol. The incubation solution was vortexed and transferred into a 96-well plate. The plate was sealed and centrifuged at approximately 3500 rpm for approximately 10 minutes. After centrifugation, the plate was loaded into 96-well plate autosampler and analyzed by LC/MS. Values are reported as percent of compound remaining after 1 hour. Table 2 lists the compounds of Examples 1-64 that were screened for microsomal stability. Those compounds of Examples 1-64 not listed in Table 2 were not tested. Table 3 lists additional compounds that were screened for microsomal stability.

TABLE 2

Stability in Liver Microsomes (% remaining after 1 hour incubation)

| Example | Human | Monkey | Dog | Rat | Mouse |
|---------|-------|--------|-----|-----|-------|
| 7 | 78 | 67 | 66 | 57 | 68 |
| 8 | 93 | 84 | 91 | 88 | 88 |
| 9 | 82 | 74 | 92 | 66 | 69 |
| 19 | 43 | 60 | 87 | 52 | 73 |
| 21 | 84 | 47 | 78 | 66 | 86 |
| 23 | 71 | 56 | 94 | 15 | 60 |
| 25 | 99 | 77 | 69 | 69 | 81 |
| 26 | 79 | 67 | 72 | 66 | 71 |
| 31 | 83 | 88 | 94 | 83 | 91 |
| 38 | 71 | 70 | 93 | 90 | 99 |
| 40 | 61 | 85 | 36 | 67 | 90 |
| 55 | 49 | 78 | 80 | 64 | 68 |
| 60 | 92 | 83 | 99 | 86 | 87 |
| 61 | 68 | 13 | 84 | 40 | 74 |

TABLE 3

Stability in Liver Microsomes (% remaining after 1 hour incubation)

| Example | Human | Monkey | Dog | Rat | Mouse |
|---------|-------|--------|-----|-----|-------|
| A | 40 | 2 | 2 | 54 | 52 |
| B | 82 | 64 | 95 | 91 | 99 |
| D | 51 | 76 | 47 | 26 | 79 |
| E | 60 | 38 | 50 | 52 | 51 |
| F | 40 | 5 | 45 | 27 | 30 |

Pharmacokinetics

Pharmacokinetic screening in rats was performed on various compounds to measure brain to plasma ratio at 2 hour time point. (See Table 5 and 6) For some compounds 24 hour pharmacokinetic study in rat was performed to measure AUC in plasma and brain. (See Table 7). The parameters for the pharmacokinetic protocol were as follows.

Amount of compound: 5 mg/kg
Species: Rat; Strain: Sprague Dawley; Sex: Male
Diet Status: Overnight fasting
Number of Animals (n) for each time point: 2
Dosing: Oral (PO)
Formulation: 0.1% CMC, 0.25% Tween 80 in distilled water Each formulation was administered once by oral gavage using a gavage needle (18G-3, BrainTree Scientific, INC, USA) attached to a syringe. The dose volume was 5 mL/kg for all animals. The actual volume administered to each animal was calculated and adjusted based on the most recent body weight.

Blood samples (approximately 300 μL whole blood) was collected from each animal via tail vein except for terminal blood samples. Terminal blood samples were collected via cardiac puncture. All samples were collected into tubes containing lithium heparin (Multivette 600 LH-Gel, Sarstedt, Newton, N.C., USA). Following collection, the tubes were placed in refrigerator (maximum 30 minutes) or until centrifugation under refrigeration (at 2 to 8° C.) at 5000 g for 7 minutes. Each harvested plasma sample was then transferred into 1.2 mL polypropylene tubes, on the 96-Well Plate according to the 96-Well Plate plasma sample map and kept in freezer. Plasma samples were then analyzed for test substances.

Brain samples were collected immediately after the rats were euthanised at designated time points. Brain samples were rinsed with saline, blotted dry, and weighed. Brain samples were placed into individual containers and kept in freezer (−20° C.). Brain samples were then analyzed for test articles.

After analysis, all the plasma results were reported as ng/mL and brain sample results are reported as ng/g.

Tables 4 and 5 list the compounds of Examples 1-64 and Examples A, B, C that were screened for pharmacokinetic properties. Those compounds of Examples 1-64 not listed in Table 4 were not tested. For the AUC data, + represents values less than 5,000 h*ng/g, ++ represents values between 10,000 and 5,000 h*ng/g, +++ represents values between 20,000 and 10,000 h*ng/g, and ++++ represents values above 20,000 h*ng/g. The abbreviation n.d. means not determined.

TABLE 4

Pharmacokinetic Data

| Example | Plasma - 2 hours (ng/mL) | Brain - 2 hours (ng/g) | Plasma:Brain Ratio | Brain - 24 hours AUC (h * ng/g) |
|---------|---------|---------|---------|---------|
| 2 | 261 | 80 | 3.3:1 | n.d. |
| 3 | 2654 | 691 | 3.8:1 | n.d. |
| 4 | 590 | 98 | 6.0:1 | n.d. |
| 5 | 3780 | 1455 | 2.6:1 | n.d. |
| 6 | 445 | 248 | 1.8:1 | + |
| 7 | 6462 | 3930 | 1.6:1 | ++++ |
| 8 | 5160 | 1580 | 3.3:1 | n.d. |
| 9 | 3062 | 2075 | 1.5:1 | +++ |
| 25 | 10475 | 552 | 19.0:1 | +++ |
| 26 | 6264 | 942 | 6.6:1 | +++ |
| 38 | 8400 | 3515 | 2.4:1 | ++++ |
| 39 | 7625 | 1910 | 4.0:1 | n.d. |
| 42 | 50 | 42 | 1.2:1 | n.d. |
| 46 | 1039 | 536 | 1.9:1 | n.d. |
| 47 | 2089 | 886 | 2.4:1 | + |
| 48 | 486 | 251 | 1.9:1 | n.d. |
| 54 | 7711 | 2979 | 2.6:1 | ++++ |
| 58 | 1327 | 720 | 1.8:1 | n.d. |

TABLE 5

Pharmacokinetic Data

| Example | Plasma - 2 hours (ng/mL) | Brain - 2 hours (ng/g) | Plasma:Brain Ratio | Brain - 24 hours AUC (h * ng/g) |
|---------|---------|---------|---------|---------|
| A | 3850 | 1138 | 3.4:1 | + |
| B | 3083 | 2112 | 1.5:1 | n.d. |
| C | 2459 | 1236 | 2.0:1 | n.d. |

As described in Embodiment 1 above, a feature of compounds of Embodiment 1 is a saturated carbocyclic ring directly attached or linked through a —CH$_2$— group to the 4-position of the core thiazole ring in combination with a substituted thiophene ring linked through a —N—CH$_2$— group to the 2-position of the core thiazole group.

As previously stated above, each of the compounds in Examples 1-64 has an EC50 in the multicomponent functional assay below 5 micromolar. In addition, a subgroup of Embodiment 1 has significantly lower EC50's at about or below 600 nanomolar. See Table 1.

A further property of a subgroup of Embodiment 1 is the microsomal stability in human, monkey, dog, rat, and mouse liver microsomes. For example the compounds of Examples 7, 8, 9, 25, 26, 38, and 60 each have at least 50% compound remaining after 1 hour in each one of the species tested. Compare the stability of Examples A, D, E, and F in various species. See Tables 2 and 3.

A further property of a subgroup of Embodiment 1 is the brain concentration above 1500 ng/g after 2 hours and a plasma to brain concentration ratio after 2 hours of less than 3.0 in addition to having a microsomal stability greater than 50% across all species tested and an EC50 below 600 nanomolar. For example, the compounds of Examples 7, 9, and 38 each have a brain concentration above 1400 ng/g after 2 hours and a plasma to brain concentration ratio after 2 hours of less than 3.0. Compare the brain concentration of Examples 2, 3, 4, 5, 6, 8, 25, 26, 39, 42, 46, 47, 48, and 58, as well as Example A and C.

Sexual Behavior
Sub-Chronic Regimen

Rats were ovariectomized (OVX) under ketamine/xylazine anesthesia with 8 rats per group. OVX rats were then administered estradiol benzoate (10 micrograms) 48 hours and progesterone (500 micrograms) 4 hours before five baseline tests of sexual behavior with sexually vigorous stud males. Tests were 30 minutes in duration and were conducted at 4-day intervals. All females developed normal rates of appetitive and consummatory sexual behavior. Following this baseline test phase, females were switched to an estrogen-alone baseline phase, during which they were administered estradiol benzoate (10 micrograms) 48 hours before tests of sexual behavior with sexually vigorous males. These tests were conducted at 14-day intervals, to assure low rates of appetitive responding (e.g., solicitations, hops and darts). After the second test, females were assigned randomly to 4 groups, a saline control, two doses of Example 7 antagonist (10 and 30 mg/kg, PO), and a positive control using melanotan II (MT-II) (1 mg/kg, SC). The saline control and Example 7 were gavaged daily for 5 days prior to the test. The MT-II control was injected acutely 5 min prior to the test. The test was recorded on video and scored by a technician blind to which drug the animals were receiving. Behaviors were subjected to one-way ANOVAs. For each significant effect, posthoc tests were conducted on the means using the Tukey method, P<0.05.

Example 7 (at 30 mg/kg/day) increased the mean number of solicitations after sub-chronic regimen in OVX rats by a factor of 6 relative to saline and by a factor of 2 relative to MT-II. Example 7 (at 30 mg/kg/day) increased the mean frequency of high-intensity lordosis postures after sub-chronic regimen in OVX rats by a factor of 3.5 relative to saline and by a factor of 3.2 relative to MT-II.

Feeding Study 27 adult male Sprague Dawley rats (Charles River Laboratories) were implanted with right lateral cerebral ventricular cannulas and allowed to recover for one week. After one week, animals were then randomized into 4 groups that were matched for food intake and body weight: water gavage-icv saline (n=6); Example 7 gavage-icv saline (n=7); water gavage-icv AgRP (n=7); Example 7 gavage-icv AgRP (n=7). Water or Example 7 (30 mg/kg) was administered at by oral gavage followed by icv injection of either saline or 0.2 nmol human AgRP 83-132. AgRP stimulated food intake and body weight gain over the next 24 h compared to saline controls. Both of these effects of AgRP were blocked by injection administration of Example 7. There was no significant effect of Example 7+icv saline on food intake or weight gain compared to water+icv saline.

On day 2 a second dose of Example 7 (30 mg/kg) or water was administered by oral gavage. On day 3, water or Example 7 (30 mg/kg) was administered for the third and final time by oral gavage followed by icv injection of either saline or 0.2 nmol human AgRP83-132. Food intake and body weight were monitored daily and animals were sacrificed on day 5. Cumulative weight gain over the entire period was significantly higher after icv AGRP+$H_2O$ (above 30 grams), and this increase was attenuated by administration of Example 7 so that the cumulative weight gain was less than about 15 grams.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the mammal being treated for melanocortin receptor-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. A compound of the following formula or a pharmaceutically acceptable salt thereof:

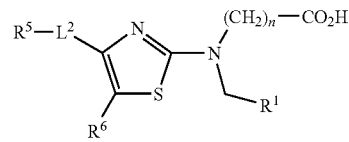

wherein n is 1, 2 or 3;

$R^1$ is selected from the group consisting of:

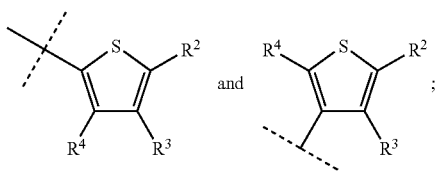

wherein $R^2$ is selected from the group consisting of: —$C_{1-4}$ alkyl and -$L^1$-$C_{1-4}$ alkyl, wherein $L^1$ is selected from the group consisting of —S—, and —$SO_2$—, $R^3$ is selected from the group consisting of: hydrogen and —$C_{1-4}$ alkyl, $R^4$ is selected from the group consisting of: hydrogen and —$C_{1-4}$ alkyl, wherein the alkyl groups in $R^2$, $R^3$, and $R^4$ are optionally substituted with one or more substituents independently selected from the group consisting of: fluoro and chloro;

$L^2$ is a direct bond;
$R^5$ is

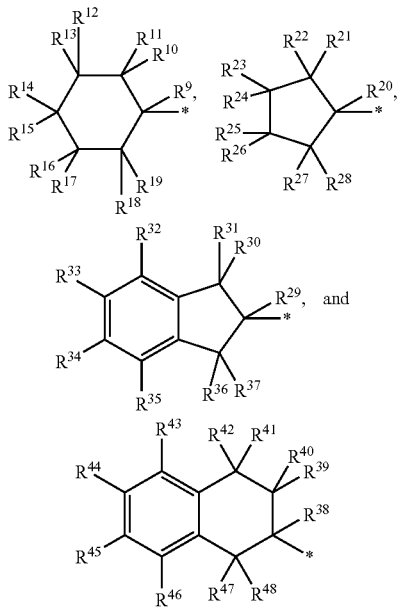

wherein
each of $R^9$, $R^{10}$, $R^{11}$, $R^{12}$, $R^{13}$, $R^{14}$, $R^{15}$, $R^{16}$, $R^{17}$, $R^{18}$ and $R^{19}$ is independently $R^a$, and
$R^6$ is selected from the group consisting of: hydrogen and methyl, wherein the methyl group is optionally substituted with one or more halogens;
wherein
$R^a$ is selected from the group consisting of: -hydrogen, -halogen, —$C_{1-6}$ alkyl, -phenyl, cycloalkyl, and —O—$C_{1-6}$ alkyl,
wherein the alkyl, cycloalkyl, and phenyl groups are each optionally substituted with one or more substituents independently selected from $R^b$; and
$R^b$ is selected from the group consisting of: halogen, —$C_{1-6}$ alkyl, and -halo-$C_{1-4}$ alkyl.

2. The compound of claim 1, wherein n is 2; and
$R^1$ is

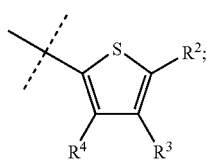

wherein
$R^2$ is selected from the group consisting of: —$C_{1-4}$ alkyl and -$L^1$-$C_{1-4}$ alkyl, wherein $L^1$ is selected from the group consisting of —S—, and —$SO_2$—,
$R^3$ is selected from the group consisting of: hydrogen and —$C_{1-4}$ alkyl, and
$R^4$ is selected from the group consisting of: hydrogen and —$C_{1-4}$ alkyl, wherein the alkyl groups in $R^2$, $R^3$, and $R^4$ are optionally substituted with one or more substituents independently selected from the group consisting of: fluoro and chloro.

3. The compound of claim 2, wherein $R^3$ and $R^4$ are hydrogen, and $R^2$ is methyl.

4. The compound of claim 1, wherein $R^9$, $R^{10}$, $R^{11}$, $R^{12}$, $R^{13}$, $R^{16}$, $R^{17}$, $R^{18}$ and $R^{19}$ are hydrogen, and at least one of $R^{14}$ and $R^{15}$ is not hydrogen.

5. The compound of claim 4, wherein $R^{14}$ is hydrogen, and $R^{15}$ is selected from the group consisting of: -halogen, —$C_{1-6}$ alkyl, -phenyl, —$C_{5-6}$ cycloalkyl, and —O—$C_{1-6}$ alkyl,
wherein the alkyl, cycloalkyl, and phenyl groups are each optionally substituted one or more times with substituents independently selected from $R^b$.

6. The compound of claim 5, wherein $R^{15}$ is selected from the group consisting of: -methyl, -ethyl, -propyl, -isopropyl, and -tert-butyl.

7. The compound of claim 1, wherein
n is 2;
$R^1$ is

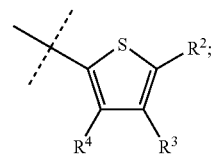

wherein
$R^2$ is methyl; and
$R^3$ and $R^4$ are hydrogen;
$L^2$ is a direct bond; and
$R^5$ is

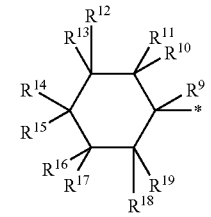

wherein
$R^9$, $R^{10}$, $R^{11}$, $R^{12}$, $R^{13}$, $R^{14}$, $R^{16}$, $R^{17}$, $R^{18}$ and $R^{19}$ are hydrogen, and $R^{15}$ is selected from the group consisting of: -methyl, -ethyl, -propyl, -isopropyl, and -tert-butyl.

8. The compound of claim 1, wherein
n is 2;
$R^1$ is selected from the group consisting of:

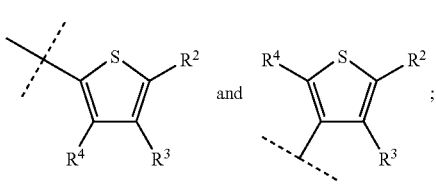

wherein
$R^2$ is —$C_{1-4}$ alkyl,
$R^3$ is hydrogen or —$C_{1-4}$ alkyl, and
$R^4$ is hydrogen or —$C_{1-4}$ alkyl;

L² is a direct bond;
R⁵ is

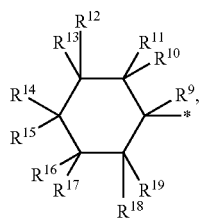

wherein
R⁹, R¹⁰, R¹¹, R¹², R¹³, R¹⁶, R¹⁷, R¹⁸ and R¹⁹ are hydrogen;
and at least one of R¹⁴ and R¹⁵ is not hydrogen; and
R⁶ is hydrogen;
$R^a$ is selected from the group consisting of: -hydrogen, —$C_{1-6}$ alkyl, -phenyl, and -cyclohexyl,
wherein the alkyl, cyclohexyl, and phenyl groups are each optionally substituted with one or more substituents independently selected from $R^b$; and
$R^b$ is —$C_{1-6}$ alkyl.

9. The compound of claim 1, wherein
n is 2;
R¹ is

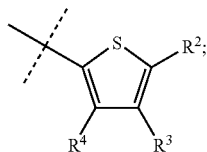

wherein
R² ethyl or methyl, and
R³ and R⁴ are hydrogen;
L² is a direct bond;
R⁵ is

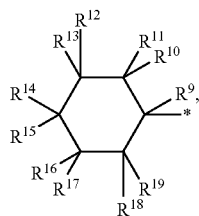

wherein
R⁹, R¹⁰, R¹¹, R¹², R¹³, R¹⁴, R¹⁶, R¹⁷, R¹⁸ and R¹⁹ are hydrogen; and
R¹⁵ is selected from the group consisting of: tert-butyl, isopropyl, and phenyl; and
R⁶ is hydrogen.

10. The compound of claim 1, wherein R² is methyl.

11. A compound, which is a compound selected from the group consisting of:
3-[[4-(trans-4-tert-butyl-cyclohexyl)-thiazol-2-yl]-(5-methyl-thiophen-2-ylmethyl)-amino]-propionic acid;
3-[[4-(4-isopropyl-cyclohexyl)-thiazol-2-yl]-(5-methyl-thiophen-2-ylmethyl)-amino]-propionic acid;
3-{(5-Methyl-thiophen-2-ylmethyl)-[4-(4-trifluoromethyl-cyclohexyl)-thiazol-2-yl]-amino}-propionic acid;
3-[[4-(4-Ethyl-cyclohexyl)-thiazol-2-yl]-(5-methyl-thiophen-2-ylmethyl)-amino]-propionic acid;
3-{(5-Methyl-thiophen-2-ylmethyl)-[4-(4-propyl-cyclohexyl)-thiazol-2-yl]-amino}-propionic acid;
3-[[4-(4,4-difluoro-cyclohexyl)-thiazol-2-yl]-(5-methyl-thiophen-2-ylmethyl)-amino]-propionic acid;
3-[[4-(4-tert-Butyl-cyclohexyl)-thiazol-2-yl]-(5-methyl-thiophen-2-ylmethyl)-amino]-propionic acid;
3-[[4-(4-Methoxy-cyclohexyl)-thiazol-2-yl]-(5-methyl-thiophen-2-ylmethyl)-amino]-propionic acid;
3-{(5-methyl-thiophen-2-ylmethyl)-[4-(trans-4-phenyl-cyclohexyl)-thiazol-2-yl]-amino}-propionate;
3-[[4-(4,4-Dimethyl-cyclohexyl)-thiazol-2-yl]-(5-methyl-thiophen-2-ylmethyl)-amino]-propionic acid;
3-[(4-bicyclohexyl-4-yl-thiazol-2-yl)-(5-methyl-thiophen-2-ylmethyl)-amino]-propionic acid; and
3-[{4-[4-(4-fluoro-phenyl)-cyclohexyl]-thiazol-2-yl}-(5-methyl-thiophen-2-ylmethyl)-amino]-propionic acid;
or a pharmaceutically acceptable salt thereof.

12. 3-[[4-(trans-4-Tert-butyl-cyclohexyl)-thiazol-2-yl]-(5-methyl-thiophen-2-ylmethyl)-amino]-propionic acid or a pharmaceutically acceptable salt thereof.

13. A pharmaceutical composition comprising a compound of claim 1 and a pharmaceutically acceptable carrier, excipient, diluent, or mixture thereof.

14. A method of treatment of a disorder comprising: administering to a subject a therapeutically effective amount of a compound of claim 1, wherein the disorder is selected from the group consisting of female sexual dysfunction, and male sexual dysfunction.

15. A method of treatment comprising: administering to a subject a therapeutically effective amount of a compound of claim 1, wherein the compound is administered in an amount sufficient to induce weight loss, halt weight gain, or decrease the rate of weight gain in the subject.

16. A pharmaceutical composition comprising a compound of claim 11 and a pharmaceutically acceptable carrier, excipient, diluent, or mixture thereof.

17. A pharmaceutical composition comprising a compound of claim 12 and a pharmaceutically acceptable carrier, excipient, diluent, or mixture thereof.

* * * * *